United States Patent
Yu

(10) Patent No.: US 11,041,201 B2
(45) Date of Patent: *Jun. 22, 2021

(54) METHODS FOR DETECTION OF RNASE ACTIVITY

(71) Applicant: The Regents of the University of California, Oakland, CA (US)

(72) Inventor: Aiming Yu, Granite Bay, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/577,762

(22) Filed: Sep. 20, 2019

(65) Prior Publication Data

US 2020/0056236 A1 Feb. 20, 2020

Related U.S. Application Data

(62) Division of application No. 15/558,563, filed as application No. PCT/US2016/022681 on Mar. 16, 2016, now Pat. No. 10,422,003.

(60) Provisional application No. 62/137,201, filed on Mar. 23, 2015.

(51) Int. Cl.
| | |
|---|---|
| *C12Q 1/6876* | (2018.01) |
| *C12N 15/113* | (2010.01) |
| *C12N 15/115* | (2010.01) |
| *C12Q 1/44* | (2006.01) |

(52) U.S. Cl.
CPC .......... *C12Q 1/6876* (2013.01); *C12N 15/113* (2013.01); *C12N 15/115* (2013.01); *C12Q 1/44* (2013.01); *C12N 2310/14* (2013.01); *C12N 2310/141* (2013.01); *C12N 2310/16* (2013.01); *C12N 2310/3519* (2013.01); *G01N 2333/922* (2013.01)

(58) Field of Classification Search
None
See application file for complete search history.

(56) References Cited

U.S. PATENT DOCUMENTS

| | | | | |
|---|---|---|---|---|
| 10,422,003 | B2* | 9/2019 | Yu ........................ | C12Q 1/6876 |
| 10,619,156 | B2* | 4/2020 | Yu ........................ | C12N 15/11 |
| 2005/0075492 | A1 | 4/2005 | Chen et al. | |
| 2007/0037171 | A1* | 2/2007 | Lu ..................... | C12Q 2525/205 |
| | | | | 435/6.11 |
| 2007/0161004 | A1* | 7/2007 | Brown ................. | C12Q 1/6809 |
| | | | | 435/6.14 |
| 2007/0287678 | A1* | 12/2007 | Slack ................. | G01N 33/6893 |
| | | | | 514/44 A |
| 2009/0004668 | A1 | 1/2009 | Chen et al. | |
| 2009/0298920 | A1 | 12/2009 | Dardel et al. | |
| 2010/0087336 | A1* | 4/2010 | Jackson ............. | G01N 33/5308 |
| | | | | 506/26 |
| 2010/0144831 | A1 | 6/2010 | Fakhral et al. | |
| 2010/0291561 | A1 | 11/2010 | Milligan et al. | |
| 2013/0338215 | A1 | 12/2013 | Lieberman et al. | |
| 2014/0162289 | A1 | 6/2014 | Wright et al. | |

FOREIGN PATENT DOCUMENTS

| | | | | |
|---|---|---|---|---|
| EP | | 2566515 | 3/2013 | |
| WO | WO-9951755 | A2 * | 10/1999 | ......... A01K 67/0278 |
| WO | WO 2013106766 | | 7/2013 | |
| WO | WO 2013170365 | | 11/2013 | |
| WO | WO 2015183667 | | 12/2015 | |
| WO | WO 2016153880 | | 9/2016 | |

OTHER PUBLICATIONS

Bogerd et al. (2010) "A Mammalian Herpesvirus Uses Noncanonical Expression and Processing Mechanisms to Generate Viral MicroRNAs" Molecular Cell, 37:135-142.
Chen et al., (2014) "A general approach to high-yield biosynthesis of chimeric RNAs bearing various types of functional small RNAs for broad applications," SCHOLARONE Manuscripts, Oxford University Press, [for Peer Review] 27pp.
Chen et al., (2015) "A general approach to high-yield biosynthesis of chimeric RNAs bearing various types of functional small RNAs for broad applications," Nucleic Acids Research, 43(7):3857-3869 [retrieved on Mar. 23, 2015 at http://nar.oxfordjournals.org/], 13pp.
Duan et al., (Nov. 2016) "Bioengineered non-coding RNA agent (BERA) in action," Bioengineered, 7(6):411-417.
Extended European Search Report dated Feb. 20, 2018 issued in EP 15800458.0.
Ho et al., (Mar. 2016) "Bioengineering of noncoding RNAs for research agents and therapeutics," Wiley Interdiscip Rev RNA, 7(2): 186-197.
Jian et al., (2017) "Co-targeting of DNA, RNA, and protein molecules provides optimal outcomes for treating osteosarcoma and pulmonary metastasis in spontaneous and experimental metastasis mouse models," Oncotarget, 8(19):30742-30755.
Li et al., (Nov. 2014) "Rapid Production of Novel Pre-MicroRN a Agent hsa-mir-27b in *Escherichia coli* Using Recombinant RNA Technology for Functional Studies in Mammalian Cells," Drug Metab Dispos, 42(11):1791-1795 [Downloaded from dmd.aspetjournals. org at ASPET Journals on Jul. 27, 2016].

(Continued)

*Primary Examiner* — Brian Whiteman
(74) *Attorney, Agent, or Firm* — Brian E. Davy; Bozicevic, Field & Francis LLP

(57) ABSTRACT

Provided are polynucleotides that find use, e.g., for detecting RNase activity. In certain embodiments, the polynucleotide comprises a tRNA operably linked to a pre-microRNA (pre-miRNA), and an aptamer that binds to a detectable label. According to some embodiments, the detectable label is a fluorescent dye, non-limiting examples of which include malachite green, tetramethylrosamine, sulforhodamine B, and a triphenylmethane dye. Also provided are compositions that include the polynucleotides of the present disclosure. Also provided are kits that include a polynucleotide of the present disclosure and a detectable label to which the aptamer of the polynucleotide binds.

16 Claims, 14 Drawing Sheets
Specification includes a Sequence Listing.

(56) References Cited

OTHER PUBLICATIONS

Li et al., (Jul. 2015) "Chimeric MicroRNA-1291 Biosynthesized Efficiently in *Escherichia coli* Is Effective to Reduce Target Gene Expression in Human Carcinoma Cells and Improve Chemosensitivity," Drug Metabolism and Disposition, 43(7): 1129-1136.

Liu et al., (2010) "DNAzyme-mediated recovery of small recombinant RNAs from a 5S rRNA-derived chimera expressed in *Escherichia coli*," BMC Biotechnology, 10:85, 9pp.

Nelissen et al., (2012) "Fast production of homogeneous recombinant RNA—towards large-scale production of RNA," Nucleic Acids Research, 40(13):e102, 12pp [Downloaded on Mar. 19, 2013 at http://nar.oxfordjournals.org/ at Kainan University].

Pan et al., (Oct. 2013) "Small Nucleolar RNA-Derived MicroRNA hsamiR-1291 Modulates Cellular Drug Disposition through Direct Targeting of ABC Transporter ABCC1," Special Section on Epigenetic Regulation of Drug Metabolizing Enzymes and Transporter, Drug Metabolism and Disposition, 41(10):1744-1751.

Pavon-Eternod et al., (2013) "Overexpression of initiator methionine tRNA leads to global reprogramming of tRNA expression and increased proliferation in human epithelial cells," RNA, 19(4):461-466 [Downloaded from rnajournal.cshlp.org on Oct. 11, 2016—Published by Cold Spring Harbor Laboratory Press].

PCT International Search Report and Written Opinion dated Sep. 16, 2015 issued in PCT/US2015/031861.

PCT International Preliminary Report on Patentability and Written Opinion dated Dec. 8, 2016 issued in PCT/US2015/031861.

PCT Invitation to Pay Additional Fees and, Where Applicable, Protest Fee dated Aug. 3, 2016 issued in PCT/US2016/22681.

PCT International Search Report and Written Opinion dated Oct. 5, 2016 issued in PCT/US2016/22681.

PCT International Preliminary Report on Patentability and Written Opinion dated Oct. 5, 2017 issued in PCT/US2016/22681.

Ponchon et al., (Jul. 2007) "Recombinant RNA technology: the tRNA scaffold," Nature Methods, 4(7):571-576.

Ponchon et al., (2009) "A generic protocol for the expression and purification of recombinant RNA in *Escherichia coli* using a tRNA scaffold," Nature Protocols, 4(6):947-959.

Reddi et al. (1976) "Elevated serum ribonuclease in patients with pancreatic cancer" PNAS, 73(7):2308-2310.

Reese et al., (2010) "Identification of Novel MicroRNA-Like Molecules Generated from Herpesvirus and Host tRNA Transcripts," Journal of Virology, 84(19): 10344-10353.

Scherer et al., (2007) "Optimization and characterization of tRNA-shRNA expression constructs," Nucleic Acids Research, 35(8):2620-2628.

Shukla et al. (2012) "MicroRNAs: Processing, Maturation, Target Recognition and Regulatory Functions" Mol. Cell Pharmacol., 3(3):83-92.

Tarasov et al., (2007) "Differential Regulation of microRNAs by p53 Revealed by Massively Parallel Sequencing: MiR-34a is a p53 Target That Induces Apoptosis and G 1-arrest," Cell Cycle, 6(13): 1586-1593.

Urayama et al., (2015) "Application of novel RNA aptamer-based Rnase I activity assay for pancreatic cancer biomarker development," American Association for Cancer Research, Annual Meeting Apr. 18-22, 2015, Philadelphia, Presentation Abstract, 2 pp [retrieved on Mar. 21, 2015 at http://www.abstractsonline.com/Plan/AbstractPrint View .aspx ?miD=3682&sK ey=cae555b . . . ].

Wang et al., (Aug. 2015) "Bioengineering Novel Chimeric microRNA-34a for Prodrug Cancer Therapy: High-Yield Expression and Purification, and Structural and Functional Characterization," The Journal of Pharmacology and Experimental Therapeutics, 354(2): 131-141.

Zhao et al., (May 24, 2016) "Genetically engineered pre-microRNA-34a prodrug suppresses orthotopic osteosarcoma xenograft tumor growth via the induction of apoptosis and cell cycle arrest," Scientific Reports, 6:26611, 11pp.

\* cited by examiner

SEQUENCE LISTING

```
<160> NUMBER OF SEQ ID NOS: 85

<210> SEQ ID NO 1
<211> LENGTH: 107
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 1
ggcuacguag cucaguuggu uagagcagcg gccgaguaau uuacgucgac ggugacgucg    60
```

```
augguugcgg ccgcggguca cagguucgaa ucccgucgua gccacca        107

<210> SEQ ID NO 2
<211> LENGTH: 110
<212> TYPE: RNA
<213> ORGANISM: Homo sapiens

<400> SEQUENCE: 2
ggccagcugu gaguguuucu uuggcagugu cuuagcuggu uguugugagc aauaguaagg    60
aagcaaucag caaguauacu gcccuagaag ugcugcacgu ugugggggccc              110

<210> SEQ ID NO 3
<211> LENGTH: 233
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 3
ggcuacguag cucaguuggu uagagcagcg gccgaguaau uuacgucgac guggaccggc    60
cagcugugag uguuucuuug gcagugucuu agcugguugu ugugagcaau aguaaggaag    120
caaucagcaa guauacugcc cuagaaugug cugcacgugu ggggcccaag agggaagaug    180
acgucgaugg uugcggccgc gggucacagg uucgaauccc gucuagcca cca            233

<210> SEQ ID NO 4
<211> LENGTH: 195
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 4
ggcuacguag cucaguuggu uagagcagcg gccgguggac cggccagcug ugaguguuuc    60
uuuggcagug ucuuagcugg uuguugugag caauaguaag gaagcaauca gcaaguauac    120
ugcccuagaa gugcugcacg uugugggggcc cggucaccc gcggguccaca gguucgaauc    180 ccgucguagc cacca                                                    195

<210> SEQ ID NO 5
<211> LENGTH: 198
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 5
ggcuacguag cucaguuggu uagagcagcg gccgggccag cugugagugu uucuuuggca    60
gugucuuagc ugguuguugu gagcaauagu aaggaagcaa ucagcaagua uacugcccua    120
gaagugcugc acguugugggg gcccgacguc gaugguugcg ccgcgggguc acagguucga    180
aucccgucgu agccacca                                                 198

<210> SEQ ID NO 6
<211> LENGTH: 181
<212> TYPE: RNA
<213> ORGANISM: Artificial Sequence
<220> FEATURE:
<223> OTHER INFORMATION: Description of Artificial Sequence: Synthetic
``` polynucleotide

<400> SEQUENCE: 6
ggcuacguag cucaguuggu uagagcagcg gccgggccag cugugagugu uucuuuggca    60
gugucuuagc ugguuguugu gagcaauagu aaggaagcaa ucagcaagua uacugcccua   120
gaagugcugc acguuguggg gccccgcgg gucacagguu cgaaucccgu cguagccacc   180
a                                                                   181

<210> SEQ ID NO 7
<211> LENGTH: 180
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 7
ggcuacguag cucaguuggu uagagcagcg gccgggccag cugugagugu uucuuuggca    60
gugucuuagc ugguuguugu gagcaauagu aaggaagcaa ucagcaagua uacugcccua   120
gaagugcugc acguuguugg ccccgcggg ucacagguuc gaaucccguc guagccacca   180

<210> SEQ ID NO 8
<211> LENGTH: 181
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 8
ggcuacguag cucaguuggu uagagcagcg gccgggcccc gcugugagug uuucuuuggc    60
agugucuuag cugguuguug ugagcaauag uaaggaagca aucagcaagu auacugcccu   120
agaagugcug cacguguggg gccccgcgg gucacagguu cgaaucccgu cguagccacc   180
a                                                                   181

<210> SEQ ID NO 9
<211> LENGTH: 38
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 9
ggaucccgac uggcgagagc cagguaacga auggaucc                           38

<210> SEQ ID NO 10
<211> LENGTH: 233
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 10
ggcuacguag cucaguuggu uagagcagcg gccgggaucc cgacuggcga gagccaggua    60
acgaauggau ccguggaccg gccagcugug aguguuucuu uggcagugu uuagcugguu   120 guugugagca auaguaagga agcaaucagc aaguauacug cccuagaagu gcugcacguu   180
gugggccccg guccacccgc gggucacagg uucgaauccc gucguagcca cca          233

<210> SEQ ID NO 11
<211> LENGTH: 233
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 11
ggcuacguag cucaguuggu uagagcagcg gccgguggac cggccagcug ugaguguuuc    60
uuuggcagug ucuuagcugg uuguugugag caauaguaag gaagcaauca gcaaguauac   120
ugcccuagaa gugcugcacg uugugggggcc cgguccacgg aucccgacug gcgagagcca   180
gguaacgaau ggauccccgc gggucacagg uucgaauccc gucguagcca cca          233

<210> SEQ ID NO 12
<211> LENGTH: 121
<212> TYPE: RNA
<213> ORGANISM: Homo sapiens

<400> SEQUENCE: 12
aguucugucc gugagccuug gguagaauuc caguggcccu gacugaagac cagcaguugu    60
acuguggcug uugguuucaa gcagaggccu aaaggacugu cuuccugugg ucguuggcu    120 g                                                                  121

<210> SEQ ID NO 13
<211> LENGTH: 227
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 13
ggcuacguag cucaguuggu uagagcagcg gccgaguaau uuacgucgac gaguucuguc    60
cgugagccuu ggguagaauu ccaguggccc ugacugaaga ccagcaguug uacguggcu   120 guugguuuca agcagaggcc uaaaggacug ucuuccugug gucguuggc ugugacgucg   180 augguugcgg ccgcggguca cagguucgaa ucccgucgua gccacca               227

<210> SEQ ID NO 14
<211> LENGTH: 110
<212> TYPE: RNA
<213> ORGANISM: Homo sapiens

<400> SEQUENCE: 14
agaaaacauu guugcgcucc ucucaguccc ugagacccua acuugugaug uuuaccguuu    60
aaauccacgg guuaggcucu ugggagcugc gagucgugcu uuugcauccu              110

<210> SEQ ID NO 15
<211> LENGTH: 216
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 15
ggcuacguag cucaguuggu uagagcagcg gccgaguaau uuacgucgac gagaaaacau    60
uguugcgcuc cucucaguccc cugagacccu aacuugugau guuuaccguu uaaauccacg   120

```
gguuaggcuc uugggagcug cgagucgugc uuuugcaucc uugacgucga ugguugcggc    180
cgcgggucac agguucgaau cccgucguag ccacca                             216

<210> SEQ ID NO 16
<211> LENGTH: 233
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Description of Combined DNA/RNA Molecule:
      Synthetic polynucleotide

<400> SEQUENCE: 16
ggcuacguag cucaguuggu uagagcagcg gccgaguaau uuacgucgac guggaccggc    60
cagcugugag uguuucuuug gcagugucuu agcugguugu ugugagcaau aguaaggaag    120
caaucagcaa guauacugcc cuagaagugc ugcacguug gggcccaag agggaagaug      180 acgucgaugg uugcggccgc gggucacagg uucgaauccc gucuagcca cca            233

<210> SEQ ID NO 17
<211> LENGTH: 228
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 17
ggcuacguag cucaguuggu uagagcagcg gccgaguaau uuacgucgac ccguggaccg    60
gccagcugug aguguuucuu uaaggcacgc ggugaaugcc ugugagcaau aguaaggaag    120
gcauucacgc ugugccuucu agaagugcug cacguugugg ggcccaagag ggaagacguc    180
gaugguugcg gccgcgggguc acagguucga aucccgucgu agccacca                228

<210> SEQ ID NO 18
<211> LENGTH: 232
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 18
ggcuacguag cucaguuggu uagagcagcg gccgaguaau uuacgucgac ccguggaccg    60
gccagcugug aguguuucuu caccuauaac aacgguaguu uuugugagca auaguaagga    120
agaaacuacc uuguuuauag gucuagaagu gcugcacguu gugggcccca agagggaaga    180
cgucgauggu ugcggccgcg ggucacaggu ucgaauccc gucuagccac ca              232

<210> SEQ ID NO 19
<211> LENGTH: 232
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 19
ggcuacguag cucaguuggu uagagcagcg gccgaguaau uuacgucgac ccguggaccg    60
gccagcugug aguguuucuu aguugacucuc cagcuugugc ccugugagca auaguaagga   120
```
agggcacaag ugguaguaca accuagaagu gcugcacguu gugggccca agagggaaga      180 cgucgauggu ugcggccgcg ggucacaggu ucgaaucccg ucuagccac ca              232

<210> SEQ ID NO 20
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
acgcgtcgac ccagcgatga cctctctaac                                      30

<210> SEQ ID NO 21
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
catcgacgtc cttaactgtc cccatctcac c                                    31

<210> SEQ ID NO 22
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
agtaatttac gtcgacgtgg accggccagc tgtgagtgtt                           40

<210> SEQ ID NO 23
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
cggccgcaac catcgacgtc atcttccctc ttgggcccca caacg                     45

<210> SEQ ID NO 24
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
agtaatttac gtcgacttcg tggctacaga gtttccttag cag                       43

<210> SEQ ID NO 25
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
cggccgcaac catcgacgtc caagacattt atcgagggaa ggattgc         47

<210> SEQ ID NO 26
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
agtaatttac gtcgacctcc tttccttcct caggag         36

<210> SEQ ID NO 27
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
cggccgcaac catcgacgtc cgccgaccca cggtgctca         39

<210> SEQ ID NO 28
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
agtaatttac gtcgactact ttccggatca agattag         37

<210> SEQ ID NO 29
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
cggccgcaac catcgacgtc ttggtgtcct tcaagtgcag         40

<210> SEQ ID NO 30
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
agtaatttac gtcgacagaa aacattgttg cgctcctctc         40

<210> SEQ ID NO 31
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
cggccgcaac catcgacgtc aggatgcaaa agcacgactc gc         42

<210> SEQ ID NO 32
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32
agtaatttac gtcgactcta ccgcatcaaa ccagactttt cc         42

<210> SEQ ID NO 33
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33
cggccgcaac catcgacgtc ctgctggttc ccctccgcc            39

<210> SEQ ID NO 34
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34
agtaatttac gtcgacaggc ttgctgtagg ctgtatgctg            40

<210> SEQ ID NO 35
<211> LENGTH: 50
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 35
cggccgcaac catcgacgtc aatgctagta acaggcatca tacactgtta    50

<210> SEQ ID NO 36
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 36
agtaatttac gtcgaccttg caagctgaac atccaggtct g           41

<210> SEQ ID NO 37
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 37
cggccgcaac catcgacgtc cagccaatgg agaacatgtt tcca         44

<210> SEQ ID NO 38
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 38
acgcgtcgac gagttctgtc cgtgagcctt gg                      32

<210> SEQ ID NO 39
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 39
catcgacgtc acagccaaca gaccacagga ag                      32

<210> SEQ ID NO 40
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 40
agtaatttac gtcgacaccc tggatgttct cttcac                  36

<210> SEQ ID NO 41
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 41
cggccgcaac catcgacgtc gatgcagact tttctatcac g            41

<210> SEQ ID NO 42
<211> LENGTH: 88
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 42
agtaatttac gtcgacccgt ggaccggcca gctgtgagtg tttctttaag gcacgcggtg   60
aatgcctgtg agcaatagta aggaaggc                                      88

<210> SEQ ID NO 43
<211> LENGTH: 89
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 43

-continued

```
cggccgcaac catcgacgtc ttccctcttg ggccccacaa cgtgcagcac ttctagaagg    60
cacagcgtga atgccttcct tactattgc                                      89

<210> SEQ ID NO 44
<211> LENGTH: 90
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 44
agtaatttac gtcgacccgt ggaccggcca gctgtgagtg tttcttcacc tataacaacg    60 gtagttttg tgagcaatag taaggaagaa                                      90

<210> SEQ ID NO 45
<211> LENGTH: 90
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 45
cggccgcaac catcgacgtc ttccctcttg ggccccacaa cgtgcagcac ttctagacct    60
ataaacaagg tagtttcttc cttactattg                                     90

<210> SEQ ID NO 46
<211> LENGTH: 90
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 46
agtaatttac gtcgacccgt ggaccggcca gctgtgagtg tttcttagtt gtactccagc    60
ttgtgccctg tgagcaatag taaggaaggg                                     90

<210> SEQ ID NO 47
<211> LENGTH: 90
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 47
cggccgcaac catcgacgtc ttccctcttg ggccccacaa cgtgcagcac ttctaggttg    60
tactaccact tgtgccttc cttactattg                                      90

<210> SEQ ID NO 48
<211> LENGTH: 83
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 48
agtaatttac gtcgacgagg cttgctgaag gctgtatgct ggttgtactc cagcttgtgc    60
ccgttttggc cactgactga cgg                                            83
```

<210> SEQ ID NO 49
<211> LENGTH: 83
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 49
cggccgcaac catcgacgtc gagtgctagt aacaggcctt gtgtcctggt tgtactccat    60
tgtgcccgtc agtcagtggc caa                                           83

<210> SEQ ID NO 50
<211> LENGTH: 74
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 50
gttagagcag cggccgggat cccgactggc gagagccagg taacgaatgg atccgtggac    60
cggccagctg tgag                                                     74

<210> SEQ ID NO 51
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 51
gaacctgtga cccgcgggtg gaccgggccc cacaacgtgc agca                    44

<210> SEQ ID NO 52
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 52
gttagagcag cggccggtgg accggccagc tgtgag                             36

<210> SEQ ID NO 53
<211> LENGTH: 82
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 53
gaacctgtga cccgcgggga tccattcgtt acctggctct cgccagtcgg gatccgtgga    60
ccgggcccca caacgtgcag ca                                            82

<210> SEQ ID NO 54
<211> LENGTH: 18
<212> TYPE: DNA
<213> ORGANISM: Artificial Sequence
<220> FEATURE:
<223> OTHER INFORMATION: Description of Artificial Sequence: Synthetic primer

<400> SEQUENCE: 54
gcgctaaggc acgcggtg                                                18

<210> SEQ ID NO 55
<211> LENGTH: 50
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 55
gtcgtatcca gtgcagggtc cgaggtattc gcactggata cgacaattgt             50

<210> SEQ ID NO 56
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 56
cctgtggagt tgatcctagt ctgggtg                                      27

<210> SEQ ID NO 57
<211> LENGTH: 50
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 57
gtcgtatcca gtgcagggtc cgaggtattc gcactggata cgacggcatt             50

<210> SEQ ID NO 58
<211> LENGTH: 50
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 58
gtcgtatcca gtgcagggtc cgaggtattc gcactggata cgacgggcac             50

<210> SEQ ID NO 59
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 59
gcgcgcagtt gtactccagc tt                                           22

<210> SEQ ID NO 60
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 60
acgtaaacgg ccacaagttc                                          20

<210> SEQ ID NO 61
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 61
aagtcgtgct gcttcatgtg                                          20

<210> SEQ ID NO 62
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 62
cctaaagcat acgggtcctg                                          20

<210> SEQ ID NO 63
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 63
tttcactttg ccaaacacca                                          20

<210> SEQ ID NO 64
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 64
gtaacccgtt gaaccccatt                                          20

<210> SEQ ID NO 65
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 65
ccatccaatc ggtagtagcg                                          20

<210> SEQ ID NO 66
<211> LENGTH: 228
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 66
ggcuacguag cucaguuggu uagagcagcg gccgaguaau uuacgucgac acccuggaug        60
uucucuucac uguggggauga gguaguaggu uguauaguuu uagggucaca cccaccacug       120
ggagauaacu auacaaucua cugucuuucc uaacgugaua gaaaagucug caucgacguc       180
gauggucgcg gccgcgggcu acagguucga aucccgucgu agccacca                    228

<210> SEQ ID NO 67
<211> LENGTH: 37
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 67
ggcuacguag cucaguuggu uagagcagcg gccgagu                                 37

<210> SEQ ID NO 68
<211> LENGTH: 26
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 68
agguucgaau cccgucguag ccacca                                             26

<210> SEQ ID NO 69
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 69
aguugguuag agcagcggc                                                     19

<210> SEQ ID NO 70
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 70
aguugguuag agcagcggcc                                                    20

<210> SEQ ID NO 71
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 71
aguugguuag agcagcggcc g                                                  21

<210> SEQ ID NO 72
<211> LENGTH: 23
<212> TYPE: RNA

```
<213> ORGANISM: Artificial Sequence
<220> FEATURE:
<223> OTHER INFORMATION: Description of Artificial Sequence: Synthetic
      oligonucleotide

<400> SEQUENCE: 72
aguugguuag agcagcggcc gag                                           23

<210> SEQ ID NO 73
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 73
aaucccgucg uagccacca                                                19

<210> SEQ ID NO 74
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 74
aucccgucgu agccacca                                                 18

<210> SEQ ID NO 75
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 75
cccgucguag ccacca                                                   16

<210> SEQ ID NO 76
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 76
aaucccgucg uagcc                                                    15

<210> SEQ ID NO 77
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 77
gaaucccguc guagccacca                                               20

<210> SEQ ID NO 78
<211> LENGTH: 20
<212> TYPE: RNA
<213> ORGANISM: Artificial Sequence
```

```
<220> FEATURE:
<223> OTHER INFORMATION: Description of Artificial Sequence: Synthetic
      oligonucleotide

<400> SEQUENCE: 78
guucgaaucc cgucguagcc                                              20

<210> SEQ ID NO 79
<211> LENGTH: 32
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 79
ggcuacguag cucaguuggu uagagcagcg gc                                32

<210> SEQ ID NO 80
<211> LENGTH: 30
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 80
ggcuacguag cucaguuggu uagagcagcg                                   30

<210> SEQ ID NO 81
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 81
guucgaaucc cgucguagcc                                              20

<210> SEQ ID NO 82
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 82
cgaaucccgu cguagccacc a                                            21

<210> SEQ ID NO 83
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 83
cccgucguag ccacca                                                  16

<210> SEQ ID NO 84
<211> LENGTH: 233
<212> TYPE: RNA
<213> ORGANISM: Artificial Sequence
<220> FEATURE:
```

-continued

```
<223> OTHER INFORMATION: Description of Artificial Sequence: Synthetic
      polynucleotide

<400> SEQUENCE: 84
ggcuacguag cucaguuggu uagagcagcg gccgggaucc cgacuggcga gagccaggua      60
acgaauggau ccguggaccg gccagcugug aguguuucuu uggcaguguc uuagcugguu     120
guugugagca auaguaagga agcaaucagc aaguauacug cccuagaagu gcugcacguu     180
guggggccca agagggccgc gggucacagg uucgaauccc gucguagcca cca            233

<210> SEQ ID NO 85
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 85
guucgaaucc cgucguagcc acca                                             24
```

METHODS FOR DETECTION OF RNASE ACTIVITY

CROSS-REFERENCE TO RELATED APPLICATIONS

This application is a divisional of U.S. patent application Ser. No. 15/558,563, filed Sep. 15, 2017, which is a 371 of Intl. Appl. No. PCT/US2016/022681, filed on Mar. 16, 2016, which claims the benefit under 35 U.S.C. § 119(e) of U.S. Provisional Application No. 62/137,201, filed on Mar. 23, 2015, which is hereby incorporated herein by reference in its entirety.

STATEMENT OF GOVERNMENTAL SUPPORT

This invention was made with government support under Grant No. 1U01CA175315 awarded by the National Institutes of Health. The government has certain rights in the invention.

FIELD

Provided are compositions and methods for detecting RNase activity.

BACKGROUND

Ribonucleases (RNases) are a family of nucleases involved in the processing and degradation of RNAs (e.g., mRNAs and noncoding RNAs), which are critical for life cycles and cellular defense against infections. Change in RNase activity may be an indicator of human diseases (e.g., inflammation and cancer) and/or disease status. In addition, determination of RNase contamination is essential for RNA research and discovery.

Existing methods for detecting RNase activity include:
1. UV-based assays, which is less selective and thus unable to provide an accurate quantification.
2. Radioactivity-based assays, which requires the production and use of radioactive isotope-labeled RNA substrates.
3. Fluorescence-based assays, which requires the production and use of RNA substrates labeled with fluorophores.

The traditional Kunitz RNase activity assay is based upon the ultraviolet absorbance of label-free nucleic acids or degraded nucleosides, which is less selective, sensitive and accurate. Recent and current RNase activity assays including those commercially-available kits rely on isotope- or fluorophore-labeled RNAs (or antibodies), and thus offer greater sensitivities to determine very low levels of RNase activities (or indicate RNase protein levels). However, labeling methods are limited to the access to inexpensive, large quantities of labeled RNA substrates (e.g., micrograms), whereas biological samples such as human sera are comprised of high levels of RNase activities. Without extensive dilutions (e.g., 1:1,000) of the serum sample that would inevitably affect the RNase activity assay including linear range and accuracy, larger quantities (e.g., >10 µg) of labeled synthetic RNA agents are needed for a direct detection of serum RNase activity using labeling methods. Therefore, direct quantification of RNase activity in serum and other biological samples using labeling assays is costly and a more efficient method is warranted.

SUMMARY

Provided are polynucleotides comprising a tRNA operably linked to a pre-microRNA (pre-miRNA) and an aptamer that binds to a target analyte. In varying embodiments, the tRNA is a methionyl tRNA. In varying embodiments, the tRNA has a nucleic acid sequence having at least 90% sequence identity, e.g., at least 91%, 92%, 93%, 94%, 95%, 96%, 97%, 98%, 99% or 100% sequence identity, to SEQ ID NO:1. In varying embodiments, the pre-miRNA is selected from pre-miRNA-1291, pre-miRNA-34a and pre-miRNA-125-1. In varying embodiments, the pre-miRNA-1291 comprises a nucleic acid sequence having at least 90% sequence identity, e.g., at least 91%, 92%, 93%, 94%, 95%, 96%, 97%, 98%, 99% or 100% sequence identity, to the miRBase Accession No. MI0006353. In varying embodiments, the pre-miRNA-34a comprises a nucleic acid sequence having at least 90% sequence identity, e.g., at least 91%, 92%, 93%, 94%, 95%, 96%, 97%, 98%, 99% or 100% sequence identity, to miRBase Accession No. MI0000268 or SEQ ID NO:2. In varying embodiments, the pre-miRNA-125-1 comprises a nucleic acid sequence having at least 90% sequence identity, e.g., at least 91%, 92%, 93%, 94%, 95%, 96%, 97%, 98%, 99% or 100% sequence identity, to miRBase Accession No. MI0000446. In varying embodiments, the pre-miRNA-1291 comprises a nucleic acid sequence having at least 90% sequence identity, e.g., at least 91%, 92%, 93%, 94%, 95%, 96%, 97%, 98%, 99% or 100% sequence identity, to SEQ ID NO:12. In varying embodiments, the pre-miRNA-34a comprises a nucleic acid sequence having at least 90% sequence identity, e.g., at least 91%, 92%, 93%, 94%, 95%, 96%, 97%, 98%, 99% or 100% sequence identity, to SEQ ID NO:2. In varying embodiments, the pre-miRNA-125-1 comprises a nucleic acid sequence having at least 90% sequence identity, e.g., at least 91%, 92%, 93%, 94%, 95%, 96%, 97%, 98%, 99% or 100% sequence identity, to SEQ ID NO:14. In varying embodiments, the polynucleotide comprises a methionyl tRNA operably linked to a pre-miRNA-1291. In varying embodiments, the polynucleotide comprises a methionyl tRNA operably linked to a pre-miRNA-34a. In varying embodiments, the polynucleotide comprises a methionyl tRNA operably linked to a pre-miRNA-125-1. In varying embodiments, the methionyl tRNA operably linked to the pre-miRNA-1291 has a nucleic acid sequence having at least 90% sequence identity, e.g., at least 91%, 92%, 93%, 94%, 95%, 96%, 97%, 98%, 99% or 100% sequence identity, to SEQ ID NO:13. In varying embodiments, the methionyl tRNA operably linked to the pre-miRNA-34a has a nucleic acid sequence having at least 90% sequence identity, e.g., at least 91%, 92%, 93%, 94%, 95%, 96%, 97%, 98%, 99% or 100% sequence identity, to SEQ ID NO:3. In varying embodiments, the methionyl tRNA operably linked to the pre-miRNA-125-1 has a nucleic acid sequence having at least 90% sequence identity, e.g., at least 91%, 92%, 93%, 94%, 95%, 96%, 97%, 98%, 99% or 100% sequence identity, to SEQ ID NO:15. In varying embodiments, the tRNA operably linked to a pre-microRNA (pre-miRNA) comprises a polynucleotide sequence having at least about 90% sequence identity, e.g., at least 91%, 92%, 93%, 94%, 95%, 96%, 97%, 98%, 99% or 100% sequence identity, to a polynucleotide selected from the group consisting of SEQ ID NO:3, SEQ ID NO:4, SEQ ID NO:5, SEQ ID NO:6, SEQ ID NO:7, SEQ ID NO:8, SEQ ID NO:13 and SEQ ID NO:15. In varying embodiments, all or part of the stem-loop anticodon of the tRNA is replaced with the pre-miRNA. In some embodiments, the aptamer binds to a dye selected from the group consisting of malachite green, tetramethylrosamine, sulforhodamine B, and triphenylmethane dyes. In some embodiments, the aptamer binds to malachite green. In some embodiments, the aptamer comprises a polynucleotide sequence having at least about 90% sequence identity, e.g., at least 91%, 92%, 93%, 94%, 95%, 96%, 97%, 98%, 99% or 100% sequence identity, to SEQ ID NO:9. In some embodiments, the aptamer is inserted or located 5' to the pre-miRNA. In some embodiments, the aptamer is inserted or located 3' to the pre-miRNA. In some embodiments, the tRNA operably linked to the pre-microRNA (pre-miRNA) and the aptamer comprises a polynucleotide sequence having at least about 90% sequence identity, e.g., at least 91%, 92%, 93%, 94%, 95%, 96%, 97%, 98%, 99% or 100% sequence identity, to SEQ ID NO:10. In some embodiments, the tRNA operably linked to the pre-microRNA (pre-miRNA) and the aptamer comprises a polynucleotide sequence having at least about 90% sequence identity, e.g., at least 91%, 92%, 93%, 94%, 95%, 96%, 97%, 98%, 99% or 100% sequence identity, to SEQ ID NO:11.

In a further aspect, provided are compositions comprising a polynucleotide as described above and herein, and an analyte bound by the aptamer. In varying embodiments, the analyte bound by the aptamer elicits a detectable signal, e.g., a fluorescent signal.

In a further aspect, provided are kits comprising a polynucleotide and/or a composition as described above and herein.

In another aspect, provided are methods of detecting RNase activity. In some embodiments, the methods comprise:
a) contacting a test sample suspected of having RNase with a composition as described above and herein to form a mixture, wherein the analyte bound by the aptamer elicits a detectable signal;
b) determining the presence and amount of detectable signal in the mixture in comparison to the presence and amount of detectable signal in a control composition that has not been contacted with the sample, wherein reduced or eliminated levels of detectable signal indicate the presence of RNase activity. In some embodiments, the test sample is a biological sample. In some embodiments, the biological sample is a fluid sample selected from the group consisting of serum, blood, plasma, saliva, sweat, tears, milk, semen, urine, and vaginal secretions. In some embodiments, the biological sample is a biopsy. In some embodiments, the RNase is one or more ribonucleases selected from the group consisting of RNAse A (RNase 1), RNase H, RNase III, RNase P, RNase L, RNase T1, RNase T2, RNase U2, and angiogenin (RNase 5). In some embodiments, the RNase activity can be detected and quantified at the milligram level without prior dilution of test sample.

Definitions

Unless defined otherwise, all technical and scientific terms used herein generally have the same meaning as commonly understood by one of ordinary skill in the art to which this invention belongs. Generally, the nomenclature used herein and the laboratory procedures in cell culture, molecular genetics, organic chemistry and nucleic acid chemistry and hybridization described below are those well-known and commonly employed in the art. Standard techniques are used for nucleic acid and peptide synthesis. Generally, enzymatic reactions and purification steps are performed according to the manufacturer's specifications. The techniques and procedures are generally performed according to conventional methods in the art and various general references (see generally, Sambrook et al. Molecular Cloning: A Laboratory Manual, 4th ed., Cold Spring Harbor Laboratory Press, Cold Spring Harbor, N.Y. (2012) and Ausubel, ed., Current Protocols in Molecular Biology, John Wiley Interscience, (1990-2014)), which are provided throughout this document. The nomenclature used herein and the laboratory procedures in analytical chemistry, and organic synthetic described below are those well-known and commonly employed in the art. Standard techniques, or modifications thereof, are used for chemical syntheses and chemical analyses.

The term "polynucleotide" refers to polymers composed of deoxyribonucleotides, ribonucleotides or any combination thereof.

As used herein, the term "nucleotide" refers to a chemical moiety having a sugar (modified, unmodified, or an analog thereof), a nucleotide base (modified, unmodified, or an analog thereof), and a phosphate group (modified, unmodified, or an analog thereof). Nucleotides include deoxyribonucleotides, ribonucleotides, and modified nucleotide analogs including, for example, locked nucleic acids ("LNAs"), peptide nucleic acids ("PNAs"), L-nucleotides, ethylene-bridged nucleic acids ("EN As"), arabinoside, and nucleotide analogs (including abasic nucleotides). Similarly, "nucleic acid," "nucleotide sequence," or "nucleic acid sequence" refer to a nucleotide, oligonucleotide, polynucleotide, or any fragment thereof and to naturally occurring or synthetic molecules. These phrases also refer to DNA or RNA of genomic or synthetic origin which may be single-stranded or double-stranded and may represent the sense or the antisense strand, or to any DNA-like or RNA-like material. RNA may be used in the methods described herein and/or may be converted to cDNA by reverse-transcription and/or RNA for use in the methods described herein.

As used herein interchangeably, a "microRNA," "miR," or "miRNA" refer to the unprocessed or processed RNA transcript from a miRNA gene. The unprocessed miRNA gene transcript is also called a "miRNA precursor," and typically comprises an RNA transcript of about 70-100 nucleotides in length. The miRNA precursor can be processed by digestion with an RNase (for example, Dicer, Argonaut, or RNase III) into an active 19-25 nucleotide RNA molecule. This active 19-25 nucleotide RNA molecule is also called the "processed" miRNA gene transcript or "mature" miRNA.

The terms "pre-microRNA" or "pre-miR" or pre-miRNA" interchangeably refer to an RNA hairpin comprising within its polynucleotide sequence at least one mature micro RNA sequence and at least one dicer cleavable site.

The terms "pre-miRNA-1291" or "hsa-mir-1291" or "HGNC:MIR1291" interchangeable refer to an RNA polynucleotide having at least 90% sequence identity, e.g., at least 91%, 92%, 93%, 94%, 95%, 96%, 97%, 98%, 99% or 100% sequence identity, to miRBase Accession No. MI0006353 (www.mirbase.org) or SEQ ID NO:4.

The terms "pre-miRNA-34a" or "hsa-mir-34a" or "HGNC:MIR34A" interchangeable refer to an RNA polynucleotide having at least 90% sequence identity, e.g., at least 91%, 92%, 93%, 94%, 95%, 96%, 97%, 98%, 99% or 100% sequence identity, to miRBase Accession No. MI0000268 (www.mirbase.org) or SEQ ID NO:2.

The terms "pre-miRNA-125-1" or "hsa-mir-125b-1" or "HGNC:MIR125B1" interchangeable refer to an RNA polynucleotide having at least 90% sequence identity, e.g., at least 91%, 92%, 93%, 94%, 95%, 96%, 97%, 98%, 99% or 100% sequence identity, to miRBase Accession No. MI0000446 (www.mirbase.org) or SEQ ID NO:6.

The terms "identical" or percent "identity," in the context of two or more nucleic acids or polypeptide sequences, refer to two or more sequences or subsequences that are the same or have a specified percentage of amino acid residues or nucleotides that are the same (i.e., share at least about 80% identity, for example, at least about 85%, 90%, 91%, 92%, 93%, 94%, 95%, 96%, 97%, 98%, 99% identity over a specified region to a reference sequence, e.g., the tRNA, pre-microRNA and tRNA/microRNA hybrid polynucleotide molecules described herein, when compared and aligned for maximum correspondence over a comparison window, or designated region as measured using a sequence comparison algorithms (e.g., BLAST, ALIGN, FASTA or any other known alignment algorithm) or by manual alignment and visual inspection. Such sequences are then said to be "substantially identical." This definition also refers to the compliment of a test sequence. Preferably, the identity exists over a region that is at least about 10, 15, 20, 25, 35, 40, 45, 50, 60, 70, 80, 90, 100, 110, 120 nucleotides in length, or over the full-length of a reference sequence.

As used herein, the term "short interfering nucleic acid" or "siRNA" refers to any nucleic acid molecule capable of down regulating {i.e., inhibiting) gene expression in a mammalian cells (preferably a human cell). siRNA includes without limitation nucleic acid molecules that are capable of mediating sequence specific RNAi, for example short interfering RNA (siRNA), double-stranded RNA (dsRNA), micro-RNA (miRNA), and short hairpin RNA (shRNA). Likewise, the term "sense region" refers to a nucleotide sequence of a siRNA molecule complementary (partially or fully) to an antisense region of the siRNA molecule. Optionally, the sense strand of a siRNA molecule may also include additional nucleotides not complementary to the antisense region of the siRNA molecule. Conversely, as used herein, the term "antisense region" refers to a nucleotide sequence of a siRNA molecule complementary (partially or fully) to a target nucleic acid sequence. Optionally, the antisense strand of a siRNA molecule may include additional nucleotides not complementary to the sense region of the siRNA molecule.

The terms "piRNA" and "Piwi-interacting RNA" are interchangeable and refer to a class of small RNAs involved in gene silencing. PiRNA molecules typically are between 26 and 31 nucleotides in length.

The terms "snRNA" and "small nuclear RNA" are interchangeable and refer to a class of small RNAs involved in a variety of processes including RNA splicing and regulation of transcription factors. The subclass of small nucleolar RNAs (snoRNAs) is also included. The term is also intended to include artificial snRNAs, such as antisense derivatives of snRNAs comprising antisense sequences directed against the ncRNA.

"Operably linked" refers to an arrangement of elements wherein the components so described are configured so as to perform their usual function. Thus, a given promoter operably linked to a coding sequence is capable of effecting the expression of the coding sequence when the proper enzymes are present. Expression is meant to include the transcription of any one or more of transcription of a microRNA, siRNA, piRNA, snRNA, lncRNA, antisense nucleic acid, or mRNA from a DNA or RNA template and can further include translation of a protein from an mRNA template. The promoter need not be contiguous with the coding sequence, so long as it functions to direct the expression thereof. Thus, for example, intervening untranslated yet transcribed sequences can be present between the promoter sequence and the coding sequence and the promoter sequence can still be considered "operably linked" to the coding sequence.

The term "homologous region" refers to a region of a nucleic acid with homology to another nucleic acid region. Thus, whether a "homologous region" is present in a nucleic acid molecule is determined with reference to another nucleic acid region in the same or a different molecule. Further, since a nucleic acid is often double-stranded, the term "homologous, region," as used herein, refers to the ability of nucleic acid molecules to hybridize to each other. For example, a single-stranded nucleic acid molecule can have two homologous regions which are capable of hybridizing to each other. Thus, the term "homologous region" includes nucleic acid segments with complementary sequence. Homologous regions may vary in length, but will typically be between 4 and 40 nucleotides (e.g., from about 4 to about 40, from about 5 to about 40, from about 5 to about 35, from about 5 to about 30, from about 5 to about 20, from about 6 to about 30, from about 6 to about 25, from about 6 to about 15, from about 7 to about 18, from about 8 to about 20, from about 8 to about 15, etc.).

The term "complementary" and "complementarity" are interchangeable and refer to the ability of polynucleotides to form base pairs with one another. Base pairs are typically formed by hydrogen bonds between nucleotide units in antiparallel polynucleotide strands or regions. Complementary polynucleotide strands or regions can base pair in the Watson-Crick manner (e.g., A to T, A to U, C to G). 100% complementary refers to the situation in which each nucleotide unit of one polynucleotide strand or region can hydrogen bond with each nucleotide unit of a second polynucleotide strand or region. Less than perfect complementarity refers to the situation in which some, but not all, nucleotide units of two strands or two regions can hydrogen bond with each other and can be expressed as a percentage.

A "target site" or "target sequence" is the nucleic acid sequence recognized (i.e., sufficiently complementary for hybridization) by an antisense oligonucleotide or inhibitory RNA molecule.

As used herein, the term "subject" refers to a mammal, such as a human, but can also be another animal such as a domestic animal (e.g., a dog, cat, or the like), a farm animal (e.g., a cow, a sheep, a pig, a horse, or the like) or a laboratory animal (e.g., a monkey, a rat, a mouse, a rabbit, a guinea pig, or the like). The term "patient" refers to a subject who is, or is suspected to be, afflicted with a disease.

As used herein, the terms "effective amount" or "pharmaceutically effective amount" or "therapeutically effective amount" of a composition, is a quantity sufficient to achieve a desired therapeutic and/or prophylactic effect, e.g., an amount which results in the prevention of, or a decrease in, the symptoms associated with a disease that is being treated. The amount of a composition of the invention administered to the subject will depend on the type and severity of the disease and on the characteristics of the individual, such as general health, age, sex, body weight and tolerance to drugs. It will also depend on the degree, severity and type of disease. The skilled artisan will be able to determine appropriate dosages depending on these and other factors. The compositions of the present invention can also be administered in combination with one or more additional therapeutic compounds.

BRIEF DESCRIPTION OF THE DRAWINGS

FIG. 2C discloses SEQ ID NOS 67-78 and FIG. 2D discloses SEQ ID NOS 79, 85, 79-82, 77, 73-74 and 83 respectively, in order of appearance.

DETAILED DESCRIPTION

1. Introduction

Figure 1:
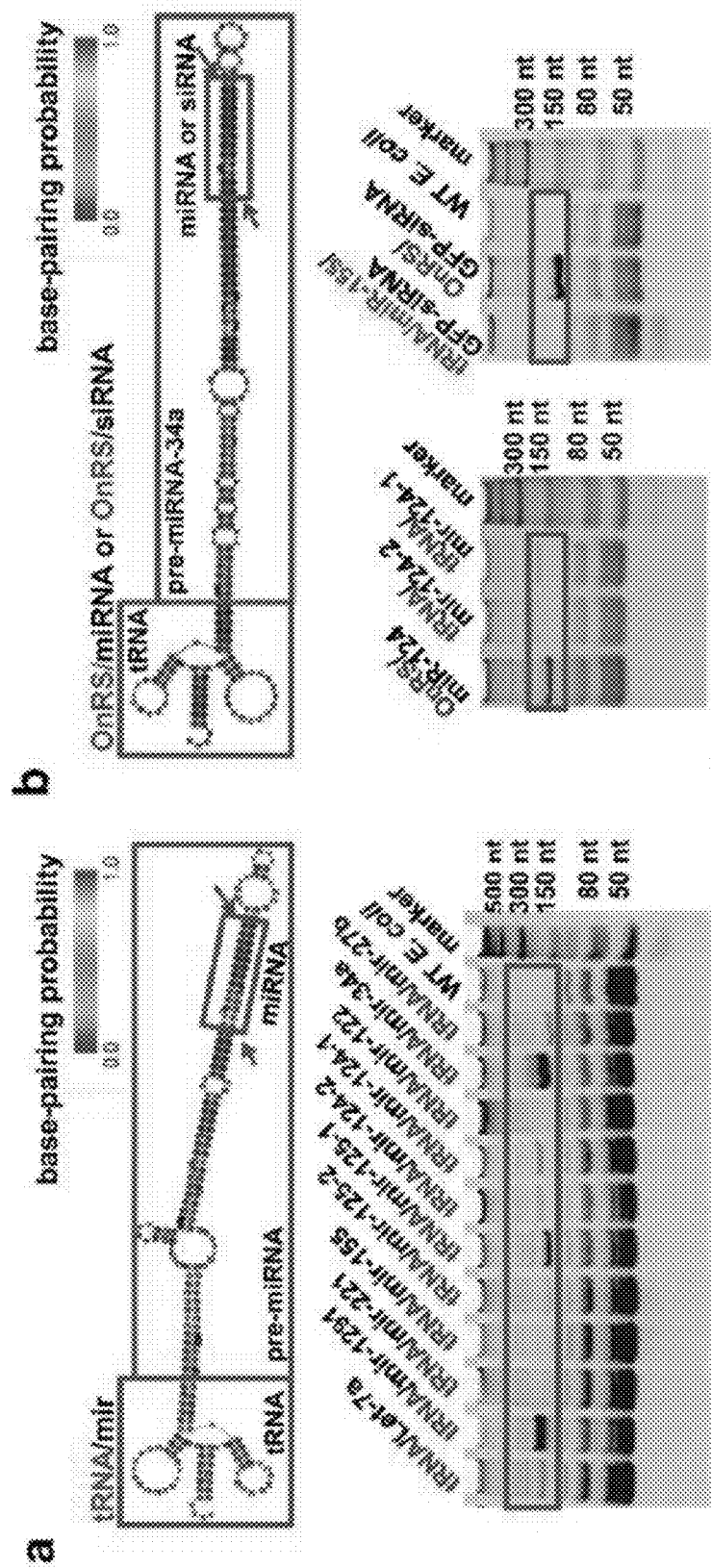
FIG. 1 illustrates high-yield production of recombinant miRNA/siRNA agents in *E. coli* using OnRS-based technology. (a) Urea-PAGE analysis of total RNAs showed that there was large variability in the expression of chimeric pre-miRNAs in *E. coli* using the same tRNA scaffold (SEQ ID NO: 66). Total RNAs isolated from untransformed HST08 (WT) *E. coli* were used as a control. The heat color gradation indicates the base-pairing probability from 0 to 1. (b) The chimeric tRNA/mir-34a (SEQ ID NO: 66) robustly expressed in *E. coli* was developed as an OnRS that offered a consistent high-level expression of chimeric miRNAs (e.g., OnRS/miR-124) and siRNAs (e.g., OnRS/GFP-siRNA) in *E. coli* (e.g., ~15-20% of total RNAs). In contrast, there was no or minimal expression of miR-124 and GFP siRNA using the tRNA and tRNA/mir-155 scaffold, respectively. (c and d) Representative FPLC traces during the purification of OnRS/miR-124 and OnRS/GFP-siRNA, respectively. Inserts are corresponding urea-PAGE analyses of collected fractions (1, 2, 3, and 4) eluted at 8.3 and 8.7 min, respectively, which confirmed the purity of isolated recombinant ncRNAs.
Figure 1:
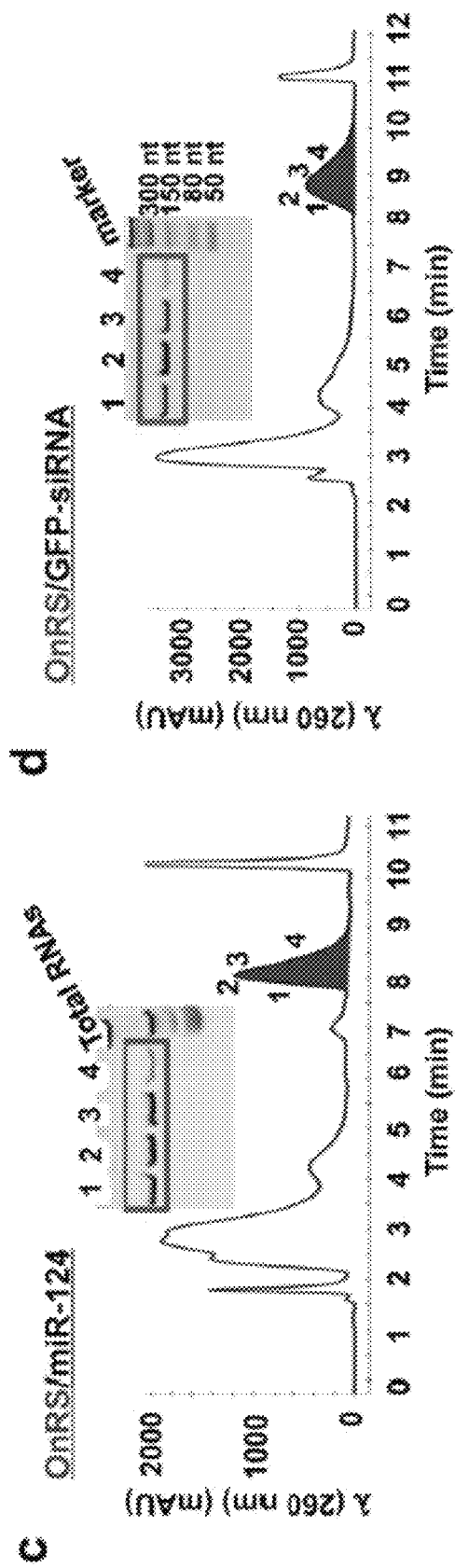

Provided are methods and kits based in part on the discover, design and development of simple methods for producing and using an RNA sensor to detect RNase activity in biological samples. This method is based on the strong and specific fluorescence intensity displayed by malachite green (MG) upon binding to malachite green aptamer (MGA), where chimeric MGA was efficiently produced on large scale (tens of milligrams from 1 L bacterial culture) using tRNA/pre-miRNA non-coding RNA (ncRNA) scaffolds (OnRS) described herein and in co-pending and co-owned U.S. Provisional Application No. 62/003,806, filed on Mar. 28, 2014, also published in Chen, et al., Nucleic Acids Research (2015) 1:doi: 10.1093/nar/gkv228. Both documents are hereby incorporated herein by reference in their entireties for all purposes.

The present RNase detection methods are different from current RNase activity assays, such as those commercially-available kits that rely on isotope- or fluorophore-labeled RNAs that are only able to offer microgram quantities of labeled RNA agents but unable to offer milligrams quantities. Because biological samples such as human sera are comprised of high levels of RNase activities, direct determination of these RNase activities requires the use of large quantities (e.g., microgram levels) of labeled RNA agents which is costly and impractical with presently available technologies. Furthermore, the extensive dilution (e.g., 1:1,000) of serum sample would affect the RNase activity assay including linear range and accuracy. Therefore, the herein described label-free method is much simpler and provides direct, selective and accurate measurement of RNase activity in human serum samples, etc. Data are provided to demonstrate the utility of this method to detect serum RNase activities, e.g., in pancreatic cancer patients versus healthy/benign subjects, and thereof may be utilized for diagnosis and/or prognosis.

The presently described fluorescence-based method uses label-free RNA substrate bearing a malachite green aptamer (MGA), which produces a selective and sensitive fluorescent absorbance upon binding to malachite green MG. Chimeric MGA is produced on a large scale using tRNA/pre-miRNA non-coding RNA (ncRNA) scaffolds (OnRS) recombinant RNA technique (e.g., producing multi-milligrams MGA from 1 L bacterial culture), thereby allowing the assay of serum RNase activity without dilution. This method is cost-effective, selective and more accurate.

2. Polynucleotides—tRNA/Pre-microRNA Scaffolds

Generally, the polynucleotides comprise a tRNA operably linked to a pre-microRNA. In varying embodiments, the anticodon of the tRNA is replaced with a pre-microRNA molecule. For example, in some embodiments, the 3'-terminus and the 5'-terminus of the pre-microRNA are ligated or fused to the 3'-terminus and the 5'-terminus of the tRNA that are created when the anticodon is removed. The tRNA molecule and the pre-microRNA molecule can be, but need not be directly ligated or fused to one another to be operably linked. In varying embodiments, the pre-microRNA can contain one or more dicer cleavable sites to allow for the high level expression and efficient cleavage of an inserted RNA molecule desired to be expressed from the hybrid tRNA/pre-microRNA polynucleotide.

The hybrid tRNA/pre-microRNA molecules can be produced by standard recombinant methods, or can be synthetically prepared. In varying embodiments, the polynucleotides can have one or more chemical modifications, including without limitation, e.g., internucleotide linkages, internucleotide linkages, dideoxyribonucleotides, 2'-sugar modification, 2'-amino groups, 2'-fluoro groups, 2'-methoxy groups, 2'-alkoxy groups, 2'-alkyl groups, 2'-deoxyribonucleotides, 2'-O-methyl ribonucleotides, 2'-deoxy-2'-fluoro ribonucleotides, universal base nucleotides, acyclic nucleotides, 5-C-methyl nucleotides, biotin groups, terminal glyceryl incorporation, inverted deoxy abasic residue incorporation, sterically hindered molecules, 3'-deoxyadenosine (cordycepin), 3'-azido-3'-deoxythymidine (AZT), 2',3'-dideoxyinosine (ddI), 2',3'-dideoxy-3'-thiacytidine (3TC), 2',3'-didehydro-2',3'-dideoxythymidi-ne (d4T), monophosphate nucleotide modification (MNM) of 3'-azido-3'-deoxythymidine (AZT), MNM-2',3'-dideoxy-3'-thiacytidine (3TC), MNM-2',3'-didehydro-2',3'-dide-oxythymidine (d4T), capping moieties, L-nucleotides locked nucleic acid (LNA) nucleotides, 2'-methoxyethoxy (MOE) nucleotides, 2'-methyl-thio-ethyl, 2'-deoxy-2'-fluoro nucleotides, 2'-deoxy-2'-chloro nucleotides, 2'-azido nucleotides, 2'-0-methyl, cholesterol groups, 2'-O-methyl groups, phosphorothioate groups, 2'-fluoro groups, 2'-0-methyoxyethyl groups, boranophosphate groups, 4'-thioribose groups, bile acid, lipids, and bridges connecting the 2'-oxygen and 4'-carbon.

In varying embodiments, the hybrid tRNA/pre-microRNA molecules comprise analog ribonucleotide bases. As used herein, the term "analog" defines possible derivatives of the ribonucleotide originating from the activity of tRNA post-transcriptional modification enzymes of the cell in which they are produced. The analogs of the ribonucleotides A, C, G and U which may be found in a tRNA depend on the cell in which that tRNA is produced and on the position of the ribonucleotide in question in the tRNA. A large number of analogs are given in Sprinzl et al. (1998) "Compilation of tRNA sequences and sequences of tRNA genes". Nucleic Acids Res., 26, 148-153 and on the basis of "RNA modification database" data (medstat.med.utah.edu/RNAmods/). The analogs of A may be selected more particularly from the group constituted by 1-methyl-A, inosine and 2'-O-methyl-A. The analogs of C may be selected more particularly from the group constituted by 5-methyl-C and 2'-O-methyl-C. The analogs of G may be selected more particularly from the group constituted by 7-methyl-G and 2'-O-methyl-G. The analogs of U may be selected more particularly from the group constituted by pseudouridine, ribothymidine, 2'-O-methyl-ribothymidine, dihydrouridine, 4-thiouridine and 3-(3-amino-3-carboxypropyl)-uridine.

a. tRNA

The general characteristics of a tRNA are well-known to the person skilled in the art. In some embodiments, a tRNA is formed of a single ribonucleotide chain which is capable of folding to adopt a characteristic, so-called cloverleaf secondary structure. This characteristic secondary structure comprises:

(i) an acceptor stem composed of the first 7 ribonucleotides of the 5' end of the ribonucleotide chain and the 7 ribonucleotides that precede the last 4 ribonucleotides of the 3' end of the ribonucleotide chain, thus forming a double-stranded structure comprising 6 or 7 pairs of ribonucleotides, it being possible for the ribonucleotides constituted by the first ribonucleotide of the 5' end of the ribonucleotide chain and the ribonucleotide that precedes the last 4 ribonucleotides of the 3' end of the ribonucleotide chain not to be paired;

(ii) a D arm constituted by 4 pairs of ribonucleotides and a D loop constituted by 8 to 10 ribonucleotides, formed by the folding of a part of the ribonucleotide chain that follows the first 7 ribonucleotides of the 5' end of the ribonucleotide chain;

(iii) a stem of the anticodon constituted by 5 pairs of ribonucleotides, and a loop of the anticodon constituted by 7 ribonucleotides (stem-loop of the anticodon), formed by the folding of a part of the ribonucleotide chain that follows the D arm and the D loop;

(iv) a variable loop constituted by from 4 to 21 ribonucleotides and formed by a part of the ribonucleotide chain that follows the stem of the anticodon and the loop of the anticodon;

(v) a T arm constituted by 5 pairs of ribonucleotides, and a T loop constituted by 8 ribonucleotides, formed by the folding of a part of the ribonucleotide chain that follows the variable loop and precedes the ribonucleotides of the 3' end of the ribonucleotide chain which are involved in the constitution of the acceptor stem.

The hybrid tRNA/pre-microRNA polynucleotides can contain any tRNA known in the art, e.g. for encoding any amino acid. The selection of an appropriate tRNA molecule may be, in part, driven by the host cells to be used for expression of the inserted RNA. For example, when seeking to produce high expression levels of a desired inserted RNA molecule, the tRNA selected can be from a tRNA encoding for codon preferred by the species of host cell rather than from a rare codon in that species of host cell. In varying embodiments, the tRNA is a methionyl-tRNA. In varying embodiments, the tRNA is derived from the host cell used for expression. In varying embodiments, the tRNA is a mammalian tRNA. In varying embodiments, the tRNA is a human tRNA.

In some embodiments, the chimeric tRNA defined above does not comprise the substantially intact stem of the anticodon of the tRNA from which it is derived. For example, in the chimeric tRNA, between the ribonucleotide that precedes the stem-loop of the anticodon in the tRNA before modification and the ribonucleotide that follows the stem-loop of the anticodon in the tRNA before modification, the stem of the anticodon of the tRNA before modification is no longer present.

b. Pre-microRNA

The hybrid tRNA/pre-microRNA polynucleotides can contain any pre-microRNA molecule known in the art. In varying embodiments the pre-microRNA is selected from human pre-miRNA-1291, human pre-miRNA-34a and human pre-miRNA-125-1. Other pre-microRNA molecules that can be used in the hybrid tRNA/pre-microRNA polynucleotides include pre-microRNA molecules that express in the host cell (e.g., E. coli host cell) at or above the levels of expression of human pre-miRNA-1291, human pre-miRNA-34a and human pre-miRNA-125-1 in the same host cell (e.g., E. coli host cell). In varying embodiments, the pre-microRNA molecule is from a mammalian pre-microRNA molecule. In varying embodiments, the pre-microRNA molecule is from a human pre-microRNA molecule. In varying embodiments, the pre-microRNA component of the hybrid tRNA/pre-microRNA polynucleotides is from about 80 nucleotides to about 120 nucleotides in length, e.g., from about 80 nucleotides to about 100 nucleotides in length, e.g., about 80, 85, 90, 95, 100, 105, 110, 115 or 120 nucleotides in length.

In varying embodiments, the pre-microRNA is a human pre-microRNA selected from the group consisting of hsa-let-7a-1 (miRBase.org accession no.: MI0000060), hsa-let-7a-2 (MI0000061), hsa-let-7a-3 (MI0000062), hsa-let-7b (MI0000063), hsa-let-7c (MI0000064), hsa-let-7d (MI0000065), hsa-let-7e (MI0000066), hsa-let-7f-1 (MI0000067), hsa-let-7f-2 (MI0000068), hsa-let-7g (MI0000433), hsa-let-7i (MI0000434), hsa-mir-1-1 (MI0000651), hsa-mir-1-2 (MI0000437), hsa-mir-7-1 (MI0000263), hsa-mir-7-2 (MI0000264), hsa-mir-7-3 (MI0000265), hsa-mir-9-1 (MI0000466), hsa-mir-9-2 (MI0000467), hsa-mir-9-3 (MI0000468), hsa-mir-10a (MI0000266), hsa-mir-10b (MI0000267), hsa-mir-15a (MI0000069), hsa-mir-15b (MI0000438), hsa-mir-16-1 (MI0000070), hsa-mir-16-2 (MI0000115), hsa-mir-17 (MI0000071), hsa-mir-18a (MI0000072), hsa-mir-18b (MI0001518), hsa-mir-19a (MI0000073), hsa-mir-19b-1 (MI0000074), hsa-mir-19b-2 (MI0000075), hsa-mir-20a (MI0000076), hsa-mir-20b (MI0001519), hsa-mir-21 (MI0000077), hsa-mir-22 (MI0000078), hsa-mir-23a (MI0000079), hsa-mir-23b (MI0000439), hsa-mir-23c (MI0016010), hsa-mir-24-1 (MI0000080), hsa-mir-24-2 (MI0000081), hsa-mir-25 (MI0000082), hsa-mir-26a-1 (MI0000083), hsa-mir-26a-2 (MI0000750), hsa-mir-26b (MI0000084), hsa-mir-27a (MI0000085), hsa-mir-27b (MI0000440), hsa-mir-28 (MI0000086), hsa-mir-29a (MI0000087), hsa-mir-29b-1 (MI0000105), hsa-mir-29b-2 (MI0000107), hsa-mir-29c (MI0000735), hsa-mir-30a (MI0000088), hsa-mir-30b (MI0000441), hsa-mir-30c-1 (MI0000736), hsa-mir-30c-2 (MI0000254), hsa-mir-30d (MI0000255), hsa-mir-30e (MI0000749), hsa-mir-31 (MI0000089), hsa-mir-32 (MI0000090), hsa-mir-33a (MI0000091), hsa-mir-33b (MI0003646), hsa-mir-34a (MI0000268), hsa-mir-34b (MI0000742), hsa-mir-34c (MI0000743), hsa-mir-92a-1 (MI0000093), hsa-mir-92a-2 (MI0000094), hsa-mir-92b (MI0003560), hsa-mir-93 (MI0000095), hsa-mir-95 (MI0000097), hsa-mir-96 (MI0000098), hsa-mir-98 (MI0000100), hsa-mir-99a (MI0000101), hsa-mir-99b (MI0000746), hsa-mir-100 (MI0000102), hsa-mir-101-1 (MI0000103), hsa-mir-101-2 (MI0000739), hsa-mir-103a-1 (MI0000109), hsa-mir-103a-2 (MI0000108), hsa-mir-103b-1 (MI0007261), hsa-mir-103b-2 (MI0007262), hsa-mir-105-1 (MI0000111), hsa-mir-105-2 (MI0000112), hsa-mir-106a (MI0000113), hsa-mir-106b (MI0000734), hsa-mir-107 (MI0000114), hsa-mir-122 (MI0000442), hsa-mir-124-1 (MI0000443), hsa-mir-124-2 (MI0000444), hsa-mir-124-3 (MI0000445), hsa-mir-125a (MI0000469), hsa-mir-125b-1 (MI0000446), hsa-mir-125b-2 (MI0000470), hsa-mir-126 (MI0000471), hsa-mir-127 (MI0000472), hsa-mir-128-1 (MI0000447), hsa-mir-128-2 (MI0000727), hsa-mir-129-1 (MI0000252), hsa-mir-129-2 (MI0000473), hsa-mir-130a (MI0000448), hsa-mir-130b (MI0000748), hsa-mir-132 (MI0000449), hsa-mir-133a-1 (MI000045), hsa-mir-133a-2 (MI0000451), hsa-mir-133b (MI0000822), hsa-mir-134 (MI0000474), hsa-mir-135a-1 (MI0000452), hsa-mir-135a-2 (MI0000453), hsa-mir-135b (MI0000810), hsa-mir-136 (MI0000475), hsa-mir-137 (MI0000454), hsa-mir-138-1 (MI0000476), hsa-mir-138-2 (MI0000455), hsa-mir-139 (MI0000261), hsa-mir-140 (MI0000456), hsa-mir-141 (MI0000457), hsa-mir-142 (MI0000458), hsa-mir-143 (MI0000459), hsa-mir-144 (MI0000460), hsa-mir-145 (MI0000461), hsa-mir-146a (MI0000477), hsa-mir-146b (MI0003129), hsa-mir-147a (MI0000262), hsa-mir-147b (MI0005544), hsa-mir-148a (MI0000253), hsa-mir-148b (MI0000811), hsa-mir-149 (MI0000478), hsa-mir-150 (MI0000479), hsa-mir-151a (MI0000809), hsa-mir-151b (MI0003772), hsa-mir-152 (MI0000462), hsa-mir-153-1 (MI0000463), hsa-mir-153-2 (MI0000464), hsa-mir-154 (MI0000480), hsa-mir-155 (MI0000681), hsa-mir-181a-1 (MI0000289), hsa-mir-181a-2 (MI0000269), hsa-mir-181b-1 (MI0000270), hsa-mir-181b-2 (MI0000683), hsa-mir-181c (MI0000271), hsa-mir-181d (MI0003139), hsa-mir-182 (MI0000272), hsa-mir-183 (MI0000273), hsa-mir-184 (MI0000481), hsa-mir-185 (MI0000482), hsa-mir-186 (MI0000483), hsa-mir-187 (MI0000274), hsa-mir-188 (MI0000484), hsa-mir-190a (MI0000486), hsa-mir-190b (MI0005545), hsa-mir-191 (MI0000465), hsa-mir-192 (MI0000234), hsa-mir-193a (MI0000487), hsa-mir-193b (MI0003137), hsa-mir-194-1 (MI0000488), hsa-mir-194-2 (MI0000732), hsa-mir-195 (MI0000489), hsa-mir-196a-1 (MI0000238), hsa-mir-196a-2 (MI0000279), hsa-mir-196b (MI0001150), hsa-mir-197 (MI0000239), hsa-mir-198 (MI0000240), hsa-mir-199a-1 (MI0000242), hsa-mir-199a-2 (MI0000281), hsamir-199b (MI0000282), hsa-mir-200a (MI0000737), hsa-mir-200b (MI0000342), hsa-mir-200c (MI0000650), hsa-mir-202 (MI0003130), hsa-mir-203a (MI0000283), hsa-mir-203b (MI0017343), hsa-mir-204 (MI0000284), hsa-mir-205 (MI0000285), hsa-mir-206 (MI0000490), hsa-mir-208a (MI0000251), hsa-mir-208b (MI0005570), hsa-mir-210 (MI0000286), hsa-mir-211 (MI0000287), hsa-mir-212 (MI0000288), hsa-mir-214 (MI0000290), hsa-mir-215 (MI0000291), hsa-mir-216a (MI0000292), hsa-mir-216b (MI0005569), hsa-mir-217 (MI0000293), hsa-mir-218-1 (MI0000294), hsa-mir-218-2 (MI0000295), hsa-mir-219a-1 (MI0000296), hsa-mir-219a-2 (MI0000740), hsa-mir-219b (MI0017299), hsa-mir-221 (MI0000298), hsa-mir-222 (MI0000299), hsa-mir-223 (MI0000300), hsa-mir-224 (MI0000301), hsa-mir-296 (MI0000747), hsa-mir-297 (MI0005775), hsa-mir-298 (MI0005523), hsa-mir-299 (MI0000744), hsa-mir-300 (MI0005525), hsa-mir-301a (MI0000745), hsa-mir-301b (MI0005568), hsa-mir-302a (MI0000738), hsa-mir-302b (MI0000772), hsa-mir-302c (MI0000773), hsa-mir-302d (MI0000774), hsa-mir-302e (MI0006417), hsa-mir-302f (MI0006418), hsa-mir-320a (MI0000542), hsa-mir-320b-1 (MI0003776), hsa-mir-320b-2 (MI0003839), hsa-mir-320c-1 (MI0003778), hsa-mir-320c-2 (MI0008191), hsa-mir-320d-1 (MI0008190), hsa-mir-320d-2 (MI0008192), hsa-mir-320e (MI0014234), hsa-mir-323a (MI0000807), hsa-mir-323b (MI001420), hsa-mir-324 (MI0000813), hsa-mir-325 (MI0000824), hsa-mir-326 (MI0000808), hsa-mir-328 (MI0000804), hsa-mir-329-1 (MI0001725), hsa-mir-329-2 (MI0001726), hsa-mir-330 (MI0000803), hsa-mir-331 (MI0000812), hsa-mir-335 (MI0000816), hsa-mir-337 (MI0000806), hsa-mir-338 (MI0000814), hsa-mir-339 (MI0000815), hsa-mir-340 (MI0000802), hsa-mir-342 (MI0000805), hsa-mir-345 (MI0000825), hsa-mir-346 (MI0000826), hsa-mir-361 (MI0000760), hsa-mir-362 (MI0000762), hsa-mir-363 (MI000076), hsa-mir-365a (MI0000767), hsa-mir-365b (MI0000769), hsa-mir-367 (MI0000775), hsa-mir-369 (MI0000777), hsa-mir-370 (MI0000778), hsa-mir-371a (MI0000779), hsa-mir-371b (MI0017393), hsa-mir-372 (MI0000780), hsa-mir-373 (MI0000781), hsa-mir-374a (MI0000782), hsa-mir-374b (MI0005566), hsa-mir-374c (MI0016684), hsa-mir-375 (MI0000783), hsa-mir-376a-1 (MI0000784), hsa-mir-376a-2 (MI0003529), hsa-mir-376b (MI0002466), hsa-mir-376c (MI0000776), hsa-mir-377 (MI0000785), hsa-mir-378a (MI0000786), hsa-mir-378b (MI0014154), hsa-mir-378c (MI0015825), hsa-mir-378d-1 (MI0016749), hsa-mir-378d-2 (MI0003840), hsa-mir-378e (MI0016750), hsa-mir-378f (MI0016756), hsa-mir-378g (MI0016761), hsa-mir-378h (MI0016808 803), hsa-mir-378i (MI0016902), hsa-mir-378j (MI0021273), hsa-mir-379 (MI0000787), hsa-mir-380 (MI0000788), hsa-mir-381 (MI0000789), hsa-mir-382 (MI0000790), hsa-mir-383 (MI0000791), hsa-mir-384 (MI0001145), hsa-mir-409 (MI0001735), hsa-mir-410 (MI0002465), hsa-mir-411 (MI0003675), hsa-mir-412 (MI0002464), hsa-mir-421 (MI0003685), hsa-mir-422a (MI0001444), hsa-mir-423 (MI0001445), hsa-mir-424 (MI0001446), hsa-mir-425 (MI0001448), hsa-mir-429 (MI0001641), hsa-mir-431 (MI0001721), hsa-mir-432 (MI0003133), hsa-mir-433 (MI0001723), hsa-mir-448 (MI0001637), hsa-mir-449a (MI0001648), hsa-mir-449b (MI0003673), hsa-mir-449c (MI0003823), hsa-mir-450a-1 (MI0001652), hsa-mir-450a-2 (MI0003187), hsa-mir-450b (MI0005531), hsa-mir-451a (MI0001729), hsa-mir-451b (MI0017360), hsa-mir-452 (MI0001733), hsa-mir-454 (MI0003820), hsa-mir-455 (MI0003513), hsa-mir-466 (MI0014157), hsa-mir-483 (MI0002467), hsa-mir-484 (MI0002468), hsa-mir-485 (MI0002469), hsa-mir-486 (MI0002470), hsa-mir-486-2 (MI0023622), hsa-mir-487a (MI0002471), hsa-mir-487b (MI0003530), hsa-mir-488 (MI0003123), hsa-mir-489 (MI0003124), hsa-mir-490 (MI0003125), hsa-mir-491 (MI0003126), hsa-mir-492 (MI0003131), hsa-mir-493 (MI0003132), hsa-mir-494 (MI0003134), hsa-mir-495 (MI0003135), hsa-mir-496 (MI0003136), hsa-mir-497 (MI0003138), hsa-mir-498 (MI0003142), hsa-mir-499a (MI0003183), hsa-mir-499b (MI0017396), hsa-mir-500a (MI0003184), hsa-mir-500b (MI0015903), hsa-mir-501 (MI0003185), hsa-mir-502 (MI0003186), hsa-mir-503 (MI0003188), hsa-mir-504 (MI0003189), hsa-mir-505 (MI0003190), hsa-mir-506 (MI0003193), hsa-mir-507 (MI0003194), hsa-mir-508 (MI0003195), hsa-mir-509-1 (MI0003196), hsa-mir-509-2 (MI0005530), hsa-mir-509-3 (MI0005717), hsa-mir-510 (MI0003197), hsa-mir-511 (MI0003127), hsa-mir-512-1 (MI0003140), hsa-mir-512-2 (MI0003141), hsa-mir-513a-1 (MI0003191), hsa-mir-513a-2 (MI0003192), hsa-mir-513b (MI0006648), hsa-mir-513c (MI0006649), hsa-mir-514a-1 (MI0003198), hsa-mir-514a-2 (MI0003199), hsa-mir-514a-3 (MI0003200), hsa-mir-514b (MI0014251), hsa-mir-515-1 (MI0003144), hsa-mir-515-2 (MI0003147), hsa-mir-516a-1 (MI0003180), hsa-mir-516a-2 (MI0003181), hsa-mir-516b-1 (MI0003172), hsa-mir-516b-2 (MI0003167), hsa-mir-517a (MI0003161), hsa-mir-517b (MI0003165), hsa-mir-517c (MI0003174), hsa-mir-518a-1 (MI0003170), hsa-mir-518a-2 (MI0003173), hsa-mir-518b (MI0003156), hsa-mir-518c (MI0003159), hsa-mir-518d (MI0003171), hsa-mir-518e (MI0003169), hsa-mir-518f (MI0003154), hsa-mir-519a-1 (MI0003178), hsa-mir-519a-2 (MI0003182), hsa-mir-519b (MI0003151), hsa-mir-519c (MI0003148), hsa-mir-519d (MI0003162), hsa-mir-519e (MI0003145), hsa-mir-520a (MI0003149), hsa-mir-520b (MI0003155), hsa-mir-520c (MI0003158), hsa-mir-520d (MI0003164), hsa-mir-520e (MI0003143), hsa-mir-520f (MI0003146), hsa-mir-520g (MI0003166), hsa-mir-520h (MI0003175), hsa-mir-521-1 (MI0003176), hsa-mir-521-2 (MI0003163), hsa-mir-522 (MI0003177), hsa-mir-523 (MI0003153), hsa-mir-524 (MI0003160), hsa-mir-525 (MI0003152), hsa-mir-526a-1 (MI0003157), hsa-mir-526a-2 (MI0003168), hsa-mir-526b (MI0003150), hsa-mir-527 (MI0003179), hsa-mir-532 (MI0003205), hsa-mir-539 (MI0003514), hsa-mir-541 (MI0005539), hsa-mir-542 (MI0003686), hsa-mir-543 (MI0005565), hsa-mir-544a (MI0003515), hsa-mir-544b (MI0014159), hsa-mir-545 (MI0003516), hsa-mir-548a-1 (MI0003593. hsa-mir-548a-2 (MI0000359), hsa-mir-548a-3 (MI0003612), hsa-mir-548aa-1 (MI0016689), hsa-mir-548aa-2 (MI0016690), hsa-mir-548ab (MI0016752), hsa-mir-548ac (MI0016762), hsa-mir-548ad (MI0016770), hsa-mir-548ae-1 (MI0016779), hsa-mir-548ae-2 (MI0016780), hsa-mir-548ag-1 (MI0016793), hsa-mir-548ag-2 (MI0016794), hsa-mir-548ah (MI0016796), hsa-mir-548ai (MI0016813), hsa-mir-548aj-1 (MI0016814), hsa-mir-548aj-2 (MI0016815), hsa-mir-548ak (MI0016840), hsa-mir-548al (MI0016851), hsa-mir-548am (MI0016904), hsa-mir-548an (MI0016907), hsa-mir-548ao (MI0017871), hsa-mir-548ap (MI0017875), hsa-mir-548aq (MI0019130), hsa-mir-548ar (MI0019131), hsa-mir-548as (MI0019132), hsa-mir-548at (MI0019137), hsa-mir-548au (MI0019145), hsa-mir-548av (MI0019152), hsa-mir-548aw (MI0019283), hsa-mir-548ax (MI0019286), hsa-mir-548ay (MI0022210), hsa-mir-548az (MI0022212), hsa-mir-548b (MI0003596), hsa-mir-548ba (MI0025747), hsa-mir-548c (MI0003630), hsa-mir-548d-1 (MI0003668), hsa-mir-548d-2 (MI0003671), hsa-mir-548e (MI0006344), hsa-mir-548f-1 (MI0006374), hsa-mir-548f-2 (MI0006375), hsa-mir-548f-3 (MI0006376), hsa-mir-548f-4 (MI0006377), hsa-mir-548f-5 (MI0006378), hsa-mir-548g (MI0006395), hsa-mir-548h-1 (MI0006411), hsa-mir-548h-2 (MI0006412), hsa-mir-548h-3 (MI0006413), hsa-mir-548h-4 (MI0006414), hsa-mir-548h-5 (MI0016751), hsa-mir-548i-1 (MI0006421), hsa-mir-548i-2 (MI0006422), hsa-mir-548i-3 (MI0006423), hsa-mir-548i-4 (MI0006424), hsa-mir-548j (MI0006345), hsa-mir-548k (MI0006354), hsa-mir-548l (MI0006361), hsa-mir-548m (MI0006400), hsa-mir-548n (MI0006399), hsa-mir-548o (MI0006402), hsa-mir-548o-2 (MI0016746), hsa-mir-548p (MI0006420), hsa-mir-548q (MI0010637), hsa-mir-548s (MI0014141), hsa-mir-548t (MI0014164), hsa-mir-548u (MI0014168), hsa-mir-548v (MI0014174), hsa-mir-548w (MI0014222), hsa-mir-548x (MI0014244), hsa-mir-548x-2 (MI0016833), hsa-mir-548y (MI0016595), hsa-mir-548z (MI0016688), hsa-mir-549a (MI0003679), hsa-mir-550a-1 (MI0003600), hsa-mir-550a-2 (MI0003601), hsa-mir-550a-3 (MI0003762), hsa-mir-550b-1 (MI0016686), hsa-mir-550b-2 (MI0016687), hsa-mir-551a (MI0003556), hsa-mir-551b (MI0003575), hsa-mir-552 (MI0003557), hsa-mir-553 (MI0003558), hsa-mir-554 (MI0003559), hsa-mir-555 (MI0003561), hsa-mir-556 (MI0003562), hsa-mir-557 (MI0003563), hsa-mir-558 (MI0003564), hsa-mir-559 (MI0003565), hsa-mir-561 (MI0003567), hsa-mir-562 (MI0003568), hsa-mir-563 (MI0003569), hsa-mir-564 (MI0003570), hsa-mir-566 (MI0003572), hsa-mir-567 (MI0003573), hsa-mir-568 (MI0003574), hsa-mir-569 (MI0003576), hsa-mir-570 (MI0003577), hsa-mir-571 (MI0003578), hsa-mir-572 (MI0003579), hsa-mir-573 (MI0003580), hsa-mir-574 (MI0003581), hsa-mir-575 (MI0003582), hsa-mir-576 (MI0003583), hsa-mir-577 (MI0003584), hsa-mir-578 (MI0003585), hsa-mir-579 (MI0003586), hsa-mir-580 (MI0003587), hsa-mir-581 (MI0003588), hsa-mir-582 (MI0003589), hsa-mir-583 (MI0003590), hsa-mir-584 (MI0003591), hsa-mir-585 (MI000359), hsa-mir-586 (MI0003594), hsa-mir-587 (MI0003595), hsa-mir-588 (MI0003597), hsa-mir-589 (MI0003599), hsa-mir-590 (MI0003602), hsa-mir-591 (MI0003603), hsa-mir-592 (MI0003604), hsa-mir-593 (MI0003605), hsa-mir-595 (MI0003607), hsa-mir-596 (MI0003608), hsa-mir-597 (MI0003609), hsa-mir-598 (MI0003610 162), hsa-mir-599 (MI0003611), hsa-mir-600 (MI0003613), hsa-mir-601 (MI0003614), hsa-mir-602 (MI0003615), hsa-mir-603 (MI0003616), hsa-mir-604 (MI0003617), hsa-mir-605 (MI0003618), hsa-mir-606 (MI0003619), hsa-mir-607 (MI0003620), hsa-mir-608 (MI0003621), hsa-mir-609 (MI0003622), hsa-mir-610 (MI0003623), hsa-mir-611 (MI0003624), hsa-mir-612 (MI0003625), hsa-mir-613 (MI0003626), hsa-mir-614 (MI0003627), hsa-mir-615 (MI0003628), hsa-mir-616 (MI0003629), hsa-mir-617 (MI0003631), hsa-mir-618 (MI0003632), hsa-mir-619 (MI0003633), hsa-mir-620 (MI0003634), hsa-mir-621 (MI0003635), hsa-mir-622 (MI0003636), hsa-mir-623 (MI0003637), hsa-mir-624 (MI0003638), hsa-mir-625 (MI0003639), hsa-mir-626 (MI0003640), hsa-mir-627 (MI0003641), hsa-mir-628 (MI0003642), hsa-mir-629 (MI0003643), hsa-mir-630 (MI000364), hsa-mir-631 (MI0003645), hsa-mir-632 (MI0003647), hsa-mir-633 (MI0003648), hsa-mir-634 (MI0003649), hsa-mir-635 (MI0003650), hsa-mir-636 (MI0003651), hsa-mir-637 (MI0003652), hsa-mir-638 (MI0003653), hsa-mir-639 (MI0003654), hsa-mir-640 (MI0003655), hsa-mir-641 (MI0003656), hsa-mir-642a (MI0003657), hsa-mir-642b (MI0016685), hsa-mir-643 (MI0003658), hsa-mir-644a (MI0003659), hsa-mir-645 (MI0003660), hsa-mir-646 (MI0003661), hsa-mir-647 (MI0003662), hsa-mir-648 (MI0003663), hsa-mir-649 (MI0003664), hsa-mir-650 (MI0003665), hsa-mir-651 (MI0003666), hsa-mir-652 (MI0003667), hsa-mir-653 (MI0003674), hsa-mir-654 (MI0003676), hsa-mir-655 (MI0003677), hsa-mir-656 (MI0003678), hsa-mir-657 (MI0003681), hsa-mir-658 (MI0003682), hsa-mir-659 (MI0003683), hsa-mir-660 (MI0003684), hsa-mir-661 (MI0003669), hsa-mir-662 (MI0003670), hsa-mir-663a (MI0003672), hsa-mir-663b (MI0006336), hsa-mir-664a (MI0006442), hsa-mir-664b (MI0019134), hsa-mir-665 (MI0005563), hsa-mir-668 (MI0003761), hsa-mir-670 (MI0003933), hsa-mir-671 (MI0003760), hsa-mir-675 (MI0005416), hsa-mir-676 (MI0016436), hsa-mir-708 (MI0005543), hsa-mir-711 (MI0012488), hsa-mir-718 (MI0012489), hsa-mir-744 (MI0005559), hsa-mir-758 (MI0003757), hsa-mir-759 (MI0004065), hsa-mir-760 (MI0005567), hsa-mir-761 (MI0003941), hsa-mir-762 (MI0003892), hsa-mir-764 (MI0003944), hsa-mir-765 (MI0005116), hsa-mir-766 (MI0003836), hsa-mir-767 (MI0003763), hsa-mir-769 (MI0003834), hsa-mir-770 (MI0005118), hsa-mir-802 (MI0003906), hsa-mir-873 (MI0005564), hsa-mir-874 (MI0005532), hsa-mir-875 (MI0005541), hsa-mir-876 (MI0005542), hsa-mir-877 (MI0005561), hsa-mir-885 (MI0005560), hsa-mir-887 (MI0005562), hsa-mir-888 (MI0005537), hsa-mir-889 (MI0005540), hsa-mir-890 (MI0005533), hsa-mir-891a (MI0005524), hsa-mir-891b (MI0005534), hsa-mir-892a (MI0005528), hsa-mir-892b (MI0005538), hsa-mir-892c (MI0022560), hsa-mir-920 (MI0005712), hsa-mir-921 (MI0005713), hsa-mir-922 (MI0005714), hsa-mir-924 (MI0005716), hsa-mir-933 (MI0005755), hsa-mir-934 (MI0005756), hsa-mir-935 (MI0005757), hsa-mir-936 (MI0005758), hsa-mir-937 (MI0005759), hsa-mir-938 (MI0005760), hsa-mir-939 (MI0005761), hsa-mir-940 (MI0005762), hsa-mir-941-1 (MI0005763), hsa-mir-941-2 (MI0005764), hsa-mir-941-3 (MI0005765), hsa-mir-941-4 (MI0005766), hsa-mir-942 (MI0005767), hsa-mir-943 (MI0005768), hsa-mir-944 (MI0005769), hsa-mir-1178 (MI0006271), hsa-mir-1179 (MI0006272), hsa-mir-1180 (MI0006273), hsa-mir-1181 (MI0006274), hsa-mir-1182 (MI0006275), hsa-mir-1183 (MI0006276), hsa-mir-1184-1 (MI0006277), hsa-mir-1184-2 (MI0015971), hsa-mir-1184-3 (MI0015972), hsa-mir-1185-1 (MI0003844), hsa-mir-1185-2 (MI0003821), hsa-mir-1193 (MI0014205), hsa-mir-1197 (MI0006656), hsa-mir-1199 (MI0020340), hsa-mir-1200 (MI0006332), hsa-mir-1202 (MI0006334), hsa-mir-1203 (MI0006335), hsa-mir-1204 (MI0006337), hsa-mir-1205 (MI0006338), hsa-mir-1206 (MI0006339), hsa-mir-1207 (MI0006340), hsa-mir-1208 (MI0006341), hsa-mir-1224 (MI0003764), hsa-mir-1225 (MI0006311), hsa-mir-1226 (MI0006313), hsa-mir-1227 (MI0006316), hsa-mir-1228 (MI0006318), hsa-mir-1229 (MI0006319), hsa-mir-1231 (MI0006321), hsa-mir-1233-1 (MI0006323), hsa-mir-1233-2 (MI0015973), hsa-mir-1234 (MI0006324), hsa-mir-1236 (MI0006326), hsa-mir-1237 (MI0006327), hsa-mir-1238 (MI0006328), hsa-mir-1243 (MI0006373), hsa-mir-1244-1 (MI0006379), hsa-mir-1244-2 (MI0015974), hsa-mir-1244-3 (MI0015975), hsa-mir-1245a (MI0006380), hsa-mir-1245b (MI0017431), hsa-mir-1246 (MI0006381), hsa-mir-1247 (MI0006382), hsa-mir-1248 (MI0006383), hsa-mir-1249 (MI0006384), hsa-mir-1250 (MI0006385), hsa-mir-1251 (MI0006386), hsa-mir-1252 (MI0006434), hsa-mir-1253 (MI0006387), hsa-mir-1254-1 (MI000638), hsa-mir-1254-2 (MI0016747), hsa-mir-1255a (MI0006389), hsa-mir-1255b-1 (MI0006435), hsa-mir-1255b-2 (MI0006436), hsa-mir-1256 (MI0006390), hsa-mir-1257 (MI0006391), hsa-mir-1258 (MI0006392), hsa-mir-1260a (MI0006394), hsa-mir-1260b (MI0014197), hsa-mir-1261 (MI0006396), hsa-mir-1262 (MI0006397), hsa-mir-1263 (MI0006398), hsa-mir-1264 (MI0003758), hsa-mir-1265 (MI0006401), hsa-mir-1266 (MI0006403), hsa-mir-1267 (MI0006404), hsa-mir-1268a (MI0006405), hsa-mir-1268b (MI0016748), hsa-mir-1269a (MI0006406), hsa-mir-1269b (MI0016888), hsa-mir-1270-1 (MI0006407), hsa-mir-1270-2 (MI0015976), hsa-mir-1271 (MI0003814), hsa-mir-1272 (MI0006408), hsa-mir-1273a (MI0006409), hsa-mir-1273c (MI0014171), hsa-mir-1273d (MI0014254), hsa-mir-1273e (MI0016059), hsa-mir-1273f (MI0018002), hsa-mir-1273g (MI0018003), hsa-mir-1273h (MI0025512), hsa-mir-1275 (MI0006415), hsa-mir-1276 (MI0006416), hsa-mir-1277 (MI0006419), hsa-mir-1278 (MI0006425), hsa-mir-1279 (MI0006426), hsa-mir-1281 (MI0006428), hsa-mir-1282 (MI0006429), hsa-mir-1283-1 (MI0003832), hsa-mir-1283-2 (MI0006430), hsa-mir-1284 (MI0006431), hsa-mir-1285-1 (MI0006346), hsa-mir-1285-2 (MI0006347), hsa-mir-1286 (MI0006348), hsa-mir-1287 (MI0006349), hsa-mir-1288 (MI0006432), hsa-mir-1289-1 (MI0006350), hsa-mir-1289-2 (MI0006351), hsa-mir-1290 (MI0006352), hsa-mir-1291 (MI0006353), hsa-mir-1292 (MI0006433), hsa-mir-1293 (MI0006355), hsa-mir-1294 (MI0006356), hsa-mir-1295a (MI0006357), hsa-mir-1295b (MI0019146), hsa-mir-1296 (MI0003780), hsa-mir-1297 (MI0006358), hsa-mir-1298 (MI0003938), hsa-mir-1299 (MI0006359), hsa-mir-1301 (MI0003815), hsa-mir-1302-1 (MI0006362), hsa-mir-1302-10 (MI0015979), hsa-mir-1302-11 (MI0015980), hsa-mir-1302-2 (MI0006363), hsa-mir-1302-3 (MI0006364), hsa-mir-1302-4 (MI0006365), hsa-mir-1302-5 (MI0006366), hsa-mir-1302-6 (MI0006367), hsa-mir-1302-7 (MI0006368), hsa-mir-1302-8 (MI0006369), hsa-mir-1302-9 (MI0015978), hsa-mir-1303 (MI0006370), hsa-mir-1304 (MI0006371), hsa-mir-1305 (MI0006372), hsa-mir-1306 (MI0006443), hsa-mir-1307 (MI0006444), hsa-mir-1321 (MI0006652), hsa-mir-1322 (MI0006653), hsa-mir-1323 (MI0003786), hsa-mir-1324 (MI0006657), hsa-mir-1343 (MI0017320), hsa-mir-1468 (MI0003782), hsa-mir-1469 (MI0007074), hsa-mir-1470 (MI0007075), hsa-mir-1471 (MI0007076), hsa-mir-1537 (MI0007258), hsa-mir-1538 (MI0007259), hsa-mir-1539 (MI0007260), hsa-mir-1587 (MI0016905), hsa-mir-1825 (MI0008193), hsa-mir-1827 (MI0008195), hsa-mir-1908 (MI0008329), hsa-mir-1909 (MI0008330), hsa-mir-1910 (MI0008331), hsa-mir-1911 (MI0008332), hsa-mir-1912 (MI0008333), hsa-mir-1913 (MI0008334), hsa-mir-1914 (MI0008335), hsa-mir-1915 (MI0008336), hsa-mir-1972-1 (MI0009982), hsa-mir-1972-2 (MI0015977), hsa-mir-1973 (MI0009983), hsa-mir-1976 (MI0009986), hsa-mir-2052 (MI0010486), hsa-mir-2053 (MI0010487), hsa-mir-2054 (MI0010488), hsa-mir-2110 (MI0010629), hsa-mir-2113 (MI0003939), hsa-mir-2114 (MI0010633), hsa-mir-2115 (MI0010634), hsa-mir-2116 (MI0010635), hsa-mir-2117 (MI0010636), hsa-mir-2276 (MI0011282), hsa-mir-2277 (MI0011284), hsa-mir-2278 (MI0011285), hsa-mir-2355 (MI0015873), hsa-mir-2392 (MI0016870), hsa-mir-2467 (MI0017432), hsa-mir-2681 (MI0012062), hsa-mir-2682 (MI0012063), hsa-mir-2861 (MI0013006), hsa-mir-2909 (MI0013083), hsa-mir-3064 (MI0017375), hsa-mir-3065 (MI0014228), hsa-mir-3074 (MI0014181), hsa-mir-3115 (MI0014127), hsa-mir-3116-1 (MI0014128), hsa-mir-3116-2 (MI0014129), hsa-mir-3117 (MI0014130), hsa-mir-3118-1 (MI0014131), hsa-mir-3118-2 (MI0014132), hsa-mir-3118-3 (MI0014133), hsa-mir-3118-4 (MI0014207), hsa-mir-3118-5 (MI0014243), hsa-mir-3118-6 (MI0015981), hsa-mir-3119-1 (MI0014134), hsa-mir-3119-2 (MI0014135), hsa-mir-3120 (MI0014136), hsa-mir-3121 (MI0014137), hsa-mir-3122 (MI0014138), hsa-mir-3123 (MI0014139), hsa-mir-3124 (MI0014140), hsa-mir-3125 (MI0014142), hsa-mir-3126 (MI0014143), hsa-mir-3127 (MI0014144), hsa-mir-3128 (MI0014145), hsa-mir-3129 (MI0014146), hsa-mir-3130-1 (MI0014147), hsa-mir-3130-2 (MI0014148), hsa-mir-3131 (MI0014151), hsa-mir-3132 (MI0014152), hsa-mir-3133 (MI0014153), hsa-mir-3134 (MI0014155), hsa-mir-3135a (MI0014156), hsa-mir-3135b (MI0016809), hsa-mir-3136 (MI0014158), hsa-mir-3137 (MI0014160), hsa-mir-3138 (MI0014161), hsa-mir-3139 (MI0014162), hsa-mir-3140 (MI0014163), hsa-mir-3141 (MI0014165), hsa-mir-3142 (MI0014166), hsa-mir-3143 (MI0014167), hsa-mir-3144 (MI0014169), hsa-mir-3145 (MI0014170), hsa-mir-3146 (MI0014172), hsa-mir-3147 (MI0014173), hsa-mir-3148 (MI0014175), hsa-mir-3149 (MI0014176), hsa-mir-3150a (MI0014177), hsa-mir-3150b (MI0016426), hsa-mir-3151 (MI0014178), hsa-mir-3152 (MI0014179), hsa-mir-3153 (MI0014180), hsa-mir-3154 (MI0014182), hsa-mir-3155a (MI0014183), hsa-mir-31556 (MI0016839), hsa-mir-3156-1 (MI0014184), hsa-mir-3156-2 (MI0014230), hsa-mir-3156-3 (MI0014242), hsa-mir-3157 (MI0014185), hsa-mir-3158-1 (MI0014186), hsa-mir-3158-2 (MI0014187), hsa-mir-3159 (MI0014188), hsa-mir-3160-1 (MI0014189), hsa-mir-3160-2 (MI0014190), hsa-mir-3161 (MI0014191), hsa-mir-3162 (MI0014192), hsa-mir-3163 (MI0014193), hsa-mir-3164 (MI0014194), hsa-mir-3165 (MI0014195), hsa-mir-3166 (MI0014196), hsa-mir-3167 (MI0014198), hsa-mir-3168 (MI0014199), hsa-mir-3169 (MI0014200), hsa-mir-3170 (MI0014201), hsa-mir-3171 (MI0014202), hsa-mir-3173 (MI0014204), hsa-mir-3174 (MI0014208), hsa-mir-3175 (MI0014209), hsa-mir-3176 (MI0014210), hsa-mir-3177 (MI0014211), hsa-mir-3178 (MI0014212), hsa-mir-3179-1 (MI0014213), hsa-mir-3179-2 (MI0014216; hsa-mir-3179-3 (MI0014221), hsa-mir-3180-1 (MI0014214), hsa-mir-3180-2 (MI0014215; hsa-mir-3180-3 (MI0014217), hsa-mir-3180-4 (MI0016408), hsa-mir-3180-5 (MI0016409), hsa-mir-3181 (MI0014223), hsa-mir-3182 (MI0014224), hsa-mir-3183 (MI0014225), hsa-mir-3184 (MI0014226), hsa-mir-3185 (MI0014227), hsa-mir-3186 (MI0014229), hsa-mir-3187 (MI0014231), hsa-mir-3188 (MI0014232), hsa-mir-3189 (MI0014233), hsa-mir-3190 (MI0014235), hsa-mir-3191 (MI0014236), hsa-mir-3192 (MI0014237), hsa-mir-3193 (MI0014238), hsa-mir-3194 (MI0014239), hsa-mir-3195 (MI0014240), hsa-mir-3196 (MI0014241), hsa-mir-3197 (MI0014245), hsa-mir-3198-1 (MI0014246), hsa-mir-3198-2 (MI0017335), hsa-mir-3199-1 (MI0014247), hsa-mir-3199-2 (MI0014248), hsa-mir-3200 (MI0014249), hsa-mir-3201 (MI0014250), hsa-mir-3202-1 (MI0014252), hsa-mir-3202-2 (MI0014253), hsa-mir-3529 (MI0017351), hsa-mir-3591 (MI0017383), hsa-mir-3605 (MI0015995), hsa-mir-3606 (MI0015996), hsa-mir-3607 (MI0015997), hsa-mir-3609 (MI0015999), hsa-mir-3610 (MI0016000), hsa-mir-3611 (MI0016001), hsa-mir-3612 (MI0016002), hsa-mir-3613 (MI0016003), hsa-mir-3614 (MI0016004), hsa-mir-3615 (MI0016005), hsa-mir-3616 (MI0016006), hsa-mir-3617 (MI0016007), hsa-mir-3618 (MI0016008), hsa-mir-3619 (MI0016009), hsa-mir-3620 (MI0016011), hsa-mir-3621 (MI0016012), hsa-mir-3622a (MI0016013), hsa-mir-3622b (MI0016014), hsa-mir-3646 (MI0016046), hsa-mir-3648 (MI0016048), hsa-mir-3649 (MI0016049), hsa-mir-3650 (MI0016050), hsa-mir-3651 (MI0016051), hsa-mir-3652 (MI0016052), hsa-mir-3653 (MI0016053), hsa-mir-3654 (MI0016054), hsa-mir-3655 (MI0016055), hsa-mir-3656 (MI0016056), hsa-mir-3657 (MI0016057), hsa-mir-3658 (MI0016058), hsa-mir-3659 (MI0016060), hsa-mir-3660 (MI0016061), hsa-mir-3661

(MI0016062), hsa-mir-3662 (MI0016063), hsa-mir-3663 (MI0016064), hsa-mir-3664 (MI0016065), hsa-mir-3665 (MI0016066), hsa-mir-3666 (MI0016067), hsa-mir-3667 (MI0016068), hsa-mir-3668 (MI0016069), hsa-mir-3669 (MI0016070), hsa-mir-3670-1 (MI0016071), hsa-mir-3670-2 (MI0019112), hsa-mir-3671 (MI0016072), hsa-mir-3672 (MI0016073), hsa-mir-3673 (MI0016074), hsa-mir-3674 (MI0016075), hsa-mir-3675 (MI0016076), hsa-mir-3677 (MI0016078), hsa-mir-3678 (MI0016079), hsa-mir-3679 (MI0016080), hsa-mir-3680-1 (MI0016081), hsa-mir-3680-2 (MI0019113), hsa-mir-3681 (MI0016082), hsa-mir-3682 (MI0016083), hsa-mir-3683 (MI0016084), hsa-mir-3684 (MI0016085), hsa-mir-3685 (MI0016086), hsa-mir-3686 (MI0016087), hsa-mir-3687 (MI0016088), hsa-mir-3688-1 (MI0016089), hsa-mir-3688-2 (MI0017447), hsa-mir-3689a (MI0016090), hsa-mir-3689b (MI0016411), hsa-mir-3689c (MI0016832), hsa-mir-3689d-1 (MI0016834), hsa-mir-3689d-2 (MI0016835), hsa-mir-3689e (MI0016836), hsa-mir-3689f (MI0016837), hsa-mir-3690-1 (MI0016091), hsa-mir-3690-2 (MI0023561), hsa-mir-3691 (MI0016092), hsa-mir-3692 (MI0016093), hsa-mir-3713 (MI0016134), hsa-mir-3714 (MI0016135), hsa-mir-3907 (MI0016410), hsa-mir-3908 (MI0016412), hsa-mir-3909 (MI0016413), hsa-mir-3910-1 (MI0016414), hsa-mir-3910-2 (MI0016431), hsa-mir-3911 (MI0016415), hsa-mir-3912 (MI0016416), hsa-mir-3913-1 (MI0016417), hsa-mir-3913-2 (MI0016418), hsa-mir-3914-1 (MI0016419), hsa-mir-3914-2 (MI0016421), hsa-mir-3915 (MI0016420), hsa-mir-3916 (MI0016422), hsa-mir-3917 (MI0016423), hsa-mir-3918 (MI0016424), hsa-mir-3919 (MI0016425), hsa-mir-3920 (MI0016427), hsa-mir-3921 (MI0016428), hsa-mir-3922 (MI0016429), hsa-mir-3923 (MI0016430), hsa-mir-3924 (MI0016432), hsa-mir-3925 (MI0016433), hsa-mir-3926-1 (MI0016434), hsa-mir-3926-2 (MI0016437), hsa-mir-3927 (MI0016435), hsa-mir-3928 (MI0016438), hsa-mir-3929 (MI0016439), hsa-mir-3934 (MI0016590), hsa-mir-3935 (MI0016591), hsa-mir-3936 (MI0016592), hsa-mir-3937 (MI0016593), hsa-mir-3938 (MI0016594), hsa-mir-3939 (MI0016596), hsa-mir-3940 (MI0016597), hsa-mir-3941 (MI0016598), hsa-mir-3942 (MI0016599), hsa-mir-3943 (MI0016600), hsa-mir-3944 (MI0016601), hsa-mir-3945 (MI0016602), hsa-mir-3960 (MI0016964), hsa-mir-3972 (MI0016990), hsa-mir-3973 (MI0016991), hsa-mir-3974 (MI0016992), hsa-mir-3975 (MI0016993), hsa-mir-3976 (MI0016994), hsa-mir-3977 (MI0016995), hsa-mir-3978 (MI0016996), hsa-mir-4251 (MI0015861), hsa-mir-4252 (MI0015864), hsa-mir-4253 (MI0015860), hsa-mir-4254 (MI0015862), hsa-mir-4255 (MI0015863), hsa-mir-4256 (MI0015855), hsa-mir-4257 (MI0015856), hsa-mir-4259 (MI0015858), hsa-mir-4260 (MI0015859), hsa-mir-4261 (MI0015868), hsa-mir-4262 (MI0015872), hsa-mir-4263 (MI0015876), hsa-mir-4264 (MI0015877), hsa-mir-4265 (MI0015869), hsa-mir-4266 (MI0015870), hsa-mir-4267 (MI0015871), hsa-mir-4268 (MI0015874), hsa-mir-4269 (MI0015875), hsa-mir-4270 (MI0015878), hsa-mir-4271 (MI0015879), hsa-mir-4272 (MI0015880), hsa-mir-4273 (MI0015881), hsa-mir-4274 (MI0015884), hsa-mir-4275 (MI0015883), hsa-mir-4276 (MI0015882), hsa-mir-4277 (MI0015886), hsa-mir-4278 (MI0015888), hsa-mir-4279 (MI0015887), hsa-mir-4280 (MI0015889), hsa-mir-4281 (MI0015885), hsa-mir-4282 (MI0015890), hsa-mir-4283-1 (MI0015892), hsa-mir-4283-2 (MI0015982), hsa-mir-4284 (MI0015893), hsa-mir-4285 (MI0015891), hsa-mir-4286 (MI0015894), hsa-mir-4287 (MI0015895), hsa-mir-4288 (MI0015896), hsa-mir-4289 (MI0015898), hsa-mir-4290 (MI0015899), hsa-mir-4291 (MI0015900), hsa-mir-4292 (MI0015897), hsa-mir-4293 (MI0015826), hsa-mir-4294 (MI0015827), hsa-mir-4295 (MI0015822), hsa-mir-4296 (MI0015823), hsa-mir-4297 (MI0015824), hsa-mir-4298 (MI0015830), hsa-mir-4299 (MI0015829), hsa-mir-4300 (MI0015831), hsa-mir-4301 (MI0015828), hsa-mir-4302 (MI0015833), hsa-mir-4303 (MI0015834), hsa-mir-4304 (MI0015832), hsa-mir-4305 (MI0015835), hsa-mir-4306 (MI0015836), hsa-mir-4307 (MI0015838), hsa-mir-4308 (MI0015839), hsa-mir-4309 (MI0015837), hsa-mir-4310 (MI0015840), hsa-mir-4311 (MI0015841), hsa-mir-4312 (MI0015842), hsa-mir-4313 (MI0015843), hsa-mir-4314 (MI0015846), hsa-mir-4315-1 (MI0015844), hsa-mir-4315-2 (MI0015983), hsa-mir-4316 (MI0015845), hsa-mir-4317 (MI0015850), hsa-mir-4318 (MI0015847), hsa-mir-4319 (MI0015848), hsa-mir-4320 (MI0015849), hsa-mir-4321 (MI0015852), hsa-mir-4322 (MI0015851), hsa-mir-4323 (MI0015853), hsa-mir-4324 (MI0015854), hsa-mir-4325 (MI0015865), hsa-mir-4326 (MI0015866), hsa-mir-4327 (MI0015867), hsa-mir-4328 (MI0015904), hsa-mir-4329 (MI0015901), hsa-mir-4330 (MI0015902), hsa-mir-4417 (MI0016753), hsa-mir-4418 (MI0016754), hsa-mir-4419a (MI0016755), hsa-mir-4419b (MI0016861), hsa-mir-4420 (MI0016757), hsa-mir-4421 (MI0016758), hsa-mir-4422 (MI0016759), hsa-mir-4423 (MI0016760), hsa-mir-4424 (MI0016763), hsa-mir-4425 (MI0016764), hsa-mir-4426 (MI0016765), hsa-mir-4427 (MI0016766), hsa-mir-4428 (MI0016767), hsa-mir-4429 (MI0016768), hsa-mir-4430 (MI0016769), hsa-mir-4431 (MI0016771), hsa-mir-4432 (MI0016772), hsa-mir-4433 (MI0016773), hsa-mir-4433b (MI0025511), hsa-mir-4434 (MI0016774), hsa-mir-4435-1 (MI0016775), hsa-mir-4435-2 (MI0016777), hsa-mir-4436a (MI0016776), hsa-mir-4436b-1 (MI0017425), hsa-mir-4436b-2 (MI0019110), hsa-mir-4437 (MI0016778), hsa-mir-4438 (MI0016781), hsa-mir-4439 (MI0016782), hsa-mir-4440 (MI0016783), hsa-mir-4441 (MI0016784), hsa-mir-4442 (MI0016785), hsa-mir-4443 (MI0016786), hsa-mir-4444-1 (MI0016787), hsa-mir-4444-2 (MI0019111), hsa-mir-4445 (MI0016788), hsa-mir-4446 (MI0016789), hsa-mir-4447 (MI0016790), hsa-mir-4448 (MI0016791), hsa-mir-4449 (MI0016792), hsa-mir-4450 (MI0016795), hsa-mir-4451 (MI0016797), hsa-mir-4452 (MI0016798), hsa-mir-4453 (MI0016799), hsa-mir-4454 (MI0016800), hsa-mir-4455 (MI0016801), hsa-mir-4456 (MI0016802), hsa-mir-4457 (MI0016803), hsa-mir-4458 (MI0016804), hsa-mir-4459 (MI0016805), hsa-mir-4460 (MI0016806), hsa-mir-4461 (MI0016807), hsa-mir-4462 (MI0016810), hsa-mir-4463 (MI0016811), hsa-mir-4464 (MI0016812), hsa-mir-4465 (MI0016816), hsa-mir-4466 (MI0016817), hsa-mir-4467 (MI0016818), hsa-mir-4468 (MI0016819), hsa-mir-4469 (MI0016820), hsa-mir-4470 (MI0016821), hsa-mir-4471 (MI0016822), hsa-mir-4472-1 (MI0016823), hsa-mir-4472-2 (MI0016824), hsa-mir-4473 (MI0016825), hsa-mir-4474 (MI0016826), hsa-mir-4475 (MI0016827), hsa-mir-4476 (MI0016828), hsa-mir-4477a (MI0016829), hsa-mir-4477b (MI0016830), hsa-mir-4478 (MI0016831), hsa-mir-4479 (MI0016838), hsa-mir-4480 (MI0016841), hsa-mir-4481 (MI0016842), hsa-mir-4482 (MI0016843), hsa-mir-4483 (MI0016844), hsa-mir-4484 (MI0016845), hsa-mir-4485 (MI0016846), hsa-mir-4486 (MI0016847), hsa-mir-4487 (MI0016848), hsa-mir-4488 (MI0016849), hsa-mir-4489 (MI0016850), hsa-mir-4490 (MI0016852), hsa-mir-4491 (MI0016853), hsa-mir-4492 (MI0016854), hsa-mir-4493 (MI0016855), hsa-mir-4494 (MI0016856), hsa-mir-4495 (MI0016857), hsa-mir-4496 (MI0016858), hsa-mir-4497 (MI0016859), hsa-mir-4498 (MI0016860), hsa-mir-4499 (MI0016862), hsa-mir-4500 (MI0016863), hsa-mir-4501 (MI0016864), hsa-mir-4502 (MI0016865), hsa-mir-4503

(MI0016866), hsa-mir-4504 (MI0016867), hsa-mir-4505 (MI0016868), hsa-mir-4506 (MI0016869), hsa-mir-4507 (MI0016871), hsa-mir-4508 (MI0016872), hsa-mir-4509-1 (MI0016873), hsa-mir-4509-2 (MI0016874), hsa-mir-4509-3 (MI0016875), hsa-mir-4510 (MI0016876), hsa-mir-4511 (MI0016877), hsa-mir-4512 (MI0016878), hsa-mir-4513 (MI0016879), hsa-mir-4514 (MI0016880), hsa-mir-4515 (MI0016881), hsa-mir-4516 (MI0016882), hsa-mir-4517 (MI0016883), hsa-mir-4518 (MI0016884), hsa-mir-4519 (MI0016885), hsa-mir-4520a (MI0016886), hsa-mir-4520b (MI0017358), hsa-mir-4521 (MI0016887), hsa-mir-4522 (MI0016889), hsa-mir-4523 (MI0016890), hsa-mir-4524a (MI0016891), hsa-mir-4524b (MI0019114), hsa-mir-4525 (MI0016892), hsa-mir-4526 (MI0016893), hsa-mir-4527 (MI0016894), hsa-mir-4528 (MI0016895), hsa-mir-4529 (MI0016896), hsa-mir-4530 (MI0016897), hsa-mir-4531 (MI0016898), hsa-mir-4532 (MI0016899), hsa-mir-4533 (MI0016900), hsa-mir-4534 (MI0016901), hsa-mir-4535 (MI0016903), hsa-mir-4536-1 (MI0016906), hsa-mir-4536-2 (MI0019149), hsa-mir-4537 (MI0016908), hsa-mir-4538 (MI0016909), hsa-mir-4539 (MI0016910), hsa-mir-4540 (MI0016911), hsa-mir-4632 (MI0017259), hsa-mir-4633 (MI0017260), hsa-mir-4634 (MI0017261), hsa-mir-4635 (MI0017262), hsa-mir-4636 (MI0017263), hsa-mir-4637 (MI0017264), hsa-mir-4638 (MI0017265), hsa-mir-4639 (MI0017266), hsa-mir-4640 (MI0017267), hsa-mir-4641 (MI0017268), hsa-mir-4642 (MI0017269), hsa-mir-4643 (MI0017270), hsa-mir-4644 (MI0017271), hsa-mir-4645 (MI0017272), hsa-mir-4646 (MI0017273), hsa-mir-4647 (MI0017274), hsa-mir-4648 (MI0017275), hsa-mir-4649 (MI0017276), hsa-mir-4650-1 (MI0017277), hsa-mir-4650-2 (MI0017278), hsa-mir-4651 (MI0017279), hsa-mir-4652 (MI0017280), hsa-mir-4653 (MI0017281), hsa-mir-4654 (MI0017282), hsa-mir-4655 (MI0017283), hsa-mir-4656 (MI0017284), hsa-mir-4657 (MI0017285), hsa-mir-4658 (MI0017286), hsa-mir-4659a (MI0017287), hsa-mir-4659b (MI0017291), hsa-mir-4660 (MI0017288), hsa-mir-4661 (MI0017289), hsa-mir-4662a (MI0017290), hsa-mir-4662b (MI0017293), hsa-mir-4663 (MI0017292), hsa-mir-4664 (MI001729), hsa-mir-4665 (MI0017295), hsa-mir-4666a (MI0017296), hsa-mir-4666b (MI0019299), hsa-mir-4667 (MI0017297), hsa-mir-4668 (MI0017298), hsa-mir-4669 (MI0017300), hsa-mir-4670 (MI0017301), hsa-mir-4671 (MI0017302), hsa-mir-4672 (MI0017303), hsa-mir-4673 (MI0017304), hsa-mir-4674 (MI0017305), hsa-mir-4675 (MI0017306), hsa-mir-4676 (MI0017307), hsa-mir-4677 (MI0017308), hsa-mir-4678 (MI0017309), hsa-mir-4679-1 (MI0017310), hsa-mir-4679-2 (MI0017311), hsa-mir-4680 (MI0017312), hsa-mir-4681 (MI0017313), hsa-mir-4682 (MI0017314), hsa-mir-4683 (MI0017315), hsa-mir-4684 (MI0017316), hsa-mir-4685 (MI0017317), hsa-mir-4686 (MI0017318), hsa-mir-4687 (MI0017319), hsa-mir-4688 (MI0017321), hsa-mir-4689 (MI0017322), hsa-mir-4690 (MI0017323), hsa-mir-4691 (MI0017324), hsa-mir-4692 (MI0017325), hsa-mir-4693 (MI0017326), hsa-mir-4694 (MI0017327), hsa-mir-4695 (MI0017328), hsa-mir-4696 (MI0017329), hsa-mir-4697 (MI0017330), hsa-mir-4698 (MI0017331), hsa-mir-4699 (MI0017332), hsa-mir-4700 (MI0017333), hsa-mir-4701 (MI0017334), hsa-mir-4703 (MI0017336), hsa-mir-4704 (MI0017337), hsa-mir-4705 (MI0017338), hsa-mir-4706 (MI0017339), hsa-mir-4707 (MI0017340), hsa-mir-4708 (MI0017341), hsa-mir-4709 (MI0017342), hsa-mir-4710 (MI0017344), hsa-mir-4711 (MI0017345), hsa-mir-4712 (MI0017346), hsa-mir-4713 (MI0017347), hsa-mir-4714 (MI0017348), hsa-mir-4715 (MI0017349), hsa-mir-4716 (MI0017350), hsa-mir-4717 (MI0017352), hsa-mir-4718 (MI0017353), hsa-mir-4719 (MI0017354), hsa-mir-4720 (MI0017355), hsa-mir-4721 (MI0017356), hsa-mir-4722 (MI0017357), hsa-mir-4723 (MI0017359), hsa-mir-4724 (MI0017361), hsa-mir-4725 (MI0017362), hsa-mir-4726 (MI0017363), hsa-mir-4727 (MI0017364), hsa-mir-4728 (MI0017365), hsa-mir-4729 (MI0017366), hsa-mir-4730 (MI0017367), hsa-mir-4731 (MI0017368), hsa-mir-4732 (MI0017369), hsa-mir-4733 (MI0017370), hsa-mir-4734 (MI0017371), hsa-mir-4735 (MI0017372), hsa-mir-4736 (MI0017373), hsa-mir-4737 (MI0017374), hsa-mir-4738 (MI0017376), hsa-mir-4739 (MI0017377), hsa-mir-4740 (MI0017378), hsa-mir-4741 (MI0017379), hsa-mir-4742 (MI0017380), hsa-mir-4743 (MI0017381), hsa-mir-4744 (MI0017382), hsa-mir-4745 (MI0017384), hsa-mir-4746 (MI0017385), hsa-mir-4747 (MI0017386), hsa-mir-4748 (MI0017387), hsa-mir-4749 (MI0017388), hsa-mir-4750 (MI0017389), hsa-mir-4751 (MI0017390), hsa-mir-4752 (MI0017391), hsa-mir-4753 (MI0017392), hsa-mir-4754 (MI0017394), hsa-mir-4755 (MI0017395), hsa-mir-4756 (MI0017397), hsa-mir-4757 (MI0017398), hsa-mir-4758 (MI0017399), hsa-mir-4759 (MI0017400), hsa-mir-4760 (MI0017401), hsa-mir-4761 (MI0017402), hsa-mir-4762 (MI0017403), hsa-mir-4763 (MI0017404), hsa-mir-4764 (MI0017405), hsa-mir-4765 (MI0017406), hsa-mir-4766 (MI0017407), hsa-mir-4767 (MI0017408), hsa-mir-4768 (MI0017409), hsa-mir-4769 (MI0017410), hsa-mir-4770 (MI0017411), hsa-mir-4771-1 (MI0017412), hsa-mir-4771-2 (MI0017413), hsa-mir-4772 (MI0017414), hsa-mir-4773-1 (MI0017415), hsa-mir-4773-2 (MI0017416), hsa-mir-4774 (MI0017417), hsa-mir-4775 (MI0017418), hsa-mir-4776-1 (MI0017419), hsa-mir-4776-2 (MI0017420), hsa-mir-4777 (MI0017421), hsa-mir-4778 (MI0017422), hsa-mir-4779 (MI0017423), hsa-mir-4780 (MI0017424), hsa-mir-4781 (MI0017426), hsa-mir-4782 (MI0017427), hsa-mir-4783 (MI0017428), hsa-mir-4784 (MI0017429), hsa-mir-4785 (MI0017430), hsa-mir-4786 (MI0017433), hsa-mir-4787 (MI0017434), hsa-mir-4788 (MI0017435), hsa-mir-4789 (MI0017436), hsa-mir-4790 (MI0017437), hsa-mir-4791 (MI0017438), hsa-mir-4792 (MI0017439), hsa-mir-4793 (MI0017440), hsa-mir-4794 (MI0017441), hsa-mir-4795 (MI0017442), hsa-mir-4796 (MI0017443), hsa-mir-4797 (MI0017444), hsa-mir-4798 (MI0017445), hsa-mir-4799 (MI0017446), hsa-mir-4800 (MI0017448), hsa-mir-4801 (MI0017449), hsa-mir-4802 (MI0017450), hsa-mir-4803 (MI0017451), hsa-mir-4804 (MI0017452), hsa-mir-4999 (MI0017865), hsa-mir-5000 (MI0017866), hsa-mir-5001 (MI0017867), hsa-mir-5002 (MI0017868), hsa-mir-5003 (MI0017869), hsa-mir-5004 (MI0017870), hsa-mir-5006 (MI0017873), hsa-mir-5007 (MI0017874), hsa-mir-5008 (MI0017876), hsa-mir-5009 (MI0017877), hsa-mir-5010 (MI0017878), hsa-mir-5011 (MI0017879), hsa-mir-5047 (MI0017932), hsa-mir-5087 (MI0017976), hsa-mir-5088 (MI0017977), hsa-mir-5089 (MI0017978), hsa-mir-5090 (MI0017979), hsa-mir-5091 (MI0017980), hsa-mir-5092 (MI0017981), hsa-mir-5093 (MI0017982), hsa-mir-5094 (MI0017983), hsa-mir-5095 (MI0018001), hsa-mir-5096 (MI0018004), hsa-mir-5100 (MI0019116), hsa-mir-5186 (MI0018165), hsa-mir-5187 (MI0018166), hsa-mir-5188 (MI0018167), hsa-mir-5189 (MI0018168), hsa-mir-5190 (MI0018169), hsa-mir-5191 (MI0018170), hsa-mir-5192 (MI0018171), hsa-mir-5193 (MI0018172), hsa-mir-5194 (MI0018173), hsa-mir-5195 (MI0018174), hsa-mir-5196 (MI0018175), hsa-mir-5197 (MI0018176), hsa-mir-5571 (MI0019115), hsa-mir-5572 (MI0019117), hsa-mir-5579 (MI0019133), hsa-mir-5580 (MI0019135), hsa-mir-5581 (MI0019136), hsa-mir-5582 (MI0019138), hsa-mir-5583-1 (MI0019139), hsa-mir-5583-2 (MI0019140), hsa-mir-5584 (MI0019141), hsa-mir-5585 (MI0019142), hsa-mir-5586 (MI0019143), hsa-mir-5587 (MI0019144), hsa-mir-5588 (MI0019147), hsa-mir-5589 (MI0019148), hsa-mir-5590 (MI0019150), hsa-mir-5591 (MI0019151), hsa-mir-5680 (MI0019280), hsa-mir-5681a (MI0019281), hsa-mir-5681b (MI0019293), hsa-mir-5682 (MI0019282), hsa-mir-5683 (MI0019284), hsa-mir-5684 (MI0019285), hsa-mir-5685 (MI0019287), hsa-mir-5687 (MI0019291), hsa-mir-5688 (MI0019292), hsa-mir-5689 (MI0019294), hsa-mir-5690 (MI0019295), hsa-mir-5691 (MI0019296), hsa-mir-5692a-1 (MI0019297), hsa-mir-5692a-2 (MI0019298), hsa-mir-5692b (MI0019311), hsa-mir-5692c-1 (MI0019288), hsa-mir-5692c-2 (MI0019289), hsa-mir-5693 (MI0019300), hsa-mir-5694 (MI0019301), hsa-mir-5695 (MI0019302), hsa-mir-5696 (MI0019303), hsa-mir-5697 (MI0019304), hsa-mir-5698 (MI0019305), hsa-mir-5699 (MI0019306), hsa-mir-5700 (MI0019307), hsa-mir-5701-1 (MI0019308), hsa-mir-5701-2 (MI0019593), hsa-mir-5702 (MI0019309), hsa-mir-5703 (MI0019310), hsa-mir-5704 (MI0019312), hsa-mir-5705 (MI0019313), hsa-mir-5706 (MI0019314), hsa-mir-5707 (MI0019315), hsa-mir-5708 (MI0019316), hsa-mir-5739 (MI0019412), hsa-mir-5787 (MI0019797), hsa-mir-6068 (MI0020345), hsa-mir-6069 (MI0020346), hsa-mir-6070 (MI0020347), hsa-mir-6071 (MI0020348), hsa-mir-6072 (MI0020349), hsa-mir-6073 (MI0020350), hsa-mir-6074 (MI0020351), hsa-mir-6075 (MI0020352), hsa-mir-6076 (MI0020353), hsa-mir-6077-1 (MI0020354), hsa-mir-6077-2 (MI0023562), hsa-mir-6078 (MI0020355), hsa-mir-6079 (MI0020356), hsa-mir-6080 (MI0020357), hsa-mir-6081 (MI0020358), hsa-mir-6082 (MI0020359), hsa-mir-6083 (MI0020360), hsa-mir-6084 (MI0020361), hsa-mir-6085 (MI0020362), hsa-mir-6086 (MI0020363), hsa-mir-6087 (MI0020364), hsa-mir-6088 (MI0020365), hsa-mir-6089-1 (MI0020366), hsa-mir-6089-2 (MI0023563), hsa-mir-6090 (MI0020367), hsa-mir-6124 (MI0021258), hsa-mir-6125 (MI0021259), hsa-mir-6126 (MI0021260), hsa-mir-6127 (MI0021271), hsa-mir-6128 (MI0021272), hsa-mir-6129 (MI0021274), hsa-mir-6130 (MI0021275), hsa-mir-6131 (MI0021276), hsa-mir-6132 (MI0021277), hsa-mir-6133 (MI0021278), hsa-mir-6134 (MI0021279), hsa-mir-6165 (MI0021472), hsa-mir-6499 (MI0022209), hsa-mir-6500 (MI0022211), hsa-mir-6501 (MI0022213), hsa-mir-6502 (MI0022214), hsa-mir-6503 (MI0022215), hsa-mir-6504 (MI0022216), hsa-mir-6505 (MI0022217), hsa-mir-6506 (MI0022218), hsa-mir-6507 (MI0022219), hsa-mir-6508 (MI0022220), hsa-mir-6509 (MI0022221), hsa-mir-6510 (MI0022222), hsa-mir-6511a-1 (MI0022223), hsa-mir-6511a-2 (MI0023564), hsa-mir-6511a-3 (MI0023565), hsa-mir-6511a-4 (MI0023566), hsa-mir-6511b-1 (MI0022552), hsa-mir-6511b-2 (MI0023431), hsa-mir-6512 (MI0022224), hsa-mir-6513 (MI0022225), hsa-mir-6514 (MI0022226), hsa-mir-6515 (MI0022227), hsa-mir-6516 (MI0025513), hsa-mir-6715a (MI0022548), hsa-mir-6715b (MI0022549), hsa-mir-6716 (MI0022550), hsa-mir-6717 (MI0022551), hsa-mir-6718 (MI0022553), hsa-mir-6719 (MI0022554), hsa-mir-6720 (MI0022555), hsa-mir-6721 (MI0022556), hsa-mir-6722 (MI0022557), hsa-mir-6723 (MI0022558), hsa-mir-6724 (MI0022559), hsa-mir-6726 (MI0022571), hsa-mir-6727 (MI0022572), hsa-mir-6728 (MI0022573), hsa-mir-6729 (MI0022574), hsa-mir-6730 (MI0022575), hsa-mir-6731 (MI0022576), hsa-mir-6732 (MI0022577), hsa-mir-6733 (MI0022578), hsa-mir-6734 (MI0022579), hsa-mir-6735 (MI0022580), hsa-mir-6736 (MI0022581), hsa-mir-6737 (MI0022582), hsa-mir-6738 (MI0022583), hsa-mir-6739 (MI0022584), hsa-mir-6740 (MI0022585), hsa-mir-6741 (MI0022586), hsa-mir-6742 (MI0022587), hsa-mir-6743 (MI0022588), hsa-mir-6744 (MI0022589), hsa-mir-6745 (MI0022590), hsa-mir-6746 (MI0022591), hsa-mir-6747 (MI0022592), hsa-mir-6748 (MI0022593), hsa-mir-6749 (MI0022594), hsa-mir-6750 (MI0022595), hsa-mir-6751 (MI0022596), hsa-mir-6752 (MI0022597), hsa-mir-6753 (MI0022598), hsa-mir-6754 (MI0022599), hsa-mir-6755 (MI0022600), hsa-mir-6756 (MI0022601), hsa-mir-6757 (MI0022602), hsa-mir-6758 (MI0022603), hsa-mir-6759 (MI0022604), hsa-mir-6760 (MI0022605), hsa-mir-6761 (MI0022606), hsa-mir-6762 (MI0022607), hsa-mir-6763 (MI0022608), hsa-mir-6764 (MI0022609), hsa-mir-6765 (MI0022610), hsa-mir-6766 (MI0022611), hsa-mir-6767 (MI0022612), hsa-mir-6768 (MI0022613), hsa-mir-6769a (MI0022614), hsa-mir-6769b (MI0022706), hsa-mir-6770-1 (MI0022615), hsa-mir-6770-2 (MI0026418), hsa-mir-6770-3 (MI0026419), hsa-mir-6771 (MI0022616), hsa-mir-6772 (MI0022617), hsa-mir-6773 (MI0022618), hsa-mir-6774 (MI0022619), hsa-mir-6775 (MI0022620), hsa-mir-6776 (MI0022621), hsa-mir-6777 (MI0022622), hsa-mir-6778 (MI0022623), hsa-mir-6779 (MI0022624), hsa-mir-6780a (MI0022625), hsa-mir-6780b (MI0022681), hsa-mir-6781 (MI0022626), hsa-mir-6782 (MI0022627), hsa-mir-6783 (MI0022628), hsa-mir-6784 (MI0022629), hsa-mir-6785 (MI0022630), hsa-mir-6786 (MI0022631), hsa-mir-6787 (MI0022632), hsa-mir-6788 (MI0022633), hsa-mir-6789 (MI0022634), hsa-mir-6790 (MI0022635), hsa-mir-6791 (MI0022636), hsa-mir-6792 (MI0022637), hsa-mir-6793 (MI0022638), hsa-mir-6794 (MI0022639), hsa-mir-6795 (MI0022640), hsa-mir-6796 (MI0022641), hsa-mir-6797 (MI0022642), hsa-mir-6798 (MI0022643), hsa-mir-6799 (MI0022644), hsa-mir-6800 (MI0022645), hsa-mir-6801 (MI0022646), hsa-mir-6802 (MI0022647), hsa-mir-6803 (MI0022648), hsa-mir-6804 (MI0022649), hsa-mir-6805 (MI0022650), hsa-mir-6806 (MI0022651), hsa-mir-6807 (MI0022652), hsa-mir-6808 (MI0022653), hsa-mir-6809 (MI0022654), hsa-mir-6810 (MI0022655), hsa-mir-6811 (MI0022656), hsa-mir-6812 (MI0022657), hsa-mir-6813 (MI0022658), hsa-mir-6814 (MI0022659), hsa-mir-6815 (MI0022660), hsa-mir-6816 (MI0022661), hsa-mir-6817 (MI0022662), hsa-mir-6818 (MI0022663), hsa-mir-6819 (MI0022664), hsa-mir-6820 (MI0022665), hsa-mir-6821 (MI0022666), hsa-mir-6822 (MI0022667), hsa-mir-6823 (MI0022668), hsa-mir-6824 (MI0022669), hsa-mir-6825 (MI0022670), hsa-mir-6826 (MI0022671), hsa-mir-6827 (MI0022672), hsa-mir-6828 (MI0022673), hsa-mir-6829 (MI0022674), hsa-mir-6830 (MI0022675), hsa-mir-6831 (MI0022676), hsa-mir-6832 (MI0022677), hsa-mir-6833 (MI0022678), hsa-mir-6834 (MI0022679), hsa-mir-6835 (MI0022680), hsa-mir-6836 (MI0022682), hsa-mir-6837 (MI0022683), hsa-mir-6838 (MI0022684), hsa-mir-6839 (MI0022685), hsa-mir-6840 (MI0022686), hsa-mir-6841 (MI0022687), hsa-mir-6842 (MI0022688), hsa-mir-6843 (MI0022689), hsa-mir-6844 (MI0022690), hsa-mir-6845 (MI0022691), hsa-mir-6846 (MI0022692), hsa-mir-6847 (MI0022693), hsa-mir-6848 (MI0022694), hsa-mir-6849 (MI0022695), hsa-mir-6850 (MI0022696), hsa-mir-6851 (MI0022697), hsa-mir-6852 (MI0022698), hsa-mir-6853 (MI0022699), hsa-mir-6854 (MI0022700), hsa-mir-6855 (MI0022701), hsa-mir-6856 (MI0022702), hsa-mir-6857 (MI0022703), hsa-mir-6858 (MI0022704), hsa-mir-6859-1 (MI0022705), hsa-mir-6859-2 (MI0026420), hsa-mir-6859-3 (MI0026421), hsa-mir-6860 (MI0022707), hsa-mir-6861 (MI0022708), hsa-mir-6862-1 (MI0022709), hsa-mir-6862-2 (MI0026415), hsa-mir-6863 (MI0022710), hsa-mir-6864 (MI0022711), hsa-mir-6865 (MI0022712), hsa-mir-6866 (MI0022713), hsa-mir-6867 (MI0022714), hsa-mir-6868 (MI0022715), hsa-mir-6869 (MI0022716), hsa-mir- 6870 (MI0022717), hsa-mir-6871 (MI0022718), hsa-mir-6872 (MI0022719), hsa-mir-6873 (MI0022720), hsa-mir-6874 (MI0022721), hsa-mir-6875 (MI0022722), hsa-mir-6876 (MI0022723), hsa-mir-6877 (MI0022724), hsa-mir-6878 (MI0022725), hsa-mir-6879 (MI0022726), hsa-mir-6880 (MI0022727), hsa-mir-6881 (MI0022728), hsa-mir-6882 (MI0022729), hsa-mir-6883 (MI0022730), hsa-mir-6884 (MI0022731), hsa-mir-6885 (MI0022732), hsa-mir-6886 (MI0022733), hsa-mir-6887 (MI0022734), hsa-mir-6888 (MI0022735), hsa-mir-6889 (MI0022736), hsa-mir-6890 (MI0022737), hsa-mir-6891 (MI0022738), hsa-mir-6892 (MI0022739), hsa-mir-6893 (MI0022740), hsa-mir-6894 (MI0022741), hsa-mir-6895 (MI0022742), hsa-mir-7106 (MI0022957), hsa-mir-7107 (MI0022958), hsa-mir-7108 (MI0022959), hsa-mir-7109 (MI0022960), hsa-mir-7110 (MI0022961), hsa-mir-7111 (MI0022962), hsa-mir-7112-1 (MI0022963), hsa-mir-7112-2 (MI0026414), hsa-mir-7113 (MI0022964), hsa-mir-7114 (MI0022965), hsa-mir-7150 (MI0023610), hsa-mir-7151 (MI0023611), hsa-mir-7152 (MI0023612), hsa-mir-7153 (MI0023613), hsa-mir-7154 (MI0023614), hsa-mir-7155 (MI0023615), hsa-mir-7156 (MI0023616), hsa-mir-7157 (MI0023617), hsa-mir-7158 (MI0023618), hsa-mir-7159 (MI0023620), hsa-mir-7160 (MI0023621), hsa-mir-7161 (MI0023619), hsa-mir-7162 (MI0023623), hsa-mir-7515 (MI0024354), hsa-mir-7641-1 (MI0024975), hsa-mir-7641-2 (MI0024976), hsa-mir-7702 (MI0025238), hsa-mir-7703 (MI0025239), hsa-mir-7704 (MI0025240), hsa-mir-7705 (MI0025241), hsa-mir-7706 (MI0025242), hsa-mir-7843 (MI0025510), hsa-mir-7844 (MI0025514), hsa-mir-7845 (MI0025515), hsa-mir-7846 (MI0025516), hsa-mir-7847 (MI0025517), hsa-mir-7848 (MI0025518), hsa-mir-7849 (MI0025519), hsa-mir-7850 (MI0025520), hsa-mir-7851 (MI0025521), hsa-mir-7852 (MI0025522), hsa-mir-7853 (MI0025523), hsa-mir-7854 (MI0025524), hsa-mir-7855 (MI0025525), hsa-mir-7856 (MI0025526), hsa-mir-7973-1 (MI0025748), hsa-mir-7973-2 (MI0025749), hsa-mir-7974 (MI0025750), hsa-mir-7975 (MI0025751), hsa-mir-7976 (MI0025752), hsa-mir-7977 (MI0025753), hsa-mir-7978 (MI0025754), hsa-mir-8052 (MI0025888), hsa-mir-8053 (MI0025889), hsa-mir-8054 (MI0025890), hsa-mir-8055 (MI0025891), hsa-mir-8056 (MI0025892), hsa-mir-8057 (MI0025893), hsa-mir-8058 (MI0025894), hsa-mir-8059 (MI0025895), hsa-mir-8060 (MI0025896), hsa-mir-8061 (MI0025897), hsa-mir-8062 (MI0025898), hsa-mir-8063 (MI0025899), hsa-mir-8064 (MI0025900), hsa-mir-8065 (MI0025901), hsa-mir-8066 (MI0025902), hsa-mir-8067 (MI0025903), hsa-mir-8068 (MI0025904), hsa-mir-8069 (MI0025905), hsa-mir-8070 (MI0025906), hsa-mir-8071-1 (MI0025907), hsa-mir-8071-2 (MI0026417), hsa-mir-8072 (MI0025908), hsa-mir-8073 (MI0025909), hsa-mir-8074 (MI0025910), hsa-mir-8075 (MI0025911), hsa-mir-8076 (MI0025912), hsa-mir-8077 (MI0025913), hsa-mir-8078 (MI0025914), hsa-mir-8079 (MI0025915), hsa-mir-8080 (MI0025916), hsa-mir-8081 (MI0025917), hsa-mir-8082 (MI0025918), hsa-mir-8083 (MI0025919), hsa-mir-8084 (MI0025920), hsa-mir-8085 (MI0025921), hsa-mir-8086 (MI0025922), hsa-mir-8087 (MI0025923), hsa-mir-8088 (MI0025924), hsa-mir-8089 (MI0025925). See, e.g., pre-microRNAs listed on miRBase.org In varying embodiments, the pre-microRNA is not pre-miRNA-22, pre-miRNA-122, pre-miRNA-124-2, pre-miRNA-125-2, pre-miRNA-155 or pre-miRNA-221.

In varying embodiments, the hybrid molecules comprise the full-length native pre-micro-RNA. In some embodiments, the hybrid molecules comprise fragments or subsequences of the native pre-micro-RNA molecules. Fragments or subsequences of the native pre-micro-RNA molecules that find use will have one or more cleavage sites recognized by and accessible to an endoribonuclease (e.g., Dicer) such that an inserted RNA molecule (e.g., a noncoding RNA (ncRNA), mature microRNA (miRNA), a small interfering RNA (siRNA), a short hairpin RNA (shRNA), a Piwi-interacting RNA (piRNA), a small nuclear RNA (snRNA), a small nucleolar RNA (snoRNA), an aptamer) can be cleaved out of or released from the hybrid tRNA/pre-microRNA molecule.

In varying embodiments, the tRNA operably linked to a pre-microRNA (pre-miRNA) comprises a polynucleotide sequence having at least about 90% sequence identity, e.g., at least 91%, 92%, 93%, 94%, 95%, 96%, 97%, 98%, 99% or 100% sequence identity, to a polynucleotide selected from the group consisting of SEQ ID NO:3, SEQ ID NO:4, SEQ ID NO:5, SEQ ID NO:6, SEQ ID NO:7, SEQ ID NO:8, SEQ ID NO:13 and SEQ ID NO:15. In some embodiments, the tRNA operably linked to the pre-microRNA (pre-miRNA) and the aptamer comprises a polynucleotide sequence having at least about 90% sequence identity, e.g., at least 91%, 92%, 93%, 94%, 95%, 96%, 97%, 98%, 99% or 100% sequence identity, to SEQ ID NO:10. In some embodiments, the tRNA operably linked to the pre-microRNA (pre-miRNA) and the aptamer comprises a polynucleotide sequence having at least about 90% sequence identity, e.g., at least 91%, 92%, 93%, 94%, 95%, 96%, 97%, 98%, 99% or 100% sequence identity, to SEQ ID NO:11.

c. Aptamer

The hybrid tRNA/pre-microRNA molecules are further operably linked to an aptamer. In varying embodiments, the aptamer can be inserted/positioned/located either 5' to the pre-microRNA (as illustrated by SEQ ID NO:10-OnRS-2/MGA5) or 3' to the pre-microRNA (as illustrated by SEQ ID NO:11-OnRS-2/MGA3). Of interest are aptamers that elicit a detectable signal when bound to their analytes. The aptamer/analyte pairs can elicit the detectable signal while the aptamer is retained as an intact or substantially intact polynucleotide (e.g., sufficient for the aptamer to bind the analyte) within hybrid tRNA/pre-microRNA molecule. In varying embodiments, the aptamers elicit a fluorescent signal when bound to its analyte.

In some embodiments, the aptamer binds to a dye selected from the group consisting of malachite green, tetramethylrosamine, sulforhodamine B, and triphenylmethane dyes. In varying embodiments, the aptamer binds to malachite green. In varying embodiments, the aptamer comprises a polynucleotide sequence having at least about 90% sequence identity, e.g., at least 91%, 92%, 93%, 94%, 95%, 96%, 97%, 98%, 99% or 100% sequence identity, to SEQ ID NO:9.

3. Methods of Detection RNase Activity

Further provided are methods of detecting RNase activity. In varying embodiments, the methods entail:

a) contacting a test sample suspected of having RNase with a composition comprising a hybrid tRNA/pre-microRNA molecule comprising an aptamer and the analyte that binds to the aptamer, thereby forming a mixture, wherein the analyte bound by the aptamer elicits a detectable signal;

b) determining the presence and amount of detectable signal in the mixture in comparison to the presence and amount of detectable signal in a control composition that has not been contacted with the sample, wherein reduced or eliminated levels of detectable signal indicate the presence of RNase activity. Samples that have RNases and RNase activity will degrade the hybrid tRNA/pre-microRNA molecule comprising the aptamer such that the aptamer no longer binds to the analyte.

In varying embodiments, the test sample is a biological sample. In varying embodiments, the biological sample is a fluid sample selected from the group consisting of serum, blood, sweat, tears, plasma, saliva, mucous, sputum, milk, semen, urine, and vaginal secretions. In varying embodiments, the biological sample is a biopsy. In varying embodiments, the RNase activity is from one or more endoribonucleases, e.g., RNase A (EC 3.1.27.5), RNase H (EC 3.1.26.4), RNase III (EC 3.1.26.3), RNase L, RNase P (EC 3.1.26.5), RNase PhyM, RNase T1 (EC 3.1.27.3), RNase T2 (EC 3.1.27.1), RNase U2 (EC 3.1.27.4), and RNase V (EC 3.1.27.8). In varying embodiments, the RNase activity is from one or more exoribonucleases, e.g., Polynucleotide Phosphorylase (PNPase) (EC 2.7.7.8), RNase PH (EC number EC 2.7.7.56), RNase R, RNase D (EC 3.1.13.5), RNase T, Oligoribonuclease (EC 3.1.13.3), Exoribonuclease I (EC 3.1.11.1), and Exoribonuclease II (EC 3.1.13.1). In varying embodiments, the RNase activity is from one or more ribonucleases selected from the group consisting of tRNA nucleotidyltransferase (EC 2.7.7.56), Ribonuclease D (EC 3.1.13.5), *Physarum polycephalum* ribonuclease (EC 3.1.26.1), Ribonuclease alpha (EC 3.1.26.2), Ribonuclease III (EC 3.1.26.3), Ribonuclease H (EC 3.1.26.4), Ribonuclease P (EC 3.1.26.5), Ribonuclease IV (EC 3.1.26.6), Ribonuclease P4 (3.1.26.7), Ribonuclease M5 (EC 3.1.26.8), Ribonuclease (poly-(U)-specific) (EC 3.1.26.9), Ribonuclease IX (EC 3.1.26.10), Ribonuclease Z (EC 3.1.26.11), Ribonuclease E (EC 3.1.26.12), Retroviral ribonuclease H (EC 3.1.26.13), Ribonuclease T(2) (EC 3.1.27.1), *Bacillus subtilis* ribonuclease (EC 3.1.27.2), Ribonuclease T(1) (EC 3.1.27.3), Ribonuclease U(2) (EC 3.1.27.4), Pancreatic ribonuclease (EC 3.1.27.5), *Enterobacter* ribonuclease (EC 3.1.27.6), Ribonuclease F (EC 3.1.27.7), Ribonuclease V (EC 3.1.27.8), Exoribonuclease II (EC 3.1.13.1), Exoribonuclease H (3.1.13.2), Poly(A)-specific ribonuclease (3.1.13.4), Ribonuclease D (EC 3.1.13.5), and Yeast ribonuclease (EC 3.1.14.1).

The test sample suspected of having RNase is contacted with a composition comprising a hybrid tRNA/pre-microRNA molecule comprising an aptamer bound to its analyte under conditions and for a time sufficient to allow RNase, if present, to degrade the aptamer and disrupt aptamer/analyte binding. In varying embodiments, the contacting step can be performed under physiological conditions of salinity (e.g., 100 mM KCl, 5 mM MgCl$_2$, and 10 mM HEPES), pH (e.g., pH 7.4) and temperature (e.g., 37° C.) for a time period of about 5 to 60 minutes.

The detecting step can be performed using any appropriate method known in the art, and will depend on the detectable signal elicited by the aptamer/analyte pair. RNase activity is calculated as the change in detectable signal (e.g., fluorescent intensity) over time per volume of sample (e.g., ΔA.U./min/μL). A reduction or disappearance in detectable signal (e.g., fluorescent intensity) in a mixture comprising the test sample and the hybrid tRNA/pre-microRNA molecule comprising an aptamer bound to its analyte in comparison to detectable signal (e.g., fluorescent intensity) in a control composition comprising the hybrid tRNA/pre-microRNA molecule comprising an aptamer bound to its analyte without contacting the test sample indicates that the test sample comprises RNases and RNase activity. A further control can include determining detectable signal (e.g., fluorescent intensity) of the same biological sample from a healthy control subject (e.g., a subject known not to have the disease of interest). A reduced or eliminated detectable signal (e.g., fluorescent intensity) in the test sample versus the control subject sample indicates elevated RNase activity in the test sample compared to the sample from the control subject. Similarly, an increased detectable signal (e.g., fluorescence) in the test sample versus the control subject sample indicates reduced RNase activity in the test sample compared to the sample from the control subject.

In varying embodiments RNase activity can be detected and quantified at the milligram level without dilution of test sample.

4. Compositions and Kits

Further provided are compositions comprising the polynucleotides described above and herein, comprising a hybrid tRNA/pre-microRNA molecule comprising an aptamer bound to its analyte (e.g., a hybrid tRNA/pre-microRNA molecule comprising an aptamer that binds to a dye such as malachite green where the aptamer is bound to malachite green).

Further provided are kits comprising one or more receptacles/containers/vials comprising one or more polynucleotides described above and herein, comprising a hybrid tRNA/pre-microRNA molecule comprising an aptamer. Also provided are kits comprising one or more receptacles/containers/vials comprising one or more compositions described above and herein, comprising a hybrid tRNA/pre-microRNA molecule comprising an aptamer bound to its analyte.

5. High Level Production of Hybrid tRNA/Pre-microRNA Molecules In Vitro

The hybrid tRNA/pre-microRNA molecules can be produced by recombinant expression in a host cell, or can be synthetically prepared. Such recombinant and synthetic methods are well known in the art. When produced by recombinant expression in a host cell, the host cell can be eukaryotic or prokaryotic. In varying embodiments, the host cell is of the same species of cell as that of the tRNA molecule or the pre-microRNA molecule used in the hybrid tRNA/pre-microRNA molecule. When producing a hybrid tRNA/pre-microRNA molecule comprising an inserted RNA sequence, a host cell that does not comprise an endoribonuclease that may cleave out the inserted RNA (e.g., Dicer) can be used. In varying embodiments, the host cell for the recombinant expression of a hybrid tRNA/pre-microRNA molecule is a prokaryotic cell, e.g., a bacterial cell, e.g., an *Escherichia coli* cell. In varying embodiments, the host cell for the recombinant expression of a hybrid tRNA/pre-microRNA molecule is a eukaryotic cell, e.g., a mammalian cell, a human cell, an insect cell, a plant cell or a yeast cell. Eukaryotic (e.g., mammalian or human) host cells which are deficient for Dicer are known in the art and find use for the high level expression for production of the hybrid tRNA/pre-microRNA molecules in a eukaryotic host cell, e.g., as described in Commins, et al. *Proc Natl Acad Sci USA*, (2006) 103(10):3687-3692; Murchison, et al., *Proc Natl Acad Sci USA*, (2005) 102(34):12135-12140; and Kanellopoulou, et al., *Genes Dev.*, (2005) 19:489-501.

The hybrid tRNA/pre-microRNA scaffolds facilitate stable, consistent and reliable high level expression of a desired inserted RNA molecule in vivo and in vitro, as described herein. In varying embodiments, high levels of the hybrid tRNA/pre-microRNA scaffolds are produced in vitro by a host cell that does not comprise an endoribonuclease that may cleave out the inserted RNA (e.g., Dicer). In varying embodiments, at least about 5-100 mg, e.g., at least about 10-50 mg, of hybrid tRNA/pre-microRNA scaffold molecules can be produced in vitro from 1 liter of *E. coli* culture over 16-48 hours of time. In varying embodiments, at least about 5-100 mg, e.g., at least about 10-50 mg, of hybrid tRNA/pre-microRNA scaffold molecules can be produced in vitro from 1 liter of yeast cell culture. In some embodiments, the tRNA/pre-microRNA molecule produced comprises at least about 5%, e.g., at least about 6%, 7%, 8%, 9%, 10%, 11%, 12%, 15%, 20%, or more, of the total RNA.

In varying embodiments, the hybrid tRNA/pre-microRNA scaffolds are purified as part of the total RNA from the production host cells. Such methods of isolating or purifying total RNA from a host cell are established in the art. In some embodiments, the hybrid tRNA/pre-microRNA scaffolds are further substantially isolated or purified from the other RNA molecules and components of the production host cell. This can be done using any method in the art, including, e.g., separation by separation by gel electrophoresis, affinity chromatography, chromatography, FPLC and/or HPLC. The substantially isolated and/or purified hybrid tRNA/pre-microRNA scaffolds can then be transfected or delivered into a eukaryotic cell, which will then process the hybrid tRNA/pre-microRNA scaffolds to cleave or release the inserted RNA.

In varying embodiments, the hybrid tRNA/pre-microRNA scaffolds are contacted with or exposed to an endoribonuclease (e.g., Dicer) in vitro, under conditions sufficient to allow cleave or release of the inserted RNA. In varying embodiments, the efficiency of in vitro cleavage or release of the inserted RNA from the hybrid tRNA/pre-microRNA scaffolds can be facilitated by adding a RNase or DNAzyme site to the tRNA-pre-miRNA molecule

EXAMPLES

The following examples are offered to illustrate, but not to limit the claimed invention.

Example 1

A General Approach to High-Yield Biosynthesis of Chimeric RNAs Bearing Various Types of Functional Small RNAs for Broad Applications RNA research and therapy relies primarily on synthetic RNAs. We employed recombinant RNA technology towards large-scale production of pre-miRNA agents in bacteria, but found the majority of target RNAs were not or negligibly expressed. We thus developed a novel strategy to achieve consistent high-yield biosynthesis of chimeric RNAs carrying various small RNAs (e.g., miRNAs, siRNAs and RNA aptamers), which was based upon an optimal noncoding RNA scaffold (OnRS) derived from tRNA fusion pre-miR-34a (tRNA/mir-34a). Multi-milligrams of chimeric RNAs (e.g., OnRS/miR-124, OnRS/GFP-siRNA, OnRS/Neg (scrambled RNA) and OnRS/MGA (malachite green aptamer)) were readily obtained from 1 L bacterial culture. Deep sequencing analyses revealed that mature miR-124 and target GFP-siRNA were selectively released from chimeric RNAs in human cells. Consequently, OnRS/miR-124 was active in suppressing miR-124 target gene expression and controlling cellular processes, and OnRS/GFP-siRNA was effective in knocking down GFP mRNA levels and fluorescent intensity in ES-2/GFP cells and GFP-transgenic mice. Furthermore, the OnRS/MGA sensor offered a specific strong fluorescence upon binding MG, which was utilized as label-free substrate to accurately determine serum RNase activities in pancreatic cancer patients. These results demonstrate that OnRS-based bioengineering is a common, robust and versatile strategy to assemble various types of small RNAs for broad applications.

Introduction

RNA interference (RNAi) technologies have been widely utilized for genome function studies. There are also a number of RNAi-based therapies under clinical trials (1-3) in addition to an RNA aptamer (Pegaptanib) being approved by the U.S. Food and Drug Administration for the treatment of age-related macular degeneration (4). Currently RNAi agents and noncoding RNA (ncRNA) materials used for basic, translational and clinical research such as small interfering RNAs (siRNAs), short hairpin RNAs (shRNAs), RNA aptamers, and microRNAs (miRs or miRNAs) are mainly produced through chemical synthesis (5-9), while other virus and non-virus-vector based strategies literally utilize DNA agents. Although organic synthesis of oligonucleotides may be automated, a multi-milligram dose of 22-nt double-stranded siRNA or miRNA agents for in-vivo testing or projected therapy is very costly. It is also unclear to what extent chemical modifications would alter the structures, biological activities and safety profiles of these ncRNAs, despite that synthetic ncRNAs exhibit some favorable pharmacokinetic properties such as a longer half-life. In vitro transcription (10,11) is another way to produce RNA agents in variable lengths. However, in vitro transcription generally produces RNA molecules in a test tube on micrograms scale, thus the production of larger quantities of RNAs requires considerably more of the costly RNA polymerases.

With an interest in developing new strategies to bioengineer ready-to-use RNAi agents on a large scale, a successful example has been reported very recently for the generation of fully-processed siRNAs from p19-expressing bacteria (12). On the other hand, tRNA (13-15) and rRNA (16) have been employed as scaffolds to produce a number of chimeric RNAs in common strains of bacteria, given the fact that tRNAs and rRNAs are present as stable RNA molecules in the cells. The recombinant RNA chimeras are thus isolated, and the target RNAs may be released in demand by corresponding RNase (13,14), Ribozyme (15) or DNAzyme (16) for structural and biophysical analyses. These recombinant RNA technologies provide a novel way for a cost-effective and fast production of large quantities of recombinant RNAs (e.g., milligrams of RNA chimeras from 1 L bacteria culture).

We had taken the initiative to produce pre-miRNA chimeras (FIG. 1a) in common strains of E. coli using tRNA scaffold (17). We hypothesized that fusion tRNA/pre-miRNA isolated from bacteria might act as a "prodrug" where pre-miRNA could be selectively processed to mature miRNA in human cells, and tRNA scaffold would be degraded to tRNA fragments (tRFs). In the present study, we demonstrated that the majority of tRNA/pre-miRNA chimeras did not accumulate in bacteria or only at a negligible level, thus we developed a novel optimal ncRNA scaffold (OnRS)-based strategy to achieve a consistent high-yield production of chimeric RNAs in E. coli that offers the versatility to carry various types of functional small RNAs of interests such as miRNAs, siRNAs and RNA aptamers (FIG. 1b). This approach is proven robust and shall have broad applications to engineering of target chimeric RNAi agents and RNA sensors that may be utilized as research tools and further developed as therapeutic agents and diagnostic tools.

Materials and Methods

Bacterial Culture.

All *E. coli* stains were cultured at 37° C. in LB broth supplemented with 100 μg/mL ampicillin. DH5a (Life Technologies, Grand Island, N.Y.) was used for cloning and HST08 (Clontech Laboratories, Mountain View, Calif.) was employed for the production of multi-milligrams of chimeric RNAs. Other strains such as DH5a, Top 10 (Life Technologies, Grand Island, N.Y.) and BL21 (Sigma-Aldrich, St. Louis, Mo.) were also used to evaluate ncRNA expression/accumulation.

Human Cell Culture.

The human carcinoma cell line A549 was purchased from American Type Culture Collection (Manassas, Va.), and ES-2/GFP was from Cell Biolabs (San Diego, Calif.). Both cell lines were maintained in RPMI 1640 with 10% fetal bovine serum at 37° C. in a humidified atmosphere with 5% $CO_2$ and 95% air.

Prediction of RNA Secondary Structures.

The secondary structures of chimeric ncRNAs were predicted using the CentroidFold (www.ncrna.org/centroidfold) (18) and CentroidHomfold (www.ncrna.org/centroidhomfold) (19).

Construction of Plasmids.

Individual tRNA/pre-miRNA expression plasmids were cloned as we reported (17), following PCR amplification of target sequences from human genomic DNA using gene specific primers (IDT, San Diego, Calif.). See, Table 1. To create OnRS/miR-124, OnRS/Neg, OnRS/GFP-siRNA and Trna-miR-155/GFP-siRNA expression plasmids, the oligonucleotides (Table 1) were annealed and amplified, then the amplicons were cloned into the vector pBSMrnaSeph (14) (kindly provided by Dr. Luc Ponchon, France) linearized by endonucleases SalI-HF® and AatII (New England Biolabs, Ipswich, Mass.). To construct OnRS/MGA5 and OnRS/MGA3 expression plasmids, Trna/mir-34a was used as a template for the amplification of target sequences using the oligonucleotides (Table 1), and then the amplicons were inserted into pBSMrnaSeph vector linearized by SacII and EagI (New England Biolabs) which removed the SEPH-ADEX™aptamer from Trna scaffold at the same time. All inserts were confirmed by Sanger sequencing analyses at UC Davis Genome Center.

TABLE 1a (a) Sequences of OnRS-based chimeric RNAs

| Target RNAs | Sequences (5'→3') |
|---|---|
| OnRS (tRNA/mir-34a) | GGCUACGUAGCUCAGUUGGUUAGAGCAGCGGCCGAGUAAUUUACGUCGAC<br>GUGGACCGGCCAGCUGUGAGUGUUUCUUUGGCAGUGUCUUAGCUGGUUGU<br>UGUGAGCAAUAGUAAGGAAGCAAUCAGCAAGUAUACUGCCCUAGAAGUGC<br>UGCACGUUGUGGGGCCCAAGAGGGAAGAT<br>GACGUCGAUGGUUGCGGCCGCGGGUCACAGGUUCGAAUCCCGUCGUAGCCACCA (SEQ ID NO: 16) |
| OnRS/miR-124 | GGCUACGUAGCUCAGUUGGUUAGAGCAGCGGCCGAGUAAUUUACGUCGAC<br>CCGUGGACCGGCCAGCUGUGAGUGUUUCUUUAAGGCACGCGGUGAAUGCC<br>UGUGAGCAAUAGUAAGGAAGCAUUCACGCUGUGCCUUCUAGAAGUGCUG<br>CACGUUGUGGGGCCCAAGAGGGAAGACGUCGAUGGUUGCGGCCGCG<br>GGUCACAGGUUCGAAUCCCGUCGUAGCCACCA (SEQ ID NO: 17) |
| OnRS/Neg | GGCUACGUAGCUCAGUUGGUUAGAGCAGCGGCCGAGUAAUUUACGUCGAC<br>CCGUGGACCGGCCAGCUGUGAGUGUUUCUUCACCUAUAACAACGGUAGUU<br>UUUGUGAGCAAUAGUAAGGAAGAAACUACCUUGUUUAUAGGUCUAGAAGU<br>GCUGCACGUUGUGGGGCCCAAGAGGGAA<br>GACGUCGAUGGUUGCGGCCGCGGGUCACAGGUUCGAAUCCCGUCGUAGCCACCA (SEQ ID NO: 18) |
| OnRS/GFP-siRNA | GGCUACGUAGCUCAGUUGGUUAGAGCAGCGGCCGAGUAAUUUACGUCGAC<br>CCGUGGACCGGCCAGCUGUGAGUGUUUCUUAGUUGUACUCCAGCUUGUGC<br>CCUGUGAGCAAUAGUAAGGAAGGGCACAAGUGGUAGUACAACCUAGAAGU<br>GCUGCACGUUGUGGGGCCCAAGAGGGAA<br>GACGUCGAUGGUUGCGGCCGCGGGUCACAGGUUCGAAUCCCGUCGUAGCCACCA (SEQ ID NO: 19) |
| OnRS/MGA5 | GGCUACGUAGCUCAGUUGGUUAGAGCAGCGGCCGGAUCCCGACUGGCGA<br>GAGCCAGGUAACGAAUGGAUCCGUGGACCGGCCAGCUGUGAGUGUUUCUU<br>UGGCAGUGUCUUAGCUGGUUGUGUGAGCAAUAGUAAGGAAGCAAUCAGC<br>AAGUAUACUGCCCUAGAAGUGCUGCACGUUGUGGGGCCC<br>GGUCCACCCGCGGGUCACAGGUUCGAAUCCCGUCGUAGCCACCA (SEQ ID NO: 10) |
| OnRS/MGA3 | GGCUACGUAGCUCAGUUGGUUAGAGCAGCGGCCGGUGGACCGGCCAGCUG<br>UGAGUGUUUCUUUGGCAGUGUCUUAGCUGGUUGUGUGAGCAAUAGUAAG<br>GAAGCAAUCAGCAAGUAUACUGCCCUAGAAGUGCUGCACGUUGUGGGGCC<br>CGGUCCACGGAUCCCGACUGGCGAGAGCCAGGUAACGAAUGGAUCC<br>CCGCGGGUCACAGGUUCGAAUCCCGUCGUAGCCACCA (SEQ ID NO: 11) |

The underlined are the sequences of tRNA scaffold.
The rest is the hsa-miR-34a precursor with ~9 nt flanking sequence at each prime.
The sequence in red indicates the target sequence and the green part is the complementary sequence.
Sequence in bold indicates the MGA.

TABLE 1b

| | (b) Oligonucleotides used for plasmid construction and qPCR analysis |
|---|---|
| Plasmids | Primer sequences (5'→3') |
| tRNA/mir-27b | Fow-ACGCGTCGACCCAGCGATGACCTCTCTAAC (SEQ ID NO: 20)<br>Rev-CATCGACGTCCTTAACTGTCCCCATCTCACC (SEQ ID NO: 21) |
| tRNA/mir-34a | Fow-AGTAATTTACGTCGACGTGGACCGGCCAGCTGTGAGTGTT (SEQ ID NO: 22)<br>Rev-CGGCCGCAACCATCGACGTCATCTTCCCTCTTGGGCCCCACAACG (SEQ ID NO: 23) |
| tRNA/mir-122 | Fow-AGTAATTTACGTCGACTTCGTGGCTACAGAGTTTCCTTAGCAG (SEQ ID NO: 24)<br>Rev-CGGCCGCAACCATCGACGTCCAAGACATTTATCGAGGGAAGGATTGC (SEQ ID NO: 25) |
| tRNA/mir-124-1 | Fow-AGTAATTTACGTCGACCTCCTTTCCTTCCTCAGGAG (SEQ ID NO: 26)<br>Rev-CGGCCGCAACCATCGACGTCCGCCGACCCACGGTGCTCA (SEQ ID NO: 27) |
| tRNA/mir-124-2 | Fow-AGTAATTTACGTCGACTACTTTCCGGATCAAGATTAG (SEQ ID NO: 28)<br>Rev-CGGCCGCAACCATCGACGTCTTGGTGTCCTTCAAGTGCAG (SEQ ID NO: 29) |
| tRNA/mir-125-1 | Fow-AGTAATTTACGTCGACAGAAAACATTGTTGCGCTCCTCTC (SEQ ID NO: 30)<br>Rev-CGGCCGCAACCATCGACGTCAGGATGCAAAAGCACGACTCGC (SEQ ID NO: 31) |
| tRNA/mir-125-2 | Fow-AGTAATTTACGTCGACTCTACCGCATCAAACCAGACTTTTCC (SEQ ID NO: 32)<br>Rev-CGGCCGCAACCATCGACGTCCTGCTGGTTCCCCTCCGCC (SEQ ID NO: 33) |
| tRNA/mir-155 | Fow-AGTAATTTACGTCGACAGGCTTGCTGTAGGCTGTATGCTG (SEQ ID NO: 34)<br>Rev-CGGCCGCAACCATCGACGTCAATGCTAGTAACAGGCATCATACACTGTTA (SEQ ID NO: 35) |
| tRNA/mir-221 | Fow-AGTAATTTACGTCGACCTTGCAAGCTGAACATCCAGGTCTG (SEQ ID NO: 36)<br>Rev-CGGCCGCAACCATCGACGTCCAGCCAATGGAGAACATGTTTCCA (SEQ ID NO: 37) |
| tRNA/mir-1291 | Fow-ACGCGTCGACGAGTTCTGTCCGTGAGCCTTGG (SEQ ID NO: 38)<br>Rev-CATCGACGTCACAGCCAACAGACCACAGGAAG (SEQ ID NO: 39) |
| tNRNA/let7a | Fow-AGTAATTTACGTCGACACCCTGGATGTTCTCTTCAC (SEQ ID NO: 40)<br>Rev-CGGCCGCAACCATCGACGTCGATGCAGACTTTTCTATCACG (SEQ ID NO: 41) |
| OnRS/miR-124-20 | Fow-AGTAATTTACGTCGACCCGTGGACCGGCCAGCTGTGAGTGTTTCTTTAAGGCACGCGGTGAATGCCTGTGAGCAATAGTAAGGAAGGC (SEQ ID NO: 42)<br>Rev-GGCCGCAACCATCGACGTCTTCCCTCTTGGGCCCCACAACGTGCAGCACTTCTAGAAGGCACAGCGTGAATGCCTTCCTTACTATTGC (SEQ ID NO: 43) |
| OnRS/Neg | Fow-AGTAATTTACGTCGACCCGTGGACCGGCCAGCTGTGAGTGTTTCTTCACCTATAACAACGGTAGTTTTTGTGAGCAATAGTAAGGAAG (SEQ ID NO: 44)<br>Rev-CGGCCGCAACCATCGACGTCTTCCCTCTTGGGCCCCACAACGTGCAGCACTTCTAGACCTATAAACAAGGTAGTTTCTTCCTTACTATTG (SEQ ID NO: 45) |
| OnRS/GFP siRNA | Fow-AGTAATTTACGTCGACCCGTGGACCGGCCAGCTGTGAGTGTTTCTTAGTTGTACTCCAGCTTGTGCCCTGTGAGCAATAGTAAGGAAGGGAA (SEQ ID NO: 46)<br>Rev-CGGCCGCAACCATCGACGTCTTCCCTCTTGGGCCCCACAACGTGCAGCACTTCTAGGTTGTACTACCACTTGTGCCCTTCCTTACTATTG (SEQ ID NO: 47) |
| tRNA/miR-155/GFP-siRNA | Fow-AGTAATTTACGTCGACGAGGCTTGCTGAAGGCTGTATGCTGGTTGTACTCCAGCTTGTGCCCGTTTTGGCCACTGACTGACGG (SEQ ID NO: 48)<br>Rev-CGGCCGCAACCATCGACGTCGAGTGCTAGTAACAGGCCTTGTGTCCTGGTTGTACTCCATTGTGCCCGTCAGTCAGTGGCCAA (SEQ ID NO: 49) |
| OnRS/MGA5 | Fow-GTTAGAGCAGCGGCCGGGATCCCGACTGGCGAGAGCCAGGTAACGAATGGATCCGTGGACCGGCCAGCTGTGAG (SEQ ID NO: 50)<br>Rev-GAACCTGTGACCCGCGGGTGGACCGGGCCCCACAACGTGCAGCA (SEQ ID NO: 51) |
| OnRS/MGA3 | Fow-GTTAGAGCAGCGGCCGGTGGACCGGCCAGCTGTGAG (SEQ ID NO: 52)<br>Rev-GAACCTGTGACCCGCGGGGATCCATTCGTTACCTGGCTCTCGCCAGTCGGGATCCGTGGACCGGGCCCCACAACGTGCAGCA (SEQ ID NO: 53) |
| (c) Primers used for RT-qPCR experiments | |
| Utility | Primer sequences (5'→3') |
| Universal rev | GCGCTAAGGCACGCGGTG (SEQ ID NO: 54) |
| U74 | RT-GTCGTATCCAGTGCAGGGTCCGAGGTATTCGCACTGGATACGACAATTGT (SEQ ID NO: 55)<br>Fow-CCTGTGGAGTTGATCCTAGTCTGGGTG (SEQ ID NO: 56) |
| miR-124 | RT GTCGTATCCAGTGCAGGGTCCGAGGTATTCGCACTGGATACGACGGCATT (SEQ ID NO: 57)<br>Fow-GCGCTAAGGCACGCGGTG (SEQ ID NO: 54) |

TABLE 1b-continued

| | |
|---|---|
| GFP-siRNA | RT-GTCGTATCCAGTGCAGGGTCCGAGGTATTCGCACTGGATACGACGGGCAC (SEQ ID NO: 58)<br>Fow-GCGCGCAGTTGTACTCCAGCTT (SEQ ID NO: 59) |
| GFPm RNA | Fow-ACGTAAACGGCCACAAGTTC (SEQ ID NO: 60)<br>Rev-AAGTCGTGCTGCTTCATGTG (SEQ ID NO: 61) |

(b) Oligonucleotides used for plasmid construction and qPCR analysis

| Plasmids | Primer sequences (5'→3') |
|---|---|
| PPIA | Fow-CCTAAAGCATACGGGTCCTG (SEQ ID NO: 62)<br>Rev-TTTCACTTTGCCAAACACCA (SEQ ID NO: 63) |
| 18s | Fow-GTAACCCGTTGAACCCCATT (SEQ ID NO: 64)<br>Rev-CCATCCAATCGGTAGTAGCG (SEQ ID NO: 65) |

Expression of Chimeric RNAs in *E. coli.*

Chimeric RNAs were expressed in HST08 on a large scale as described (13,14,17). Total RNAs were isolated from *E. coli* using the Tris-HCl-saturated phenol extraction method, quantitated with a NanoDrop 2000 spectrophotometer (Thermo Fisher Scientific, Rockford, Ill.) and analyzed by denaturing urea (8 M) polyacrylamide (8%) gel electrophoresis (PAGE). All images were acquired with ChemiDoc MP Imaging System (Bio-Rad, Hercules, Calif.). Intensities of bands were used to provide a rough estimation of relative levels of recombinant ncRNAs present in the total RNAs.

Purification of Recombinant ncRNAs.

Purification of recombinant ncRNAs was conducted with a NGC QUEST 10PLUS CHROM fast protein liquid chromatography (FPLC) System (Bio-Rad). Separation of recombinant ncRNAs from total RNAs was achieved on a UNO Q6 anion-exchange column (Bio-Rad), which was first equilibrated with Buffer A (10 mM sodium phosphate, pH=7.0) at a flow rate 5.0 mL/min for 0.5 min, followed by a gradient elution at the same flow rate, 0-56% Buffer B (Buffer A plus 1 M sodium chloride) in 0.5 mM, 56% Buffer B for 2 mM, 56-65% Buffer B in 10 mM, and then 100% Buffer B for 2 mM, 100-0% Buffer B in 0.5 mM and 100% Buffer A for 5 mM. FPLC traces were monitored at 260 nm using a UV/Vis detector. Peak areas were employed to estimate the relative levels of recombinant ncRNAs within the total RNAs, which agrees with those determined by urea-PAGE analyses. After analyzed on a denaturing PAGE gel, the fractions containing pure ncRNAs were pooled. Recombinant ncRNAs were precipitated with ethanol, reconstituted with nuclease-free water, and then desalted and concentrated with Amicon ultra-2 mL centrifugal filters (30 KD; EMD Millipore, Billerica, Mass.). The only exception was OnRS/MGA that was reconstituted with 10 mM HEPES (pH=7.4) buffer. The quantity of purified ncRNAs was determined using NanoDrop and the quality was validated by PAGE analysis before other experiments.

Deep Sequencing of Small RNAs and Data Analysis.

A549 cells were transfected with 50 nM FPLC-purified OnRS/miR-124 and tRNA/mir-34a (OnRS), and ES-2/GFP cells were transfected with OnRS/Neg and OnRS/GFP-siRNA using Lipofectamine 2000 (Life Technologies). Total RNAs were isolated using a Direct-zol RNA extraction kit (Zymo Research, Irvine, Calif.) at 48 h post-transfection, and small RNA libraries were generated using the Illumina Truseq™ Small RNA Preparation kit (Illumina, San Diego, Calif.) according to the instructions. The purified cDNA library was used for cluster generation on Illumina's Cluster Station and then sequenced on Illumina GAIIx following vendor's instructions. Raw sequencing reads (40 nt) were obtained using Illumina's Sequencing Control Studio software version 2.8 (SCS v2.8) following real-time sequencing image analysis and base-calling by Illumina's Real-Time Analysis version 1.8.70 (RTA v1.8.70). The extracted sequencing reads were used for the standard sequencing data analysis by following a proprietary pipeline script, ACGT101-miR v4.2 (LC Sciences, Houston, Tex.)(20,21). Cells were treated in triplicate and sequenced separately.

Reverse Transcription Quantitative Real-Time PCR (RT-qPCR).

Cells were transfected with various doses of recombinant ncRNAs and harvested at particular time points. Total RNAs were isolated using Direct-zol RNA isolation kit (Zymo Research), and RNA concentrations were determined using NanoDrop 2000 spectrophotometer. RT was conducted with NxGen M-MuLV reverse transcriptase (Lucigen, Middleton, Wis.), and qPCR analysis was carried out on a CFX96 Touch real-time PCR system (Bio-Rad) using quantitative RT-PCR Master mix (New England Biolabs), as described(17,22). Levels of miRNAs were normalized to U74, and mRNA levels were normalized to PPIA. Gene specific primers were shown in Table 1. Each experiment was conducted in triplicate and each sample was measured 2-3 times. Similar results were obtained when the study was repeated.

Western Blots.

A549 cells were transfected with 100 nM OnRS/miR-124 or OnRS/Neg and harvested after 48 h. Cell lysates were prepared with RIPA lysis buffer (Rockland Immunochemical Inc., Limerick, Pa.) consisting of complete protease inhibitor cocktail (Roche, Nutley, N.J.). Protein concentrations were determined using the BCA Protein Assay Kit (Thermo Fisher Scientific). Whole-cell proteins (40 μg per lane) were separated on 10% SDS-PAGE gel, and electrophoretically transferred onto PVDF membranes (Bio-Rad). Membranes were then incubated with selective antibody against P-STAT-3, STAT-3 (Cell Signaling Technology, Danvers, Mass.) or GAPDH (Santa Cruz Biotech Inc., Texas, Tex.), and subsequently with peroxidase anti-rabbit (Jackson ImmunoResearch Inc., West Grove, Pa.) or anti-mouse IgG (Cell Signaling). The membranes were then incubated with ECL substrates (Bio-Rad), and images were acquired with ChemiDoc MP Imaging System (Bio-Rad). Cells were treated in triplicate and the same results were obtained when the whole study was repeated.

Apoptosis Assay.

The apoptosis assay was performed by using a FACS Annexin V assay kit (Trevigen, Inc., Gaithersburg, Md., USA) following the manufacturer's protocol. Briefly, A549 cells were transfected with 100 nM recombinant ncRNAs, harvested at 72 h post-transfection, incubated with Annexin V-FITC conjugate and propidium iodide solution, and then the samples were analyzed on a FACScan flow cytometer (BD Biosciences, San Jose, Calif.). Data analysis was performed using Flowjo (Ashland, Oreg.). Cells were treated in triplicate and similar results were obtained when the whole experiment was repeated.

MTT Assay.

A549 cells were transfected with 20 or 100 nM chimeric RNAs. At 72 h post-transfection, cell viability was determined using MTT as we described previously (23). Cells were treated in triplicate and similar results were obtained when the whole study was repeated.

Real-Time Cell Growth Analysis.

A549 cells were seeded 40,000/well on an 8-well E-Plate and treated with 20 or 100 nM recombinant ncRNA 24 h later. Cell growth was monitored using an iCELLigence system (ACEA Biosciences, San Diego, Calif.). Similar results were obtained when the whole experiment was repeated for three times.

In Vitro Knockdown of GFP.

ES-2/GFP cells were seeded 8,000 cells/well on a 24-well plate and transfected with 5 or 15 nM FPLC-purified chimeric RNAs at 24 h later. The fluorescence was monitored with an Olympus IX81 microscope (Olympus, Center Valley, Pa.) at 24h, 48h and 72h post-transfection. All images were acquired using the same settings at the same time. At the end of the study, total RNAs were isolated from the cells and subject to RT-qPCR evaluation of GFP mRNA and siRNA levels. Cells were treated in triplicate, and similar results were obtained when the whole experiment was repeated.

In Vivo Knockdown of GFP.

All animal procedures were approved by the Institutional Animal Care and Use Committee at UC Davis. Six- to seven-week-old male GFP-transgenic (C57BL/6-Tg(CAG-EGFP)1Osb/J) mice (24) (The Jackson Laboratory, Bar Harbor, Me.) were injected i.v. with 75 µg FPLC-purified OnRS/Neg (N=3) or OnRS/GFP-siRNA (N=4) after formulated with in vivo-jetPEI (Polyplus-transfection Inc., New York, N.Y.) each day for consecutive 3 days. Three days after the last injection, mice were sacrificed and liver tissues were collected. Frozen sections (8 µm) were prepared after embedded in Tissue-Tek O.C.T. (Sakura Finetek, Torrance, Calif.) and examined directly using a Zeiss Axio Observer.z1 Microscope coupled to a Zeiss LSM 710 Scanning Device (Zeiss, Oberkochen, Germany). Different batches of sections (8 µm) were fixed with 4% paraformaldehyde (Sigma-Aldrich, St. Louis, Mo.) and stained with 1 µg/mL 4',6-diamidino-2-phenylindole (DAPI; Sigma-Aldrich). GFP fluorescence and DAPI-stained nuclei images were recorded with confocal microscope sequentially and then merged together.

In addition, liver tissues were subject to RNA isolation and RT-qPCR analyses for GFP mRNA and siRNA levels against 18S and U74 was used as control, respectively. Gene specific primers were presented in Table 1.

Malachite Green (MG) Aptamer Binding Assays.

Absorbance scanning was performed from 550 nm to 700 nm using a SpectraMax Microplate Reader (Molecular Devices, Sunnyvale, Calif.) after 32 µg purified ncRNAs or 80 µg total RNAs were incubated with 10 µM MG in 100 mM KCl, 5 mM $MgCl_2$, and 10 mM HEPES (pH=7.4) buffer in a total volume of 100 µL. Fluorescent intensity was determined at 630/650 nm (excitation/emission) with the same SpectraMax Microplate Reader for purified ncRNAs (32 µg) or total RNAs (80 µg) in the absence and presence of MG (10 µM). To establish the linearity of MGA-bound MG fluorescent intensity vis-à-vis MG and MGA concentrations, the intensities of fluorescence were examined when 2.08 µM OnRS/MGA5 was exposed to 0-10 µM MG and 10 µM was incubated with 0-5.2 µM OnRS/MGA5, respectively, in 10 mM HEPES (pH=7.4) buffer in a total volume of 100 µL. Each assay was carried out in triplicate, and all experiments were repeated at least once that showed similar results.

Serum RNase Activity Assay.

Serum specimens from IRB-approved, prospectively-collected UC Davis Pancreas Registry bank were utilized. The serum has been processed uniformly within 4 h of blood collection, aliquoted and stored in a −80 OC freezer till usage with minimal freeze-thaw cycle. A total of 20 patients' serum from 10 pancreatic ductal adenocarcinoma (PDAC) (5 early-stage PDAC (American Joint Committee of Cancer, Stages 1 & 2)) and 10 benign/normal pancreas cases (5 chronic pancreatitis and 5 normal pancreases) were selected. The PDAC cases consisted of 4 males and 6 females, benign/normal of 5 males and 5 females. Age ranges were 51 to 80 (mean=67 y/o) in the PDAC and 37 to 85 (mean=60 y/o) in benign/normal groups. A normal pooled human serum sample (Fisher Scientific Inc., Waltham, Mass.), human recombinant RNase A (Novoprotein, Summit, N.J.) and human recombinant angiogenin (R&D Systems, Minneapolis, Minn.) were used for method development.

To evaluate the change in MGA-bound MG fluorescent intensity in relationship to incubation time (0-30 mM) after exposure to human serum, 2.08 µM OnRS/MGA5 was incubated with 0.4 or 2.0 µL normal pooled human serum in 10 mM HEPES (pH=7.4) buffer in a total volume of 90 µL, and then fluorescence was determined after the addition of 10 µL MG to a final 10 µM concentration. To assess the protection of MGA by in vivo-jetPEI, 2.08 µM OnRS/MGA5 and 1.0 µL pool human serum were incubated for 0-60 min. To determine the dose response, various volumes of the pooled human serum (0.01-10 µL) or concentrations of recombinant human RNase A (0-$10^{-4}$ µg/µL) and angiogenin (0-$10^{-2}$ µg/µL) were incubated with 2.08 µM OnRS/MGA5 for 10 min. To define the influence of RNase inhibitor, the pooled human serum (0, 1, 2 and 5 µL) was incubated with 2.08 µM OnRS/MGA5 for 10 mM, with or without 0.4 U/µL RNase inhibitor (Lucigen, Middleton, Wis.). Each incubation reaction was carried out in triplicate, and all experiments were repeated at least once that offered consistent findings.

Based upon the linearity of fluorescent intensity over MG and MGA concentrations, incubation time and quantity of human sera, 0.4 µL patient serum sample was incubated with 2.08 µM OnRS/MGA5 in 10 mM HEPES (pH=7.4) buffer in a total volume of 90 µL at 37° C. for 5 min and then 10 µL MG was added to give 10 µM final concentration for the determination of fluorescence at 630/650 nm (excitation/emission). Serum RNase activity was calculated as the change in fluorescent intensity over time and quantity of serum sample, i.e., ∆A.U./min/µL. Each patient sample was assayed twice with <10% variations.

Statistical Analysis.

Values were expressed as mean±SD. According to the number of groups and variances, data were analyzed with unpaired Student's t-test, or one-way or two-way ANOVA (GraphPad Prism, San Diego, Calif.). Difference was considered as significant for P-value less than 0.05 (P<0.05).

Results

An OnRS is Developed to Achieve High-Yield Production of Recombinant RNAi Agents.

We intended to bioengineer tRNA fusion pre-miRNA (tRNA/mir) agents in common strains of bacteria (FIG. 1a) on a large scale, i.e., milligrams of recombinant ncRNAs from 1 L bacterial culture. A series of plasmids were created and employed to transform E. coli. Surprisingly, we found that the levels of recombinant pre-miRNA chimeras expressed/accumulated in HST08 E. coli were largely variable when the same tRNA scaffold was used. The majority of tRNA/pre-miRNA chimeras were unfortunately not accumulated or at a negligible level (FIG. 1a). Use of other E. coli strains still offered no or even lower levels of target ncRNA chimeras (data not shown). Nevertheless, given the findings that tRNA/mir-34a was accumulated to a high level in bacteria (e.g., ~15-20% of total RNAs) and chimeric tRNA/mir-34a was stable and selectively processed to mature hsa-miR-34a in various types of human carcinoma cells, we hypothesized that tRNA/mir-34a might be developed as an OnRS over the tRNA scaffold towards a consistent high-level production of target miRNAs (FIG. 1b).

We thus took up the challenge to assemble miR-124 using the OnRS (tRNA/mir-34a) platform, noticing that miR-124 differs much from miR-34a in size (20 vs. 22 nt) and arm of origin (3' vs. 5'). We replaced the 22-nt miR-34a-5p with 20-nt miR-124-3p and substituted their complementary sequences accordingly (Table 1), which indeed offered a high-level expression of OnRS/miR-124 chimera in HST08 E. coli (FIG. 1b). Recombinant OnRS/miR-124 was then readily purified to a high degree of homogeneity (>99%) using the anion-exchange FPLC method (FIG. 1c). Likewise, the OnRS was able to assemble other miRNAs (e.g., 21-nt miR-27b and 22-nt miR-22, etc.; unpublished data) and a 22-nt scrambled RNA sequence (chimeric RNA was named OnRS/Neg and used as a control in the following studies; Table 1), which were all consistently produced in HST08 E. coli at high yields and on a large scale, i.e., >15% of OnRS/miRNAs in total RNAs and >1.5 mg of FPLC-purified OnRS/miRNAs from 0.5 L bacterial culture at all times.

We further evaluated if we could utilize this OnRS-based approach to produce milligrams of functional siRNA agents in 1 L E. coli culture. A 22-nt GFP siRNA (25) was chosen as a model siRNA to assemble chimeric OnRS/GFP-siRNA (Table 1). In contrast to a minimal level of accumulation in bacteria when tRNA/mir-155 was utilized as a carrier, the use of OnRS (tRNA/mir-34a) provided a consistent high-level expression of OnRS/GFP-siRNA (FIG. 1b) and facilitated the FPLC purification of recombinant ncRNAs (FIG. 1d). As a result, we were able to produce 1.5-2.0 mg, >98% pure OnRS/GFP-siRNA from 0.5 L bacterial culture every time. These results indicate that target miRNA/siRNA agents can be assembled by using OnRS-based platform to offer a consistent high-level production of chimeric ncRNAs in bacteria.

Target miRNAs/siRNAs are Selectively Released from Chimeric ncRNAs in Human Cells while tRNA Scaffold is Processed to tRNA Fragments (tRFs).

Figure 2:
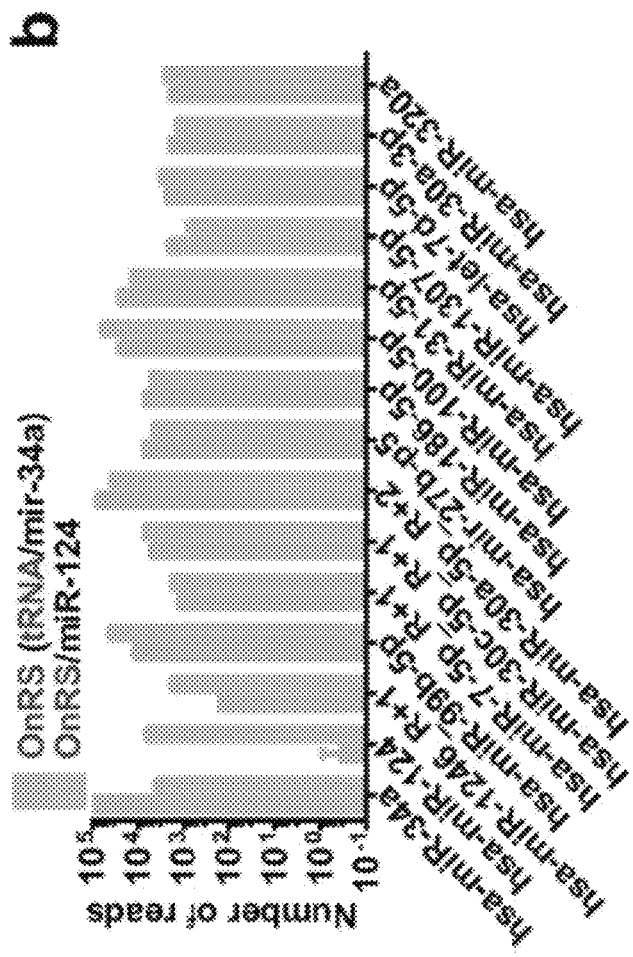
FIG. 2 illustrates the fate of recombinant ncRNAs in human cells. (a and b) Unbiased deep sequencing study revealed that OnRS-carried miR-124 and GFP-siRNA were precisely processed to target small RNAs, leading to 3 orders of magnitude increase in miR-124 in A549 cells and GFP siRNA in ES-2/GFP cells, respectively. Note the presence of miRNA and siRNA isoforms as well as corresponding passenger strands and other small RNAs at much lower levels. In contrast, the levels of other cellular miRNAs showed no or minor changes. Values are mean±SD of triplicated treatments that were sequenced separately. (c and d) Mapping major cellular tRFs derived from OnRS/miR-124 versus OnRS (tRNA/mir-34a) in A549 cells and OnRS/GFP-siRNA versus OnRS/Neg in ES-2/GFP cells, respectively. Shown are the mean numbers of reads of triplicated treatments. 3,000 reads was used as a cut off.
Figure 2:
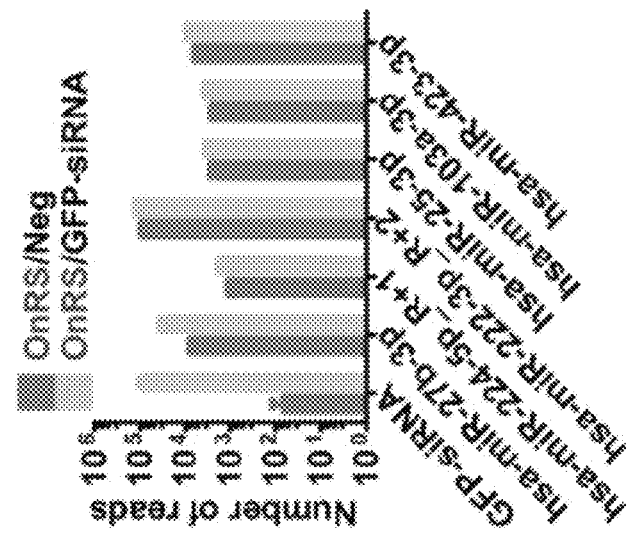
Figure 2:
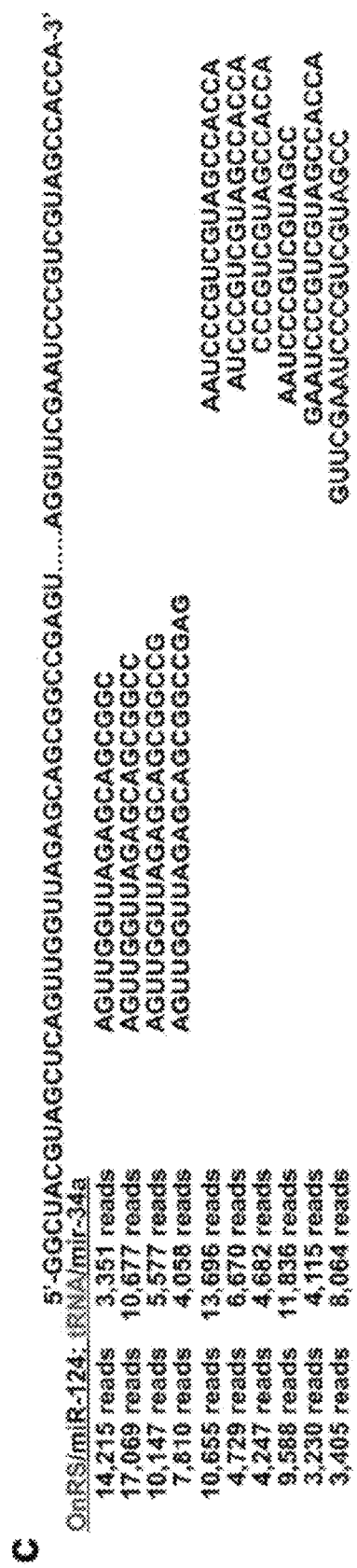
Figure 2:
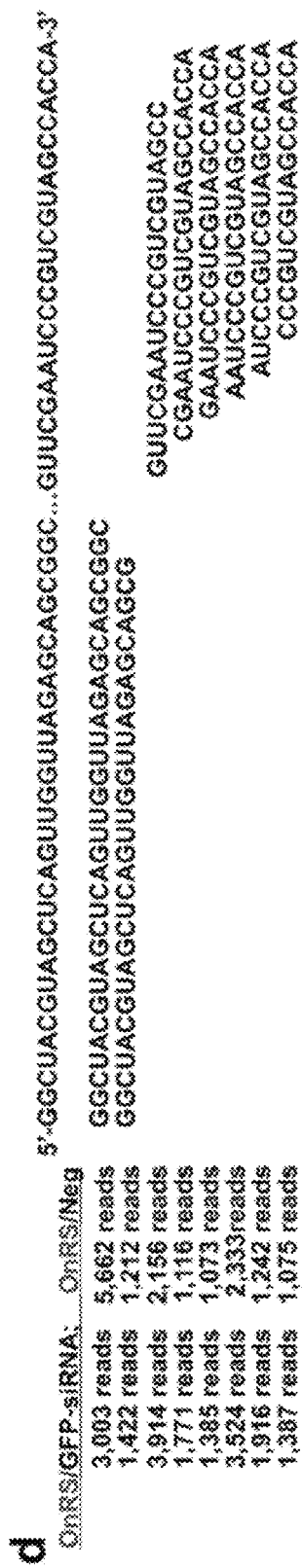

Next we assessed if mature miR-124 could be selectively produced from OnRS/miR-124 in human cells. An unbiased deep sequencing study was conducted after the preparation of small RNAs library from human lung carcinoma A549 cells at 48 h post-transfection with OnRS/miR-124 and OnRS (tRNA/mir-34a). The data showed that OnRS/miR-124 was selectively processed to large numbers (5,613±975 reads) of 20-nt miR-124 in A549 cells (FIG. 2a). In contrast, there was 0±1 reads of mature miR-124 identified in A549 cells treated with tRNA/mir-34a (OnRS) that actually offered 22-nt miR-34a. Other miR-124 isoforms including those of 21 nt in length, as well as some passenger strands, were also noted whereas at much lower levels. In addition, OnRS/miR-124 had no or relatively much smaller influence on other cellular miRNAs including the hsa-mir-34a-p3 fragment (FIG. 2a), while the tRNA scaffold was degraded to tRFs that actually exhibited similar patterns between OnRS/miR-124- and tRNA/mir-34a-treated cells (FIG. 2c).

Likewise, we conducted the unbiased deep sequencing analyses of cellular small RNAs in human ES-2/GFP cells at 48 h post-transfection with FPLC-purified OnRS/GFP-siRNA and OnRS/Neg. The data showed that GFP-siRNA levels were about 1,000-fold higher in ES-2/GFP cells treated with chimeric OnRS/GFP-siRNA than the control OnRS/Neg (FIG. 2b), which was mainly attributable to the increase in 22-, 23- and 21-nt isoforms and accompanied by lower levels of passenger strands. It was also noted that OnRS/Neg was indeed processed to a number of scrambled RNAs at 22-23 nt in length, but at much lower levels, which might be related to a lower stability of the scrambled RNAs or insufficient processing. Nevertheless, there were no or minimal differences in the levels of other cellular miRNAs between OnRS/GFP-siRNA- and OnRS/Neg-treated cells. Furthermore, the tRF patterns were also similar between OnRS/GFP-siRNA and OnRS/Neg-treated cells (FIG. 2d), despite that overall tRF levels were much lower in ES-2/GFP cells than A549 cells. Together, these results support the utility of OnRS for "stealth delivery" of target miRNAs and siRNAs into human cells beyond high-yield production of the chimeric ncRNAs in bacteria and the use of OnRS/Neg as a control to assess OnRS/siRNA activities.

OnRS-Carried miR-124 is Biologically/Pharmacologically Active in Controlling Target Gene Expression and Cancer Cellular Processes.

Then we evaluated the bioactivities of OnRS-carried miR-124, as miR-124 is known to regulate a number of target genes such as the oncogenic signal transducer and activator of transcription 3 (STAT3), enhance apoptosis, and inhibit cell proliferation (26-28). Consistent with deep sequencing data, selective stem-loop RT-qPCR analyses showed that mature miR-124 levels were around 1000-fold higher in A549 cells from day 1 to 4 after transfection with OnRS/miR-124, compared with OnRS/Neg (FIG. 3a). Increase in miR-124 in OnRS/miR-124-treated A549 cells led to a 60% reduction of STATS protein levels (FIG. 3b), and 1- to 2-fold greater degrees of early and late apoptosis as well as necrosis (FIG. 3c). Consequently, OnRS/miR-124 exhibited significantly greater antiproliferative activity than OnRS/Neg, as demonstrated by MTT assay and using a Real-Time Cell Analyzer (FIG. 3d-3e). These results demonstrate that chimeric OnRS/miR-124 is biologically/pharmacological active in regulating miR-124 target gene expression and controlling cancer cell growth after being processed to mature miR-124 in the cells.

OnRS-Carried GFP siRNA is Effective in Knocking Down GFP Expression In Vitro and In Vivo.

We also assessed the effectiveness of OnRS-carried GFP siRNA using GFP-expressing ES-2 cells and GFP-transgenic mouse models. In ES-2/GFP cells, OnRS/GFP-siRNA significantly suppressed the GFP fluorescence intensity and mRNA levels at 72 h post-transfection (FIG. 4a-4b), which was associated with 3 orders of magnitude increase in GFP siRNA levels (FIG. 4c). We then treated GFP-transgenic mice (24) with in vivo-jetPEI-formulated OnRS/GFP-siRNA. Compared to the GFP-transgenic mice treated with the same doses of in vivo-jetPEI-formulated OnRS/Neg, there was a remarkable reduction of hepatic GFP fluorescence intensity (FIG. 4d-4e) and mRNA levels (FIG. 4l) in GFP-transgenic mice treated with OnRS/GFP-siRNA, which was linked to an over 3,000-fold increase in GFP siRNA levels. These data indicate that chimeric GFP-siRNAs produced on large scale using the OnRS cargo are effective agents for in vitro and in vivo RNAi applications.

Utility of OnRS for High-Level Production of Active RNA Aptamer Chimeras in Bacteria.

Figure 6:
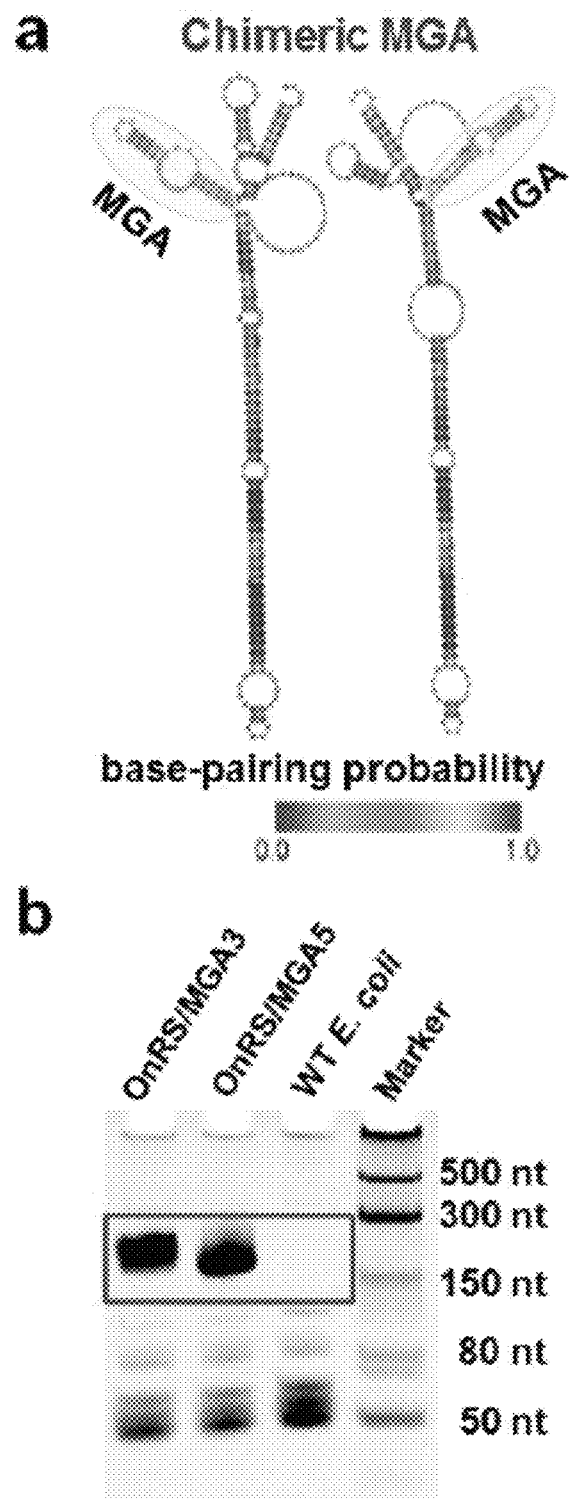
FIG. 6 illustrates high-yield large-scale production of chimeric MGA sensor that produces strong and selective fluorescence upon binding to MG. (a) MGA may be inserted at the 5' or 3' end of the OnRS scaffold to offer OnRS/MGA5 and OnRS/MGA3, respectively (SEQ ID NOS 84 and 84, respectively, in order of appearance). The heat color gradation indicates the base-pairing probability from 0 to 1. (b) A consistent high-level expression of chimeric MGA in *E. coli*, e.g., over 50% of OnRS/MGA5 and OnRS/MGA3 in total RNAs. (c) Representative FPLC traces of OnRS/MGA5 during FPLC purification. Insert is urea-PAGE analysis of the collected RNA fractions (1, 2 and 3) eluted at 10.6 min. (d) Binding to OnRS/MGA5 and OnRS/MGA3 led to a shift of the wavelength of MG maximum absorbance from 618 to 630 nm. The same shift was observed when FPLC-purified OnRS/MGA and total RNAs isolated from OnRS/MGA-expressing bacteria were used. The SEPHADEX™-purified aptamer (OnRS/Seph) and corresponding total RNAs were used as additional controls. (e) Strong and selective fluorescence was shown when MG bound to OnRS/MGA5 or OnRS/MGA3. The same results were obtained when using FPLC-purified OnRS/MGA and OnRS/MGA-containing total RNAs.
Figure 6:
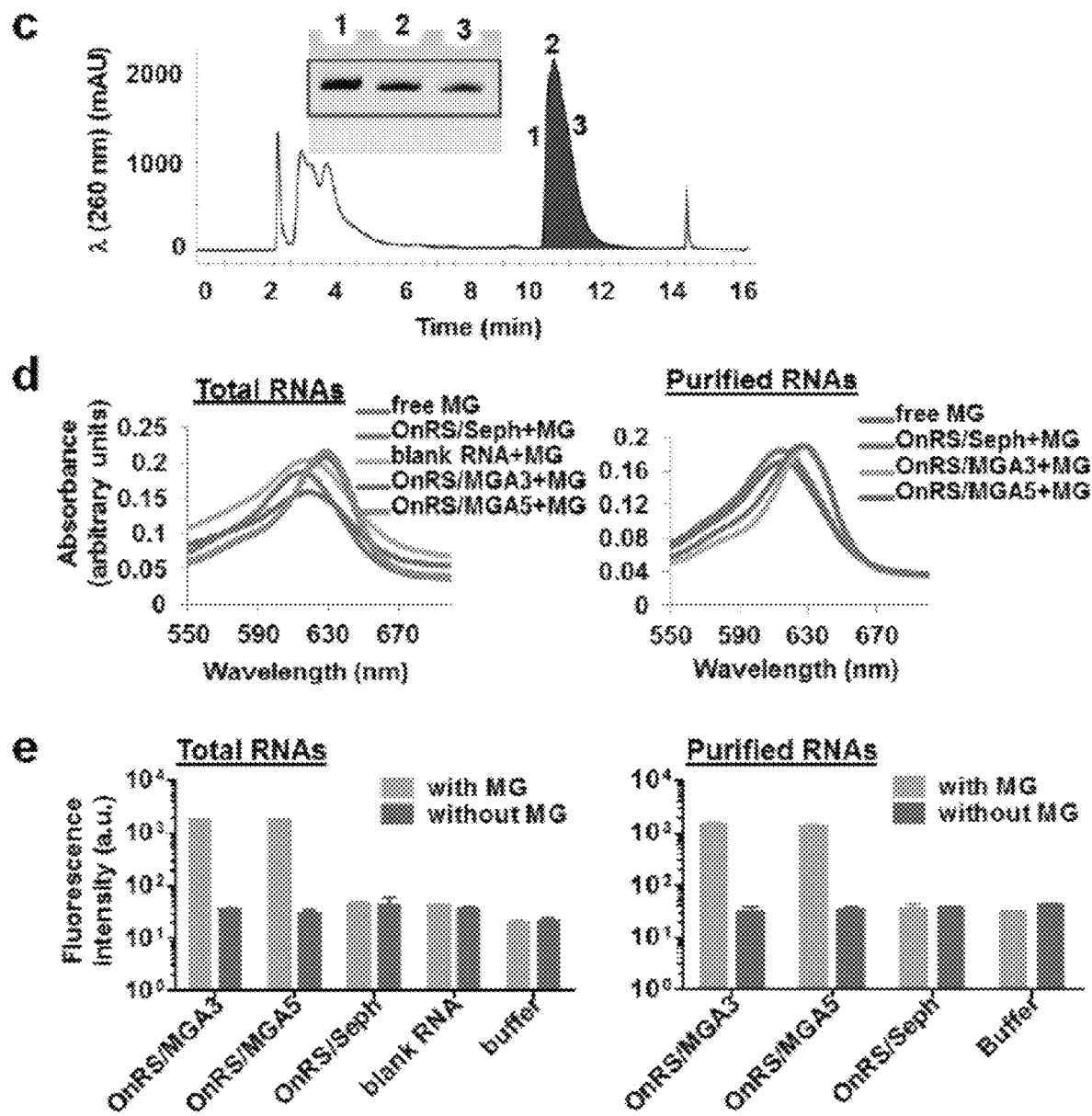

Encouraged by these findings, we further challenged the potential applications of OnRS to the production of functional RNA aptamers. A malachite green aptamer (MGA) (9) was chosen as a model aptamer and inserted at the 5' and 3' of miR-34a to offer OnRS/MGA5 and OnRS/MGA3, respectively (FIG. 6a). Both chimeras were revealed to be expressed at surprisingly high levels in bacteria, i.e., over 50% of OnRS/MGA in total RNAs (FIG. 6b). Thus we could use FPLC (FIG. 6c) to easily purify 5-6 mg OnRS/MGA from 15-20 mg total RNAs isolated from 0.5 L bacterial culture at all times.

Consistent with the reported property of MGA (9), we found that the wavelength of MG maximum absorbance was shifted from 618 to 630 nm upon binding the label-free, chimeric OnRS/MGA sensor (FIG. 6d). Interestingly, the use of FPLC-purified OnRS/MGA or total RNAs isolated from OnRS/MGA-expressing bacteria gave the same shift in wavelength, whereas a SEPHADEX™ aptamer (OnRS/Seph) and corresponding total RNAs did not, indicating the selectivity of MGA-MG interactions. The function of OnRS-carried MGA was further demonstrated by a strong fluorescent intensity at 630/650 nm (excitation/emission) upon binding MG (FIG. 6e). In contrast, label-free OnRS/MGA itself did not exhibit any fluorescence, and only minimal basal-level MG fluorescent intensity was shown in the absence or presence of non-MGA-containing total RNAs and HPLC-purified OnRS/Seph (FIG. 6e), supporting the specificity of MGA-bound-MG fluorescence. These results demonstrate that OnRS is also powerful for high-yield production of functional RNA aptamers of interests.

Application of Label-Free, OnRS-Carried Malachite Green Aptamer Sensor to Determine Serum RNase Activities Among Human Pancreatic Cancer Patients.

Figure 7:
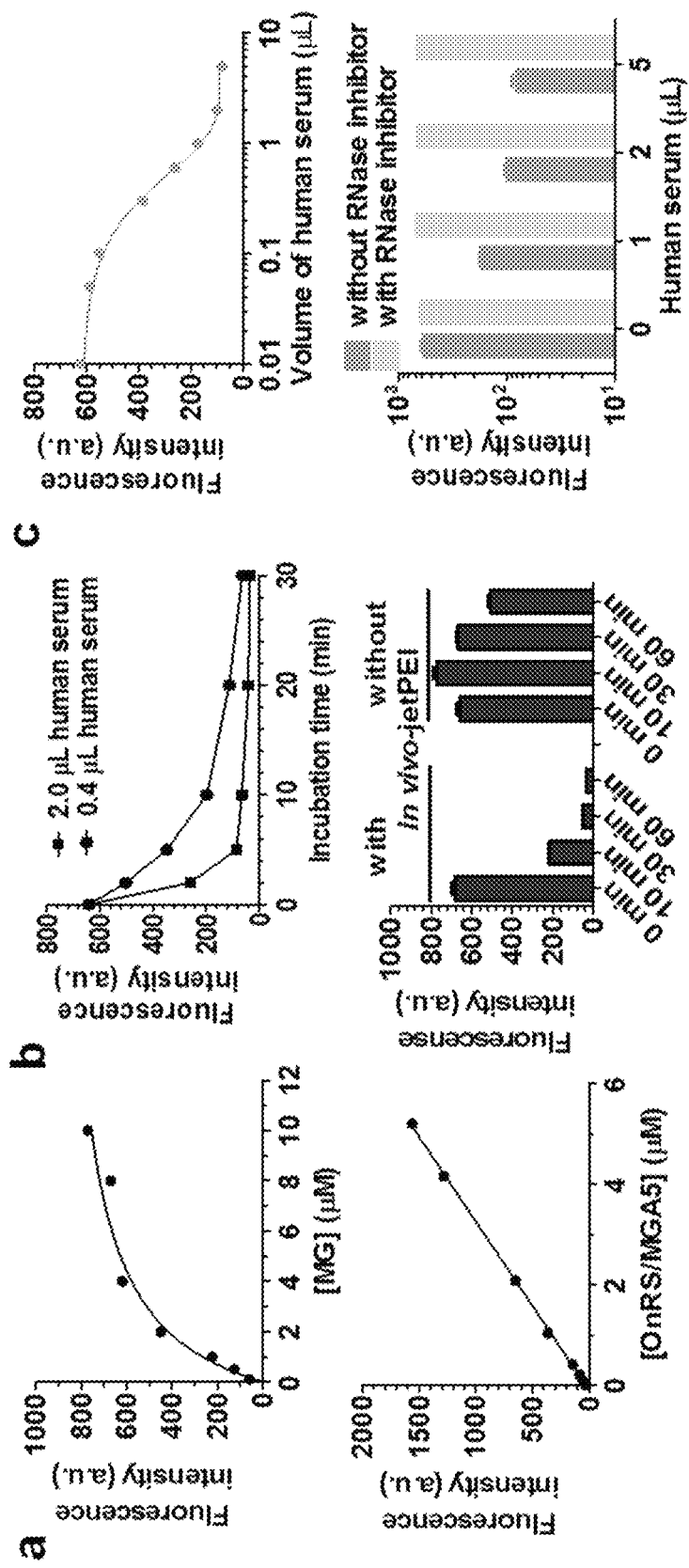
FIG. 7 illustrates method to determine RNase activity using chimeric MGA sensor. (a) Change in MGA-bound-MG fluorescent intensity with the increase in MG and MGA concentrations. Corresponding MGA and MG concentrations were fixed at 1.6 µg/mL and 10 µM, respectively. (b) The fluorescent intensity was decreased over time when incubated with human serum, and in vivo-jetPEI formulated OnRS/MGA was protected from cleavage by serum RNases. (c) Dose response was obvious for the exposure to human serum RNases and the intensity of OnRS/MGA-bound MG fluorescence, and addition of RNase inhibitor completely blocked the cleavage of OnRS/MGA by serum RNases. (d) OnRS/MGA was much more susceptible to human RNase A (10 min incubation) than angiogenin (RNase 5; 30 min incubation). (e) Human pancreatic cancer patients showed significantly higher serum RNase activities than benign/normal patients, as determined by the decrease in MGA-bound MG fluorescence intensity (ΔA.U./min/µL). N=10 in each group. OnRS/MGA5 was used in this study.
Figure 7:
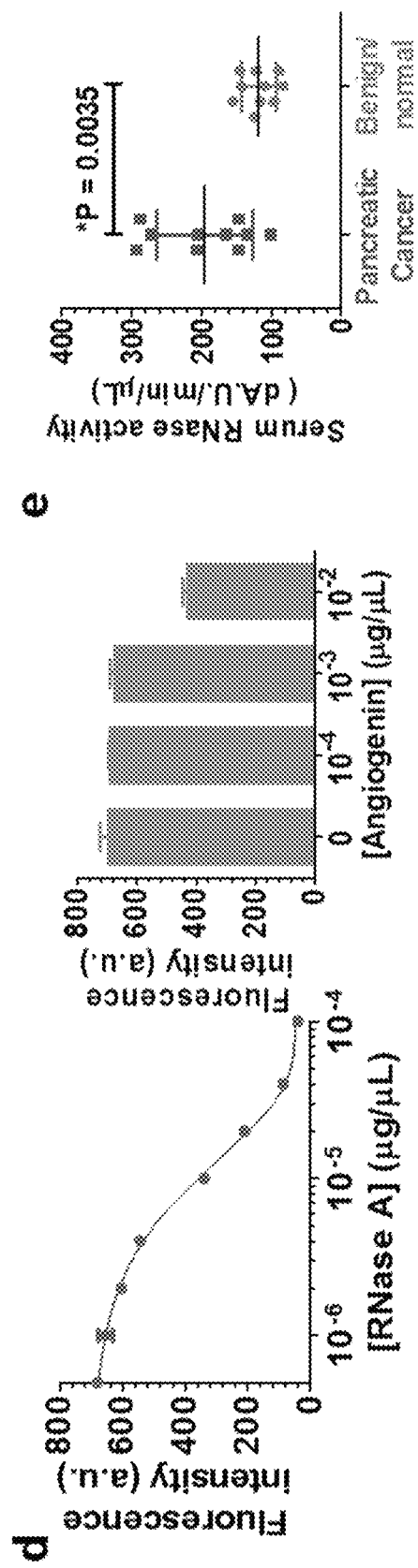

Given the unique property of MGA-bound MG in exhibiting the fluorescence, we further developed an OnRS/MGA-based RNase activity assay and employed the label-free chimeric OnRS/MGA to investigate and compare serum RNase activities between human PDAC and benign (including chronic pancreatitis)/normal patients because pancreatic cancer patients were shown to have much higher serum RNase activities (29). The intensity of the fluorescence increased with MG concentrations and nearly plateaued at 10 µM MG when OnRS/MGA concentration was fixed at 2.08 µM (or 0.16 µg/µL), while a good linear range was shown for 0.04-5.2 µM OnRS/MGA when MG concentration was fixed at 10 µM (FIG. 7a). As expected, the intensity of OnRS/MGA-bound MG fluorescence was decreased over time (FIG. 7b) when OnRS-carried MGA was cleaved by the RNases in a normal pooled human serum sample, and the response was dependent upon the doses of human sera (FIG. 7c) while sera themselves did not have any significant fluorescence. Indeed, use of in vivo-jetPEI provided good protection against the decrease in fluorescent intensity over time, and addition of RNase inhibitor completely blocked the cleavage of OnRS/MGA by serum RNases. These data indicate that OnRS/MGA may be utilized to directly determine RNase activities.

To define the role of RNase A (the major form RNase in human serum) in the cleavage of chimeric ncRNAs, we directly compared the susceptibility of OnRS-carried MGA to cDNA-expressed RNase A and angiogenin (RNase 5). As manifested by the degrees of change in the intensity of MGA-bound MG fluorescence, 2.08 µM OnRS/MGA was completely cleaved by $5.0 \times 10^{-5}$ µg/µL RNase A in 10 min, whereas only 40% OnRS/MGA was degraded by 500-fold higher concentration (0.01 µg/µL) of angiogenin in 30 min. Since RNase A is the major form of RNase in human serum (30), this assay would mainly indicate pancreas-derived RNase A activity in human serum. Therefore, we utilized OnRS/MGA to evaluate the RNase activities in a set of serum samples prospectively collected from PDAC and benign/normal patients. The data showed that serum RNase activities (ΔA.U./min/µL) were significantly (P<0.01) higher in PDAC (196±22) than benign/normal (118±8) patients. These results implicate that chimeric MGA sensor produced using the OnRS platform could be useful for determination of RNase activities.

Discussion

A general approach has been established for a consistent, cost-effective production of multiple to tens of milligrams of chimeric ncRNAs in 1 L culture of a common strain of E. coli, bearing various types of small RNAs of interests. The OnRS used in this platform is based upon the tRNA fusion pre-miRNA-34a that is resistant to nucleolytic digestion in bacteria and thus accumulated to significantly high level (e.g., >15% of total RNAs) for an easy purification with the anion-exchange FPLC method. The miR-34a-5p/miR-34a-3p duplex within the OnRS cargo may be replaced by any target double-stranded small RNAs such as siRNA or miRNA/miRNA* duplex (FIG. 1b) to achieving high-yield production of corresponding chimeric siRNA or miRNA agents, as exemplified by successful production of >1.5 mg of OnRS/miR-124, OnRS/GFP-siRNA and control OnRS/Neg chimeras from 0.5 L bacterial culture in this report. In addition, single-stranded small RNAs such as RNA aptamers can be sprouting at particular sites on OnRS to offer the aptamer chimeras (FIG. 5a), which are nicely demonstrated by the assembling of OnRS/MGA5 and OnRS/MGA3 sensors. The robustness and versatility of OnRS-based platform is also supported by successful production of other target RNA agents (e.g., miR-27b, miR-22, and a vascular endothelial growth factor (VEGF) aptamer, etc.; unpublished data), whereas its application to bioengineer other types of biological RNAs such as catalytic RNAs (ribozymes) for biotransformation and guide RNAs (gRNAs) for genome editing warrants further investigations.

Chimeric OnRS/miRNAs and OnRS/siRNAs can act as "pro-drugs" for the "delivery" of target RNAi agents into the cells. Indeed they were selectively processed to large numbers of target miRNAs and siRNAs in human cells, as determined by unbiased deep sequencing studies (FIG. 2a-2b). So was the scrambled RNA from OnRS/Neg. The presence of small RNA isoforms differing in 1- or 2-nt at 5' or 3' within chimeric ncRNA- and vehicle-treated human cells may indicate the flexibilities of endoribonucleases in producing small RNAs from pre-miRNAs or shRNAs (31-33). As a result, selective stem-loop RT-qPCR assays revealed a three orders of magnitude increase in miR-124 in A549 cells and GFP siRNA in ES-2/GFP cells, respectively. The results are also in good agreement with our findings on the stability of tRNA/mir-34a chimera in human cells (unpublished data), i.e., the increases in target small RNAs levels were associated with higher levels of OnRS chimeras lasting as long as 4 days post-treatment, which highlights a favorable stability of OnRS chimeras within human cells. On the other hand, there were no or diminutive changes in the levels of other cellular miRNAs, and the tRNA-derived tRFs exhibited similar patterns in the same human cell lines (FIG. 2c-2d). Nevertheless, the levels of individual or total tRFs identified in ES-2/GFP cells were much lower than A549 cells, which is presumably due to the differences in generating, degrading, excreting and/or retaining tRFs in different types of cells. In addition, while the target miR-NAs/siRNAs, tRFs and other small RNAs derived from chimeric ncRNA agents in human cells were fully elucidated, the roles of specific ribonucleases such as Dicer in the processes remain undefined.

Figure 3:
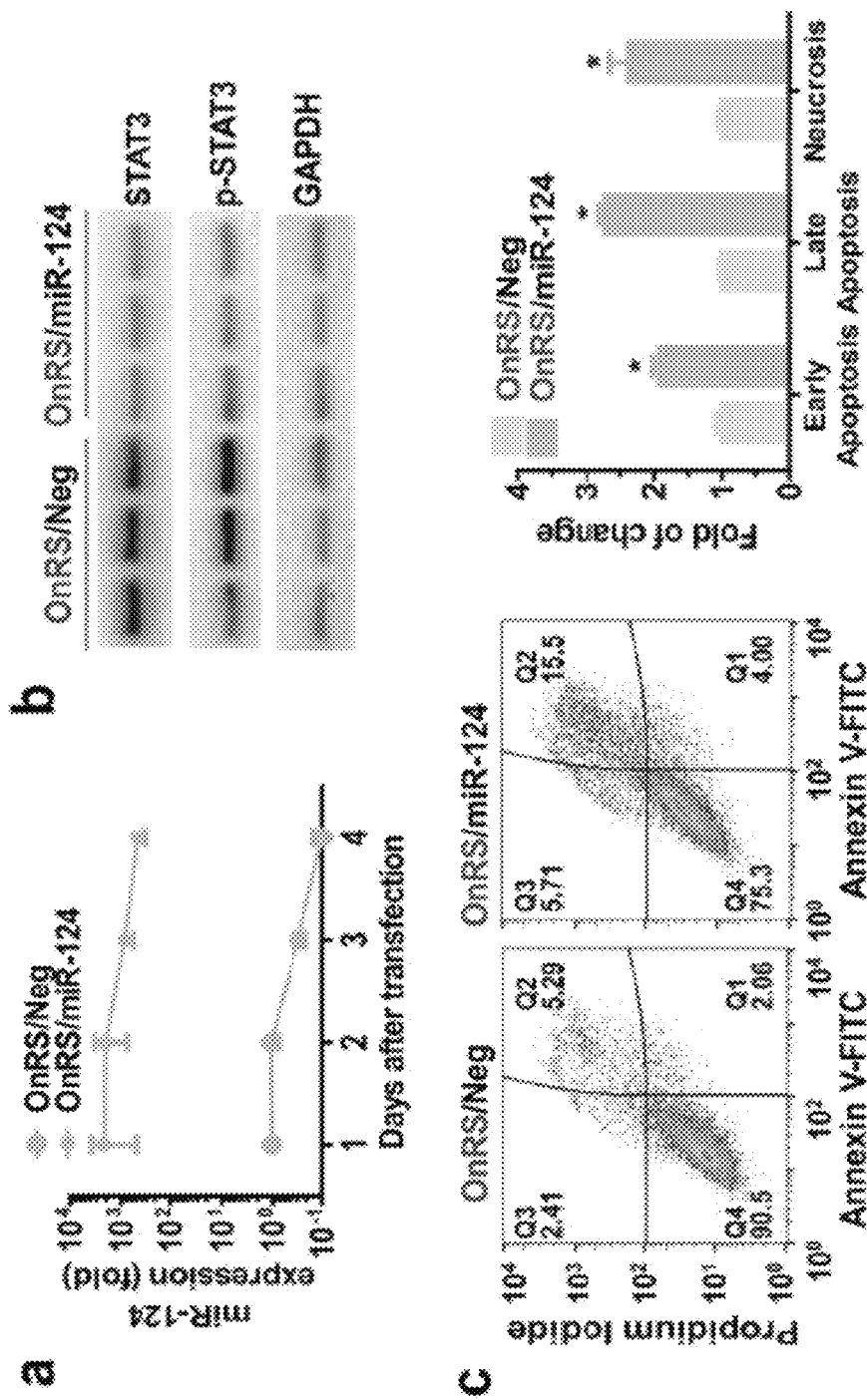
FIG. 3 illustrates OnRS-carried miRNA is biologically/pharmacologically active in regulating target gene expression and controlling cellular processes in human cells. (a) RT-qPCR analysis revealed that mature miR-124 levels retained 3 orders of magnitude higher in A549 cells for 4 days since transfection with OnRS/miR-124, as compared with OnRS/Neg. (b) Western blots showed that OnRS/miR-124 was effective in reducing the protein expression level of miR-124 target gene STAT3 in A549 cells at 72 h post-transfection. (c) Flow cytometric analyses demonstrated that OnRS/miR-124 was effective in inducing apoptosis in A549 cells at 48 h post-transfection. Cells treated with OnRS/Neg were used as controls. (d) MTT assay showed that OnRS/miR-124 significantly suppressed the proliferation of A549 cells at 72 h post-treatment, as compared to OnRS/Neg. (e) Inhibition of A549 cell proliferation by OnRS/miR-124 was also demonstrated when cell growth was monitored using Icelligence Real-Time Cell analyzer. The arrow points to the time point of ncRNA treatment. Values are mean±SD of triplicated treatments. *$P<0.01$.
Figure 3:
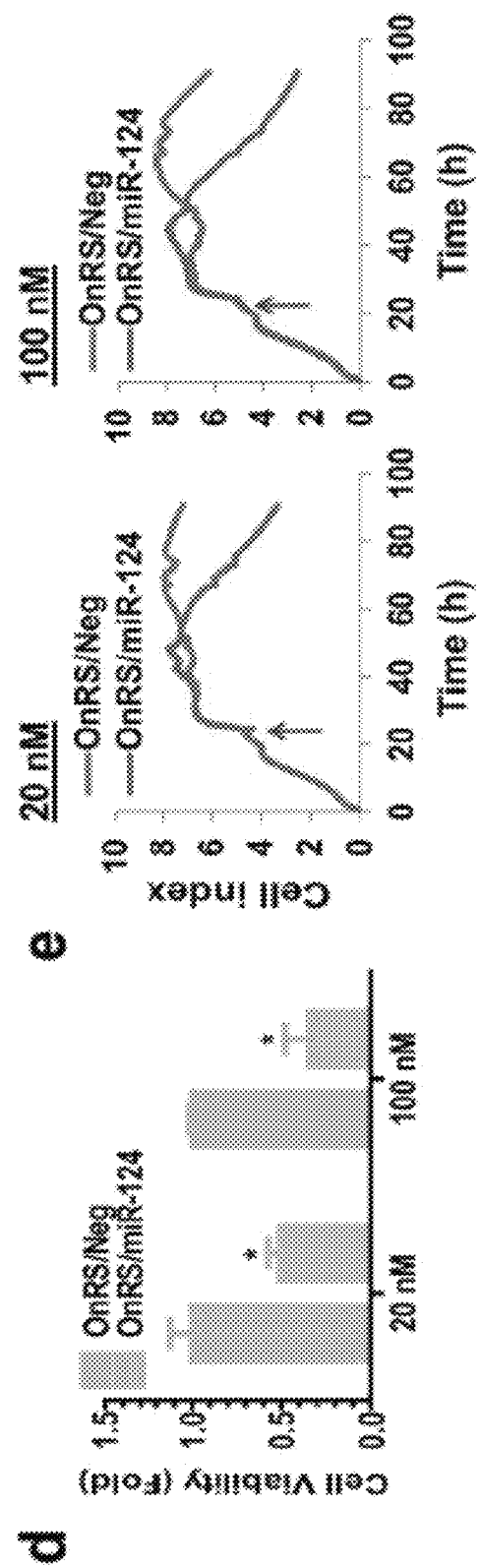
Figure 4:
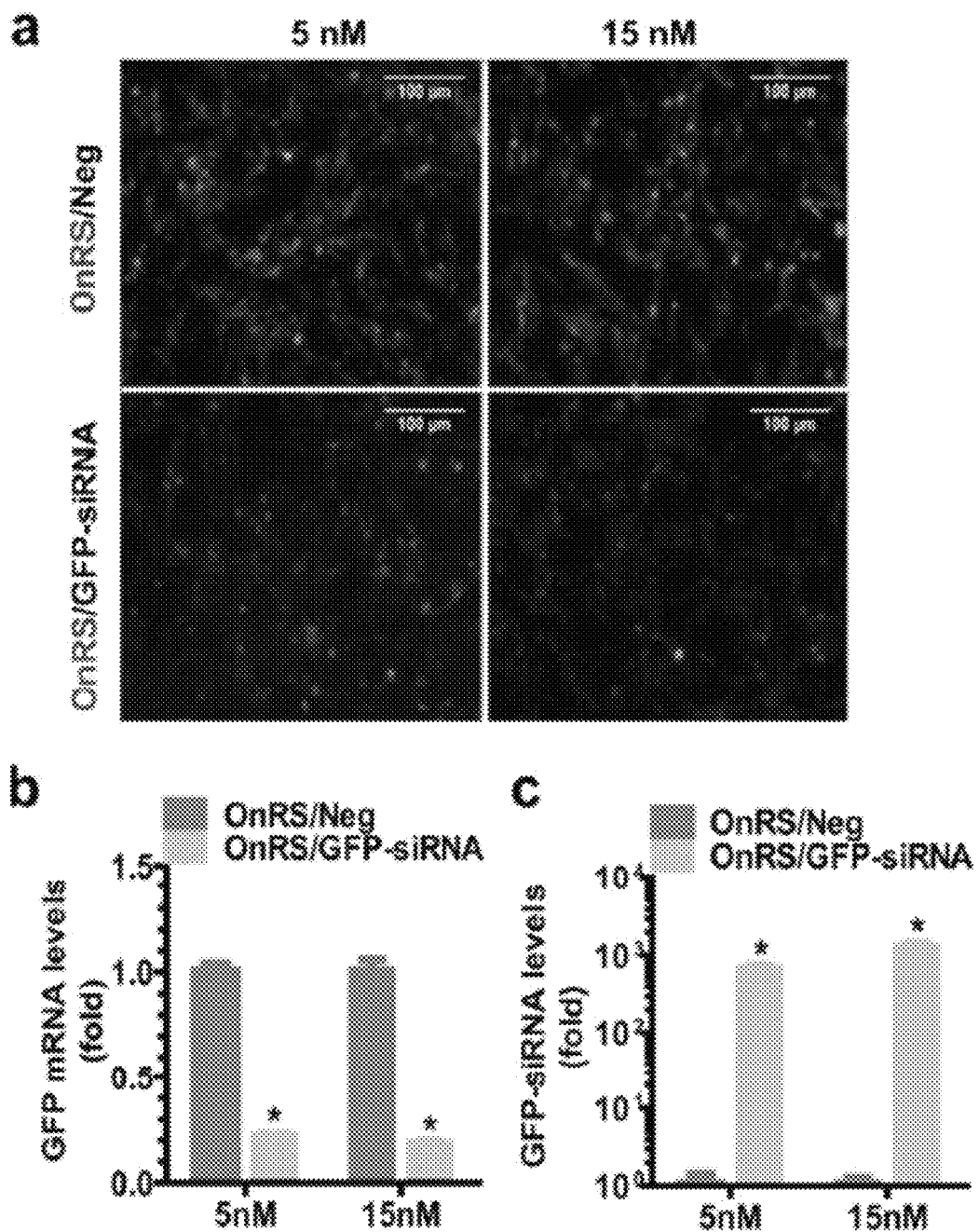
FIG. 4 illustrates OnRS-carried siRNA is effective for RNAi in vitro and in vivo. GFP fluorescence intensity was sharply reduced in ES-2/GFP cells in vitro at 72 h after transfected with OnRS/GFP-siRNA (a), which was associated with (b) 70-80% lower GFP mRNA levels and (c) 1000-fold higher GFP siRNA levels. Following i.v. administration of OnRS/GFP-siRNA, hepatic GFP fluorescence was significantly suppressed in the GFP-transgenic mouse models in vivo, as demonstrated by microscopic examination of (d) non-fixed and (e) fixed liver slices, as well as (f) RT-qPCR analysis of hepatic GFP mRNA levels. Fixed liver slices were stained with DAPI, and GFP fluorescence and DAPI-stained nuclei (blue) images were merged together (e). Control RS-2/GFP cells (N=3 per group) or GFP-transgenic mice (N=3-4 per group) were treated with the same doses of OnRS/Neg. Values are mean±SD. *$P<0.01$, compared with OnRS/Neg treatment.
Figure 4:
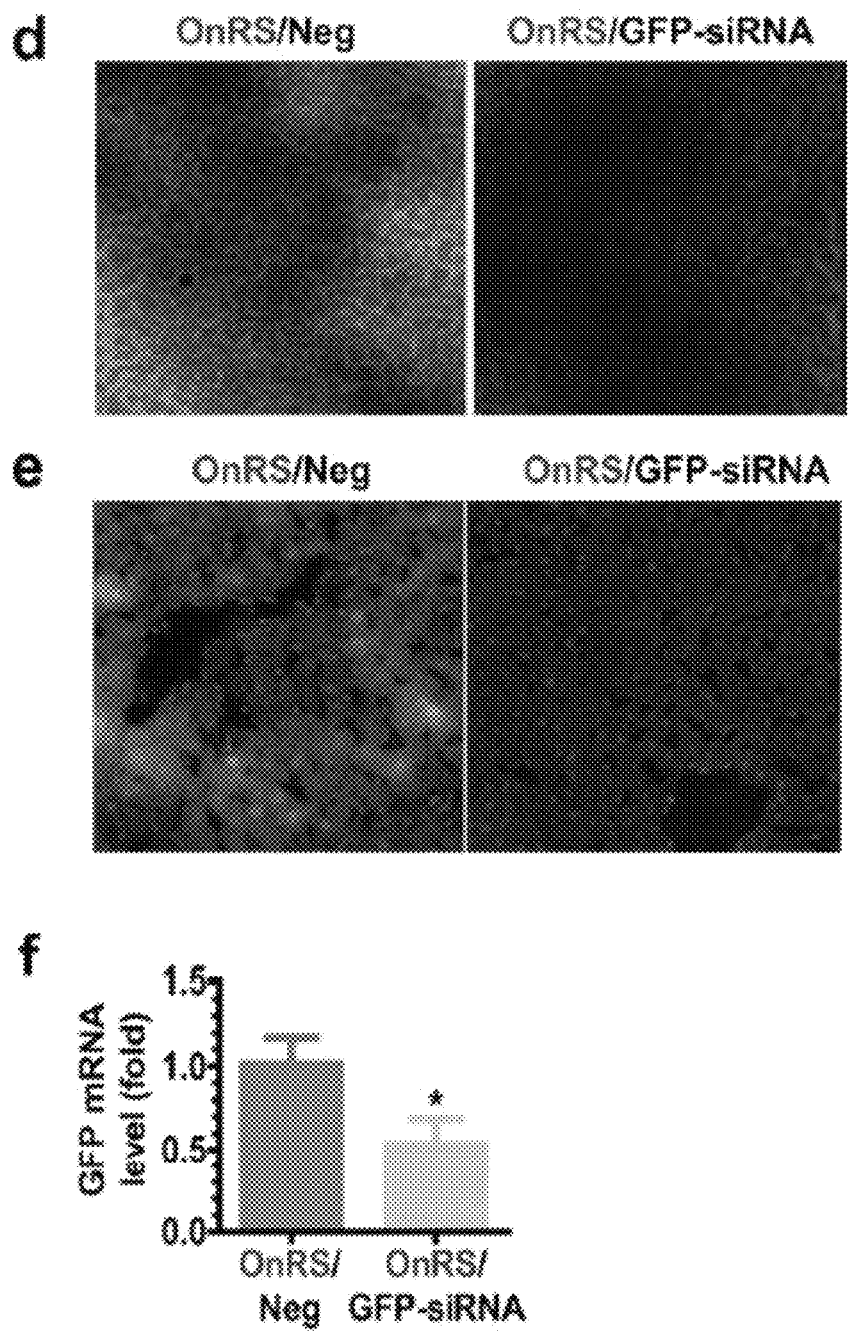

The bioactivities of miRNAs (FIG. 3) and siRNAs (FIG. 4) released from the OnRS cargo are clearly demonstrated by the selective suppression of corresponding target gene expression in vitro and in vivo, using the OnRS/Neg as a control. The transcription factor STAT3, a known miR-124 target gene (27,28), plays an important role in many cellular processes such as cell proliferation and apoptosis. Reduction of STAT3 protein expression levels by miR-124 may at least partially provide an explanation for the enhanced apoptosis and repressed proliferation of A549 cells (FIG. 3). On the other hand, the suppression of GFP mRNA expression levels in GFP-expressing ES-2/GFP cells and GFP-transgenic mouse liver tissues by OnRS-delivered GFP siRNA explains the lower GFP fluorescent intensities (FIG. 4). While the advantages and disadvantages of using recombinant DNA agents, synthetic and recombinant RNAs to achieve RNAi are undoubtedly subjects of debate, the OnRS-based technology offers a new opportunity to readily and cost-effectively produce multi-milligrams of chimeric miRNA and siRNA agents in a research laboratory setting and allows one to utilize biological RNAs to perform RNA actions in vitro and in vivo. Nevertheless, the relative selectivity, efficiency and safety of OnRS-carried RNAi agents, as compared to existing agents or methods, await more extensive evaluation.

Figure 5:
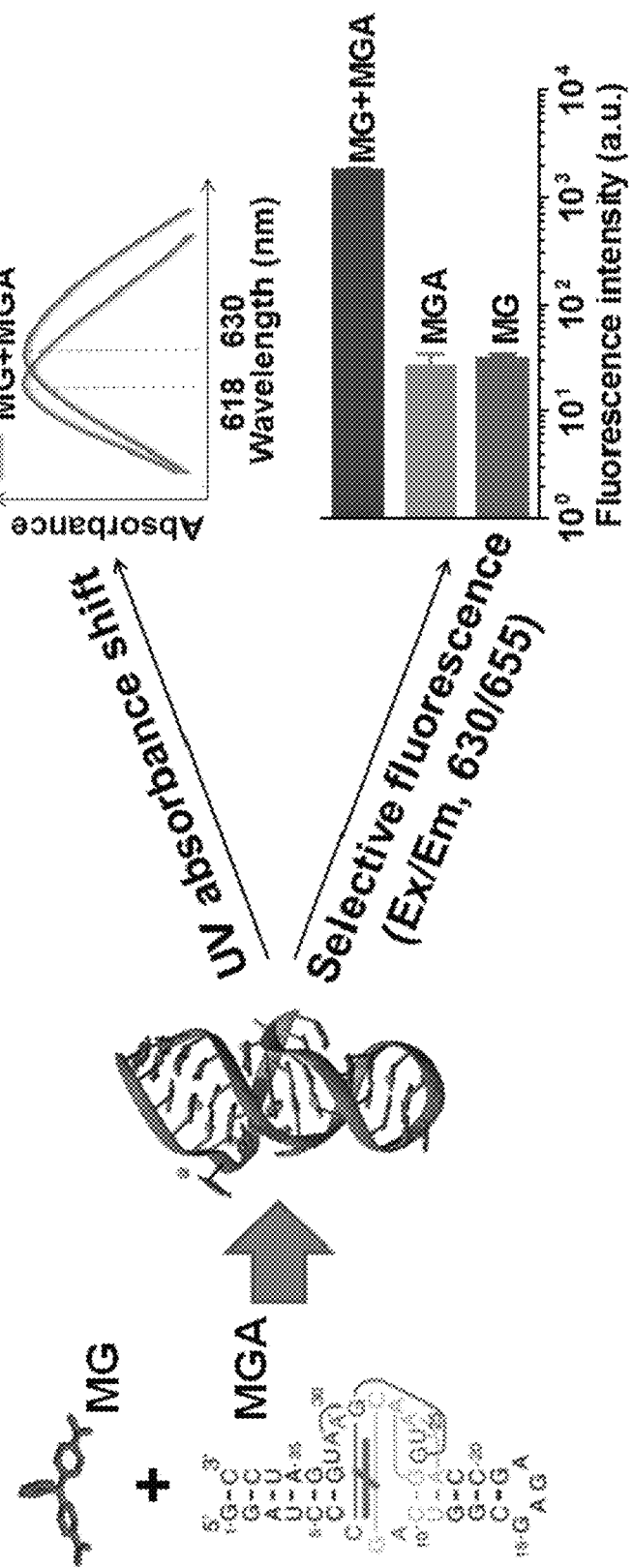
FIG. 5 illustrates the basic principle of the herein described RNase assay method using a malachite green aptamer (MGA) sensor (SEQ ID NO: 9).

The utility of OnRS was further extended to consistent high-yield production of RNA aptamers. A priori it is unknown whether aptamer activity would still be present in the tRNA (13-15) and 5S rRNA (16) scaffolds, although ribozyme activity was observed in the context of the tRNA scaffold when Hammerhead ribozyme sequences were inserted together with the target RNA to be produced (15). The OnRS-resembled RNA aptamer MGA sensor indeed interacted with MG to produce a specific strong fluorescence at 630/650 nm (excitation/emission; FIG. 5e), as it was originally discovered (9), which was further employed for the determination of serum RNase activities in clinical samples (FIG. 7e). The RNase activity assay using label-free MGA sensor developed in this study is different from current methods. The Kunitz RNase activity assay (29,34-36) is based upon the ultraviolet absorbance of label-free nucleic acids at 260 nm or nucleosides at 280 nm, which is relatively less selective and sensitive. Recent and current RNase activity assays including those commercially-available kits rely on isotope- or fluorophore-labeled RNAs or antibodies (37-40), and thus offer greater sensitivities to determine very low levels of RNase activities or indicate RNase protein levels. However, human serum is comprised of much higher RNase activities. Without extensive dilutions (e.g., 1:1,000) of the serum sample that might affect the RNase activity assay including linear range, larger quantities (e.g., >10 µg) of labeled synthetic RNA agents are needed, and thus the assays become costly. After careful examination of the linearity in relation to MG and OnRS/MGA concentrations as well as the quantity of human serum and incubation time, we were able to establish a fluorescence-based RNase assay using label-free OnRS/MGA sensor. Consistent with previous findings (29,36,38), our assays revealed a significantly higher serum RNase activity in PDAC patients which may be attributable to the major form RNase A released from the cancerous pancreases.

In summary, we presented a novel OnRS-based general approach for a consistent high-yield production of chimeric RNAs in common *E. coli* strains that carry functional small RNAs of interests such as miRNAs, siRNAs and RNA aptamers. This approach is proven robust and versatile and shall have broad applications to engineer chimeric ncRNAs, which may be utilized as in vitro and in vivo research tools and further developed as diagnostic and therapeutic agents.

REFERENCES

1. Dykxhoorn, D. M. and Lieberman, J. (2006) Knocking down disease with siRNAs. Cell, 126, 231-235.
2. Burnett, J. C. and Rossi, J. J. (2012) RNA-based therapeutics: current progress and future prospects. Chemistry & biology, 19, 60-71.
3. Kole, R., Krainer, A. R. and Altman, S. (2012) RNA therapeutics: beyond RNA interference and antisense oligonucleotides. Nature reviews. Drug discovery, 11, 125-140.
4. Ulrich, H., Trujillo, C. A., Nery, A. A., Alves, J. M., Majumder, P., Resende, R. R. and Martins, A. H. (2006) DNA and RNA aptamers: from tools for basic research towards therapeutic applications. Combinatorial chemistry & high throughput screening, 9, 619-632.
5. Kelnar, K., Peltier, H. J., Leatherbury, N., Stoudemire, J. and Bader, A. G. (2014) Quantification of therapeutic miRNA mimics in whole blood from non-human primates. Analytical chemistry, 86, 1534-1542.
6. Ling, H., Fabbri, M. and Calin, G. A. (2013) MicroRNAs and other non-coding RNAs as targets for anticancer drug development. Nature reviews. Drug discovery, 12, 847-865.
7. Takahashi, M., Yamada, N., Hatakeyama, H., Murata, M., Sato, Y., Minakawa, N., Harashima, H. and Matsuda, A. (2013) In vitro optimization of 2'-OMe-4'-thioribonucleoside-modified anti-microRNA oligonucleotides and its targeting delivery to mouse liver using a liposomal nanoparticle. Nucleic acids research, 41, 10659-10667.
8. Gebert, L. F., Rebhan, M. A., Crivelli, S. E., Denzler, R., Stoffel, M. and Hall, J. (2014) Miravirsen (SPC3649) can inhibit the biogenesis of miR-122. Nucleic acids research, 42, 609-621.
9. Babendure, J. R., Adams, S. R. and Tsien, R. Y. (2003) Aptamers switch on fluorescence of triphenylmethane dyes. Journal of the American Chemical Society, 125, 14716-14717.
10. Beckert, B. and Masquida, B. (2011) Synthesis of RNA by in vitro transcription. Methods in molecular biology, 703, 29-41.
11. Huang, F., He, J., Zhang, Y. and Guo, Y. (2008) Synthesis of biotin-AMP conjugate for 5' biotin labeling of RNA through one-step in vitro transcription. Nature protocols, 3, 1848-1861.
12. Huang, L., Jin, J., Deighan, P., Kiner, E., McReynolds, L. and Lieberman, J. (2013) Efficient and specific gene knockdown by small interfering RNAs produced in bacteria. Nature biotechnology, 31, 350-356.
13. Ponchon, L. and Dardel, F. (2007) Recombinant RNA technology: the tRNA scaffold. Nature methods, 4, 571-576.
14. Ponchon, L., Beauvais, G., Nonin-Lecomte, S. and Dardel, F. (2009) A generic protocol for the expression and purification of recombinant RNA in *Escherichia coli* using a tRNA scaffold. Nature protocols, 4, 947-959.
15. Nelissen, F. H., Leunissen, E. H., van de Laar, L., Tessari, M., Heus, H. A. and Wijmenga, S. S. (2012) Fast production of homogeneous recombinant RNA—towards large-scale production of RNA. Nucleic acids research, 40, e102.
16. Liu, Y., Stepanov, V. G., Strych, U., Willson, R. C., Jackson, G. W. and Fox, G. E. (2010) DNAzyme-mediated recovery of small recombinant RNAs from a 5S rRNA-derived chimera expressed in *Escherichia coli*. BMC biotechnology, 10, 85.
17. Li, M. M., Wang, W. P., Wu, W. J., Huang, M. and Yu, A. M. (2014) Rapid Production of Novel Pre-MicroRNA Agent hsa-mir-27b in *Escherichia coli* Using Recombinant RNA Technology for Functional Studies in Mammalian Cells. Drug metabolism and disposition: the biological fate of chemicals, 42, 1791-1795.
18. Sato, K., Hamada, M., Asai, K. and Mituyama, T. (2009) CENTROIDFOLD: a web server for RNA secondary structure prediction. Nucleic acids research, 37, W277-280.
19. Hamada, M., Yamada, K., Sato, K., Frith, M. C. and Asai, K. (2011) CentroidHomfold-LAST: accurate prediction of RNA secondary structure using automatically collected homologous sequences. Nucleic acids research, 39, W100-106.
20. Meyer, C., Grey, F., Kreldywich, C. N., Andoh, T. F., Tirabassi, R. S., Orloff, S. L. and Streblow, D. N. (2011) Cytomegalovirus microRNA expression is tissue specific and is associated with persistence. Journal of virology, 85, 378-389.
21. Wei, Z., Liu, X., Feng, T. and Chang, Y. (2011) Novel and conserved micromas in Dalian purple urchin (*Strongylocentrotus nudus*) identified by next generation sequencing. International journal of biological sciences, 7, 180-192.
22. Bi, H. C., Pan, Y. Z., Qiu, J. X., Krausz, K. W., Li, F., Johnson, C. H., Jiang, C. T., Gonzalez, F. J. and Yu, A. M. (2014) N-methylnicotinamide and nicotinamide N-methyltransferase are associated with microRNA-1291-altered pancreatic carcinoma cell metabolome and suppressed tumorigenesis. Carcinogenesis, 35, 2264-2272.
23. Pan, Y. Z., Zhou, A., Hu, Z. and Yu, A. M. (2013) Small nucleolar RNA-derived microRNA hsa-miR-1291 modulates cellular drug disposition through direct targeting of ABC transporter ABCC1. Drug metabolism and disposition: the biological fate of chemicals, 41, 1744-1751.
24. Okabe, M., Ikawa, M., Kominami, K., Nakanishi, T. and Nishimune, Y. (1997) 'Green mice' as a source of ubiquitous green cells. FEBS letters, 407, 313-319.
25. Boudreau, R. L. and Davidson, B. L. (2012) Generation of hairpin-based RNAi vectors for biological and therapeutic application. Methods in enzymology, 507, 275-296.
26. Cao, X., Pfaff, S. L. and Gage, F. H. (2007) A functional study of miR-124 in the developing neural tube. Genes & development, 21, 531-536.
27. Cai, B., Li, J., Wang, J., Luo, X., Ai, J., Liu, Y., Wang, N., Liang, H, Zhang, M., Chen, N. et al. (2012) microRNA-124 regulates cardiomyocyte differentiation of bone marrow-derived mesenchymal stem cells via targeting STAT3 signaling. Stem cells, 30, 1746-1755.
28. Hatziapostolou, M., Polytarchou, C., Aggelidou, E., Drakaki, A., Poultsides, G. A., Jaeger, S. A., Ogata, H., Karin, M., Struhl, K., Hadzopoulou-Cladaras, M. et al. (2011) An HNF4alpha-miRNA inflammatory feedback circuit regulates hepatocellular oncogenesis. Cell, 147, 1233-1247.
29. Reddi, K. K. and Holland, J. F. (1976) Elevated serum ribonuclease in patients with pancreatic cancer. Proceedings of the National Academy of Sciences of the United States of America, 73, 2308-2310.
30. Akagi, K., Murai, K., Hirao, N. and Yamanaka, M. (1976) Purification and properties of alkaline ribonuclease from human serum. Biochimica et biophysica acta, 442, 368-378.
31. Gu, S., Jin, L., Zhang, Y., Huang, Y., Zhang, F., Valdmanis, P. N. and Kay, M. A. (2012) The loop position of shRNAs and pre-miRNAs is critical for the accuracy of dicer processing in vivo. Cell, 151, 900-911.
32. Castellano, L. and Stebbing, J. (2013) Deep sequencing of small RNAs identifies canonical and non-canonical miRNA and endogenous siRNAs in mammalian somatic tissues. Nucleic acids research, 41, 3339-3351.
33. Dueck, A., Ziegler, C., Eichner, A., Berezikov, E. and Meister, G. (2012) microRNAs associated with the different human Argonaute proteins. Nucleic acids research, 40, 9850-9862.
34. Kunitz, M. (1950) Crystalline desoxyribonuclease; isolation and general properties; spectrophotometric method for the measurement of desoxyribonuclease activity. The Journal of general physiology, 33, 349-362.
35. Crook, E. M., Mathias, A. P. and Rabin, B. R. (1960) Spectrophotometric assay of bovine pancreatic ribonuclease by the use of cytidine 2':3'-phosphate. The Biochemical journal, 74, 234-238.
36. Peterson, L. M. (1979) Serum RNase in the diagnosis of pancreatic carcinoma. Proceedings of the National Academy of Sciences of the United States of America, 76, 2630-2634.
37. Potenza, N., Salvatore, V., Migliozzi, A., Martone, V., Nobile, V. and Russo, A. (2006) Hybridase activity of human ribonuclease-1 revealed by a real-time fluorometric assay. Nucleic acids research, 34, 2906-2913.
38. Kottel, R. H., Hoch, S. O., Parsons, R. G. and Hoch, J. A. (1978) Serum ribonuclease activity in cancer patients. British journal of cancer, 38, 280-286.
39. Vlassov, A., Florentz, C., Helm, M., Naumov, V., Buneva, V., Nevinsky, G. and Giege, R. (1998) Characterization and selectivity of catalytic antibodies from human serum with RNase activity. Nucleic acids research, 26, 5243-5250.
40. Nakata, D. (2014) Increased N-glycosylation of Asn(8) (8) in serum pancreatic ribonuclease 1 is a novel diagnostic marker for pancreatic cancer. Scientific reports, 4, 6715.

Informal Sequence Listing

Underlined are tRNA sequences, and the italic are hsa-mir-34a sequences. Italic bold sequences are extended 5' and 3' sequences of hsa-mir-34a. Underlined italic bold represents mutated nucleotides. The boxed are MGA sequences.

SEQ ID NO: 1 - tRNA/MSA (107 nt):
5'-GGCUACGUAGCUCAGUUGGUUAGAGCAGCGGCCGAGUAAUUUACGUCGACGG

UGACGUCGAUGGUUGCGGCCGCGGGUCACAGGUUCGAAUCCCGUCGUAGCCACCA-3'

SEQ ID NO: 2 - Human Pre-miR-34a (hsa-mir-34a; MI0000268)
5'-GGCCAGCUGUGAGUGUUUCUUUGGCAGUGUCUUAGCUGGUUGUUGUGAGC

AAUAGUAAGGAAGCAAUCAGCAAGUAUACUGCCCUAGAAGUGCUGCACGUUGUGGGGCCC-
3'

SEQ ID NO: 3 - OnRS-1 or tRNA/mir-34a (233 nt):
5'-GGCUACGUAGCUCAGUUGGUUAGAGCAGCGGCCGAGUAAUUUACGUCGAC

*GUGGACC*GGCCAGCUGUGAGUGUUUCUUUGGCAGUGUCUUAGCUGGUUGU

UGUGAGCAAUAGUAAGGAAGCAAUCAGCAAGUAUACUGCCCUAGAAGUGC

UGCACGUUGUGGGGCCC*AAGAGGGAAGAU*GACGUCGAUGGUUGCGGCCGC

GGGUCACAGGUUCGAAUCCCGUCGUAGCCACCA-3'

SEQ ID NO: 4 - OnRS-2 (195 nt):
5'-GGCUACGUAGCUCAGUUGGUUAGAGCAGCGGCCG*GUGGACC*GGCCAGCUG

*UGAGUGUUUCUUUGGCAGUGUCUUAGCUGGUUGUUGUGAGCAAUAGUAAG*

*GAAGCAAUCAGCAAGUAUACUGCCCUAGAAGUGCUGCACGUUGUGGGGCC*

*C**GGUCCAC**CCGCGGGUCACAGGUUCGAAUCCCGUCGUAGCCACCA-3*

SEQ ID NO: 5 - OnRS-3 (199 nt):
5'-GGCUACGUAGCUCAGUUGGUUAGAGCAGCGGCCGGGCCAGCUGUGAGUGU

*UUCUUUGGCAGUGUCUUAGCUGGUUGUUGUGAGCAAUAGUAAGGAAGCAA*

*UCAGCAAGUAUACUGCCCUAGAAGUGCUGCACGUUGUGGGGCCC*GACGUC

GAUGGUUGCGGCCGCGGGUCACAGGUUCGAAUCCCGUCGUAGCCACCA-3'

SEQ ID NO: 6 - OnRS-4a (182 nt):
5'-GGCUACGUAGCUCAGUUGGUUAGAGCAGCGGCCGGGCCAGCUGUGAGUGU

*UUCUUUGGCAGUGUCUUAGCUGGUUGUUGUGAGCAAUAGUAAGGAAGCAA*

*UCAGCAAGUAUACUGCCCUAGAAGUGCUGCACGUUGUGGGGCCC*CCGCGG

GUCACAGGUUCGAAUCCCGUCGUAGCCACCA-3'

SEQ ID NO: 7 - OnRS-4b (181 nt):
5'-GGCUACGUAGCUCAGUUGGUUAGAGCAGCGGCCGGGCCAGCUGUGAGUGU

*UUCUUUGGCAGUGUCUUAGCUGGUUGUUGUGAGCAAUAGUAAGGAAGCAA*

*UCAGCAAGUAUACUGCCCUAGAAGUGCUGCACGUUGU**U**GGCCCC*CGCGG

GUCACAGGUUCGAAUCCCGUCGUAGCCACCA-3'

SEQ ID NO: 8 - OnRS-5 (182 nt):
5'-GGCUACGUAGCUCAGUUGGUUAGAGCAGCGGCCGGGCC*CC*GCUGUGAGUG

*UUUCUUUGGCAGUGUCUUAGCUGGUUGUUGUGAGCAAUAGUAAGGAAGCA*

*AUCAGCAAGUAUACUGCCCUAGAAGUGCUGCACGUUGUGGGGCCC*CCGCG

GGUCACAGGUUCGAAUCCCGUCGUAGCCACCA-3'

SEQ ID NO: 9 - Malachite Green Aptamer (MGA) (38 nt):
5'-GGAUCCCGACUGGCGAGAGCCAGGUAACGAAUGGAUCC-3'

SEQ ID NO: 10 - OnRS-2/MGA5 (233 nt):
5'-GGCUACGUAGCUCAGUUGGUUAGAGCAGCGGCCGGGAUCCCGACUGGCGA

-continued

GAGCCAGGUAACGAAUGGAUCC*GUGGACC*GGCCAGCUGUGAGUGUUUCUU

*UGGCAGUGUCUUAGCUGGUUGUUGUGAGCAAUAGUAAGGAAGCAAUCAGC*

*AAGUAUACUGCCCUAGAAGUGCUGCACGUUGUGGGGCCC**GGUCCAC*CCGC

GGGUCACAGGUUCGAAUCCCGUCGUAGCCACCA-3'

SEQ ID NO: 11 - OnRS-2/MGA3 (233 nt):
5'-<u>GGCUACGUAGCUCAGUUGGUUAGAGCAGCGGCCG</u>*GUGGACC**GGCCAGCUG*

*UGAGUGUUUCUUUGGCAGUGUCUUAGCUGGUUGUUGUGAGCAAUAGUAAG*

*GAAGCAAUCAGCAAGUAUACUGCCCUAGAAGUGCUGCACGUUGUGGGGCC*

*C**GGUCCAC*GGAUCCCGACUGGCGAGAGCCAGGUAACGAAUGGAUCC CCGC

GGGUCACAGGUUCGAAUCCCGUCGUAGCCACCA-3'

Pre-miR-1291 (121 nt)
                                               Sequence ID No: 12
5'-AGUUCUGUCCGUGAGCCUUGGGUAGAAUUCCAGUGGCCCUGACUGAAGACCAGCAGUU

GUACUGUGGCUGUUGGUUUCAAGCAGAGGCCUAAAGGACUGUCUUCCUGUGGUCUGUUGGC

UG-3' tRNA/mir-1291 chimera (227 nt)
                                               Sequence ID No: 13
5'-GGCUACGUAGCUCAGUUGGUUAGAGCAGCGGCCGAGUAAUUUACGUCGACGAGUUCUG

UCCGUGAGCCUUGGGUAGAAUUCCAGUGGCCCUGACUGAAGACCAGCAGUUGUACUGUGGC

UGUUGGUUUCAAGCAGAGGCCUAAAGGACUGUCUUCCUGUGGUCUGUUGGCUGUGACGUCG

AUGGUUGCGGCCGCGGGUCACAGGUUCGAAUCCCGUCGUAGCCACCA-3'

Pre-miR-125-1 (110 nt)
                                               Sequence ID No: 14
5'-AGAAAACAUUGUUGCGCUCCUCUCAGUCCCUGAGACCCUAACUUGUGAUGUUUACCGU

UUAAAUCCACGGGUUAGGCUCUUGGGAGCUGCGAGUCGUGCUUUUGCAUCCU-3' tRNA/mir-125-1 chimera (216 nt)
                                               Sequence ID No: 15
5'-GGCUACGUAGCUCAGUUGGUUAGAGCAGCGGCCGAGUAAUUUACGUCGACGAGAAAAC

AUUGUUGCGCUCCUCUCAGUCCCUGAGACCCUAACUUGUGAUGUUUACCGUUUAAAUCCAC

GGGUUAGGCUCUUGGGAGCUGCGAGUCGUGCUUUUGCAUCCUUGACGUCGAUGGUUGCGGC

CGCGGGUCACAGGUUCGAAUCCCGUCGUAGCCACCA-3'

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

---

What is claimed is:

1. A polynucleotide comprising:
   a tRNA operably linked to a pre-microRNA (pre-miRNA), wherein all or part of the stem-loop anticodon of the tRNA is replaced with the pre-miRNA; and
   an aptamer that binds to a fluorescent dye selected from the group consisting of: malachite green, tetramethylrosamine, sulforhodamine B, and a triphenylmethane dye, wherein the aptamer is disposed between the tRNA and the pre-miRNA.

2. The polynucleotide of claim 1, wherein the fluorescent dye is malachite green.

3. The polynucleotide of claim 1, wherein the aptamer comprises a nucleotide sequence having at least 90% sequence identity to the nucleotide sequence of SEQ ID NO:9.

4. The polynucleotide of claim 1, wherein the aptamer is disposed 5' to the pre-miRNA.

5. The polynucleotide of claim 1, wherein the aptamer is disposed 3' to the pre-miRNA.

6. The polynucleotide of claim 1, wherein the tRNA is a methionyl tRNA.

7. The polynucleotide of claim 6, wherein the tRNA comprises a nucleotide sequence having at least 90% sequence identity to the nucleotide sequence of SEQ ID NO: 1.

8. The polynucleotide of claim 1, wherein the pre-miRNA is selected from pre-miRNA-1291, pre-miRNA-34a, and pre-miRNA-125-1.

9. The polynucleotide of claim 8, wherein:
   a) the pre-miRNA is a pre-miRNA-1291 comprising a nucleotide sequence having at least 90% sequence identity to SEQ ID NO: 12;
   b) the pre-miRNA is a pre-miRNA-34a comprising a nucleotide sequence having at least 90% sequence identity to SEQ ID NO:2; and/or
   c) the pre-miRNA is a pre-miRNA-125-1 comprising a nucleotide sequence having at least 90% sequence identity to SEQ ID NO: 14.

10. The polynucleotide of claim 9, wherein the tRNA is:
    a) a methionyl tRNA comprising a nucleotide sequence having at least 90% sequence identity to the nucleotide sequence of SEQ ID NO: 13;
    b) a methionyl tRNA comprising a nucleotide sequence having at least 90% sequence identity to the nucleotide sequence of SEQ ID NO:3; or
    c) a methionyl tRNA comprising a nucleotide sequence having at least 90% sequence identity to the nucleotide sequence of SEQ ID NO: 15.

11. The polynucleotide of claim 1, wherein the tRNA operably linked to the pre-miRNA comprises a nucleotide sequence having at least 90% sequence identity to a polynucleotide selected from the group consisting of: SEQ ID NO:3, SEQ ID NO:4, SEQ ID NO:5, SEQ ID NO:6, SEQ ID NO:7, SEQ ID NO:8, SEQ ID NO:13, and SEQ ID NO:15.

12. The polynucleotide of claim 1, wherein the tRNA comprises a nucleotide sequence having at least 90% sequence identity to SEQ ID NO:10.

13. The polynucleotide of claim 1, wherein the tRNA comprises a nucleotide sequence having at least 90% sequence identity to SEQ ID NO:11.

14. A composition comprising the polynucleotide of claim 1.

15. The composition of claim 14, further comprising a detectable label bound by the aptamer.

16. A kit comprising:
    the polynucleotide of claim 1; and
    a fluorescent dye selected from the group consisting of: malachite green, tetramethylrosamine, sulforhodamine B, and a triphenylmethane dye.

* * * * *